US008911946B2

(12) United States Patent
Becker et al.

(10) Patent No.: US 8,911,946 B2
(45) Date of Patent: Dec. 16, 2014

(54) DETECTION OF ANTIBIOTIC-RESISTANT MICROORGANISMS

(75) Inventors: Michael M. Becker, San Diego, CA (US); Kui Gao, San Diego, CA (US); Wai-Chung Lam, Bonsall, CA (US)

(73) Assignee: Gen-Probe Incorporated, San Diego, CA (US)

( * ) Notice: Subject to any disclaimer, the term of this patent is extended or adjusted under 35 U.S.C. 154(b) by 137 days.

(21) Appl. No.: 12/340,622

(22) Filed: Dec. 19, 2008

(65) Prior Publication Data

US 2009/0181395 A1 Jul. 16, 2009

Related U.S. Application Data

(60) Provisional application No. 61/041,146, filed on Mar. 31, 2008, provisional application No. 61/015,954, filed on Dec. 21, 2007.

(51) Int. Cl.
 *C12Q 1/68* (2006.01)
 *C12P 19/34* (2006.01)

(52) U.S. Cl.
 CPC .................................. *C12Q 1/689* (2013.01)
 USPC .................. 435/6.12; 435/91.2; 435/91.1

(58) Field of Classification Search
 USPC .................................. 435/6, 91.2, 91.1, 6.12
 See application file for complete search history.

(56) References Cited

U.S. PATENT DOCUMENTS

| 5,554,516 | A | 9/1996 | Kacian et al. | |
| 6,503,709 | B1 * | 1/2003 | Bekkaoui et al. | 435/6 |
| 6,783,934 | B1 * | 8/2004 | McMillan et al. | 435/6 |
| 8,017,337 | B2 | 9/2011 | Paitan | |

FOREIGN PATENT DOCUMENTS

| EP | 1522595 A2 | 4/2005 |
| KR | 1020070069680 A | 3/2007 |
| WO | 02082086 A2 | 10/2002 |
| WO | 2006026388 A2 | 3/2006 |
| WO | 2007023461 A2 | 3/2007 |

OTHER PUBLICATIONS

Abe et al., "Internally controlled simultaneous real-time PCR of the MecA gene and the *S. aureus* SCCmec-orfX gene junction region for the detection of methicillin-resistant *Staphylococcus aureus* (MRSA) directly from swab specimens on the LightCycler instrument," p. 29, Abstracts: Congress of Clinical Chemistry and Laboratory Medicine, Oct. 1-4, 2006, Mannheim, Germany.
Desjardins et al., "Evaluation of the IDI-MRSA Assay for Detection of Methicillin-Resistant *Staphylococcus aureus* from Nasal and Rectal Specimens Pooled in a Selective Broth," J. Clin. Microbiol., 2006, 44(4):1219-1223, Am. Society for Microbiology, USA.
Elsayed et al., "Development and Validation of a Molecular Beacon Probe-Based Real-Time Polymerase Chain Reaction Assay for Rapid Detection of Methicillin Resistance is *Staphylococcus aureus*," Arch. Pathol. Lab. Med., 2003, 127:845-849, College of American Pathologists, USA.
Germer et al., "High-Throughput SNP Allele-Frequency Determination in Pooled DNA Samples by Kinetic PCR," Genome Research, 1999, pp. 258-266, Cold Spring Harbor Laboratory Press, USA.
Kaplan et al., "Sensitivity and Specificity of a Rapid rRNA Gene Probe Assay for Simultaneous Identification of *Staphylococcus aureus* and Detection of mecA," J. Clin. Microbiol., 2005, 43(7):3438-3442, Am. Society for Microbiology, USA.
Louie et al., "Rapid Detection of Methicillin-Resistant *Staphylococci* from Blood Culture Bottles by Using a Multiplex PCR Assay," J. Clin. Microbiol., 2002, 40(8):2786-2790, Am. Society for Microbiology, USA.
McClure et al., "Novel Multiplex PCR Assay for Detection of the Staphylococcal Virulence Marker Panton-Valentine Leukocidin Genes and Simultaneous Discrimination of Methicillin-Susceptible from Resistant *Staphylococci*," J. Clin. Microbiol., 2006, 44(3):1131-1144, Am. Society for Microbiology, USA.
Paule et al., Real-Time PCR Can Rapidly Detect Methicillin-Susceptible and Methicillin-Resistant *Staphylococcus aureus* Directly From Positive Blood Culture Bottles, Am. J. Clin. Pathol., 2005, 124:404-407, American Society of Clinical Pathologists, USA.
Sinsimer et al., "Use of a Multiplex Molecular Beacon Platform for Rapid Detection of Methicillin and Vancomycin Resistance in *Staphylococcus aureus*," J. Clin. Microbiol., 2005, 43:4585-4591, Am. Society for Microbiology, USA.
Thomas et al., "Development of a real-time *Staphylococcus aureus* and MRSA (SAM-) PCR for routine blood culture," J. Microbiol. Meth., 2007, 68:296-302, Elsevier, USA.
Volkmann et al., "Detection of clinically relevant antibiotic-resistance genes in municipal wastewater using real-time PCR (TaqMan)," J. Microbiol. Meths., 2004, 56:277-286, Elsevier, USA.
Wang et al., "Development and Evaluation of an Absolute qPCR Technique for Methicillin-Resistant *Staphylococcus aureus* (MRSA) in Ventilator Associated Pneumonia (VAP) by using Mini-bronchoalveolar Lavage (mini-BAL) Specimens," p. 130-S, J. Biomol. Tech., 2007, 18(1): 45-46, Association of Biomolecular Resource Facilities, USA.
Zhang et al., "New Quadriplex PCR Assay for Detection of Methicillin and Mupirocin Resistance and Simultaneous Discrimination of *Stapylococcus aureus* from Coagulase-Negative *Staphylococci*," J. Clin. Microbiol., 2004, 42 (11):4947-4955, Am. Society for Microbiology, USA.
JPO Office Action, Japanese Patent Application No. 2010-539916, Oct. 24, 2013.
APO Office Action, Australian Patent Application No. 2008345600, Jun. 7, 2013.

\* cited by examiner

*Primary Examiner* — Teresa E Strzelecka
*Assistant Examiner* — Joyce Tung
(74) *Attorney, Agent, or Firm* — Brian S. Sun; Charles B. Cappellari; Michael J. Gilly

(57) ABSTRACT

Method of detecting methicillin-resistant *S. aureus* (MRSA) and methicillin-sensitive *S. aureus* (MSSA) in a nucleic acid coamplification assay. The invention advantageously reduces the incidence of false-positive MRSA determinations in real-time assays by requiring satisfaction of a threshold criterion that excludes certain co-infections from the MRSA determination. The invention further provides for determination of MSSA, even when the MSSA is present in combination with methicillin-resistant coagulase-negative (MR-CoNS) bacteria at high or low levels.

12 Claims, 16 Drawing Sheets

SEQUENCE LISTING

```
<160> NUMBER OF SEQ ID NOS: 21

<210> SEQ ID NO 1
<211> LENGTH: 19
<212> TYPE: DNA
<213> ORGANISM: Staphylococcus aureus

<400> SEQUENCE: 1
tggggttgta ggacactct                                                 19

<210> SEQ ID NO 2
<211> LENGTH: 23
<212> TYPE: DNA
<213> ORGANISM: Staphylococcus aureus

<400> SEQUENCE: 2
gagaaagaaa attcgattcc ctt                                            23
```

```
<210> SEQ ID NO 3
<211> LENGTH: 26
<212> TYPE: DNA
<213> ORGANISM: Staphylococcus aureus
<220> FEATURE:
<221> NAME/KEY: misc_feature
<222> LOCATION: (1)..(3)
<223> OTHER INFORMATION: Locked nucleic acid nucleotide analogs
<220> FEATURE:
<221> NAME/KEY: misc_feature
<222> LOCATION: (6)..(6)
<223> OTHER INFORMATION: Locked nucleic acid nucleotide analogs
<220> FEATURE:
<221> NAME/KEY: misc_feature
<222> LOCATION: (9)..(10)
<223> OTHER INFORMATION: Locked nucleic acid nucleotide analogs
<220> FEATURE:
<221> NAME/KEY: misc_feature
<222> LOCATION: (17)..(18)
<223> OTHER INFORMATION: Locked nucleic acid nucleotide analogs
<220> FEATURE:
<221> NAME/KEY: misc_feature
<222> LOCATION: (25)..(25)
<223> OTHER INFORMATION: Locked nucleic acid nucleotide analogs
<220> FEATURE:
<221> NAME/KEY: misc_feature
<222> LOCATION: (26)..(26)
<223> OTHER INFORMATION: 3' OH blocked with reverse polarity C residue

<400> SEQUENCE: 3
ttgagtggat cctgagtacg acggag                                          26

<210> SEQ ID NO 4
<211> LENGTH: 60
<212> TYPE: DNA
<213> ORGANISM: Staphylococcus aureus
<220> FEATURE:
<221> NAME/KEY: promoter
<222> LOCATION: (1)..(27)
<220> FEATURE:
<221> NAME/KEY: misc_feature
<222> LOCATION: (60)..(60)
<223> OTHER INFORMATION: 3' OH blocked with inverted C residue

<400> SEQUENCE: 4
aatttaatac gactcactat agggagacca caacggtctc aagagagaca acattttcga     60

<210> SEQ ID NO 5
<211> LENGTH: 27
<212> TYPE: DNA
<213> ORGANISM: Staphylococcus aureus

<400> SEQUENCE: 5
gcaacgttca atttaattttt gttaaag                                        27

<210> SEQ ID NO 6
<211> LENGTH: 22
<212> TYPE: DNA
<213> ORGANISM: Staphylococcus aureus

<400> SEQUENCE: 6
gcaacgttca atttaattttt gt                                             22

<210> SEQ ID NO 7
<211> LENGTH: 23
<212> TYPE: DNA
<213> ORGANISM: Staphylococcus aureus

<400> SEQUENCE: 7
```

```
gcaacgttca atttaatttt gtt                                         23
```

<210> SEQ ID NO 8
<211> LENGTH: 34
<212> TYPE: DNA
<213> ORGANISM: Staphylococcus aureus

<400> SEQUENCE: 8

```
gcaacgttca atttaatttt gttaaagaag atgg                             34
```

<210> SEQ ID NO 9
<211> LENGTH: 36
<212> TYPE: DNA
<213> ORGANISM: Staphylococcus aureus

<400> SEQUENCE: 9

```
gcaacgttca atttaatttt gttaaagaag atggta                           36
```

<210> SEQ ID NO 10
<211> LENGTH: 23
<212> TYPE: DNA
<213> ORGANISM: Staphylococcus aureus

<400> SEQUENCE: 10

```
aacgagtaga tgctcaatat aaa                                         23
```

<210> SEQ ID NO 11
<211> LENGTH: 18
<212> TYPE: DNA
<213> ORGANISM: Staphylococcus aureus

<400> SEQUENCE: 11

```
caaactacgg taacattg                                               18
```

<210> SEQ ID NO 12
<211> LENGTH: 22
<212> TYPE: DNA
<213> ORGANISM: Staphylococcus aureus
<220> FEATURE:
<221> NAME/KEY: misc_feature
<222> LOCATION: (3)..(5)
<223> OTHER INFORMATION: Locked nucleic acid nucleotide analogs
<220> FEATURE:
<221> NAME/KEY: misc_feature
<222> LOCATION: (11)..(13)
<223> OTHER INFORMATION: Locked nucleic acid nucleotide analogs
<220> FEATURE:
<221> NAME/KEY: misc_feature
<222> LOCATION: (17)..(19)
<223> OTHER INFORMATION: Locked nucleic acid nucleotide analogs
<220> FEATURE:
<221> NAME/KEY: misc_feature
<222> LOCATION: (22)..(22)
<223> OTHER INFORMATION: 3' OH blocked with inverted C residue

<400> SEQUENCE: 12

```
agaccaaagc atacatattg aa                                          22
```

<210> SEQ ID NO 13
<211> LENGTH: 55
<212> TYPE: DNA
<213> ORGANISM: Staphylococcus aureus
<220> FEATURE:
<221> NAME/KEY: promoter
<222> LOCATION: (1)..(27)
<220> FEATURE:
<221> NAME/KEY: misc_feature
<222> LOCATION: (55)..(55)

```
<223> OTHER INFORMATION: 3' OH blocked with inverted C residue

<400> SEQUENCE: 13
aatttaatac gactcactat agggagatgg tctttctgca ttcctggaat aatga        55

<210> SEQ ID NO 14
<211> LENGTH: 24
<212> TYPE: DNA
<213> ORGANISM: Artificial sequence
<220> FEATURE:
<223> OTHER INFORMATION: Priming oligonucleotide for amplifying a
      synthetic internal control sequence

<400> SEQUENCE: 14
gaccatgtcc caattcgcac cagg                                          24

<210> SEQ ID NO 15
<211> LENGTH: 24
<212> TYPE: DNA
<213> ORGANISM: Artificial sequence
<220> FEATURE:
<223> OTHER INFORMATION: Displacer oligonucleotide for amplifying a
      synthetic internal control sequence

<400> SEQUENCE: 15
gcgatgattg acttgtgatt ccgc                                          24

<210> SEQ ID NO 16
<211> LENGTH: 21
<212> TYPE: DNA
<213> ORGANISM: Artificial Sequence
<220> FEATURE:
<223> OTHER INFORMATION: Terminating oligonucleotide for amplifying a
      synthetic internal control sequence
<220> FEATURE:
<221> NAME/KEY: misc_feature
<222> LOCATION: (5)..(7)
<223> OTHER INFORMATION: Locked nucleic acid nucleotide analogs
<220> FEATURE:
<221> NAME/KEY: misc_feature
<222> LOCATION: (11)..(13)
<223> OTHER INFORMATION: Locked nucleic acid nucleotide analogs
<220> FEATURE:
<221> NAME/KEY: misc_feature
<222> LOCATION: (17)..(19)
<223> OTHER INFORMATION: Locked nucleic acid nucleotide analogs
<220> FEATURE:
<221> NAME/KEY: misc_feature
<222> LOCATION: (21)..(21)
<223> OTHER INFORMATION: 3' OH blocked with inverted C residue

<400> SEQUENCE: 16
aatctattgt cacttccttg a                                             21

<210> SEQ ID NO 17
<211> LENGTH: 56
<212> TYPE: DNA
<213> ORGANISM: Artificial sequence
<220> FEATURE:
<223> OTHER INFORMATION: Promoter oligonucleotide for amplifying a
      synthetic internal control sequence
<220> FEATURE:
<221> NAME/KEY: promoter
<222> LOCATION: (1)..(27)
<220> FEATURE:
<221> NAME/KEY: misc_feature
<222> LOCATION: (56)..(56)
<223> OTHER INFORMATION: 3' OH blocked with inverted C residue

<400> SEQUENCE: 17
```

```
aatttaatac gactcactat agggagaaga ttatatagga cgacaagtaa aaatta        56
```

```
<210> SEQ ID NO 18
<211> LENGTH: 19
<212> TYPE: RNA
<213> ORGANISM: Staphylococcus aureus
<220> FEATURE:
<221> NAME/KEY: misc_feature
<222> LOCATION: (1)..(19)
<223> OTHER INFORMATION: 2' methoxy nucleotide analogs
<220> FEATURE:
<221> NAME/KEY: misc_feature
<222> LOCATION: (5)..(6)
<223> OTHER INFORMATION: nine carbon non-nucleotide spacer

<400> SEQUENCE: 18
caugucaaag gacgacaug                                                 19

<210> SEQ ID NO 19
<211> LENGTH: 20
<212> TYPE: RNA
<213> ORGANISM: Staphylococcus aureus
<220> FEATURE:
<221> NAME/KEY: misc_feature
<222> LOCATION: (1)..(20)
<223> OTHER INFORMATION: 2' methoxy nucleotide analogs
<220> FEATURE:
<221> NAME/KEY: misc_feature
<222> LOCATION: (5)..(6)
<223> OTHER INFORMATION: nine carbon non-nucleotide spacer

<400> SEQUENCE: 19
ccaauuggaa guuagauugg                                                20

<210> SEQ ID NO 20
<211> LENGTH: 22
<212> TYPE: RNA
<213> ORGANISM: Artificial sequence
<220> FEATURE:
<223> OTHER INFORMATION: Oligonucleotide probe for detecting a synthetic
      internal control sequence
<220> FEATURE:
<221> NAME/KEY: misc_feature
<222> LOCATION: (1)..(22)
<223> OTHER INFORMATION: 2' methoxy nucleotide analogs
<220> FEATURE:
<221> NAME/KEY: misc_feature
<222> LOCATION: (17)..(18)
<223> OTHER INFORMATION: nine carbon non-nucleotide spacer

<400> SEQUENCE: 20
ccacuugcga uguuuuaagu gg                                             22

<210> SEQ ID NO 21
<211> LENGTH: 51
<212> TYPE: DNA
<213> ORGANISM: Artificial sequence
<220> FEATURE:
<223> OTHER INFORMATION: Synthetic capture probe
<220> FEATURE:
<221> NAME/KEY: misc_feature
<222> LOCATION: (1)..(3)
<223> OTHER INFORMATION: Locked nucleic acid nucleotide analogs
<220> FEATURE:
<221> NAME/KEY: misc_feature
<222> LOCATION: (7)..(9)
<223> OTHER INFORMATION: Locked nucleic acid nucleotide analogs
<220> FEATURE:
<221> NAME/KEY: misc_feature
<222> LOCATION: (13)..(15)
<223> OTHER INFORMATION: Locked nucleic acid nucleotide analogs
<220> FEATURE:
```

```
<221> NAME/KEY: misc_feature
<222> LOCATION: (51)..(51)
<223> OTHER INFORMATION: 3' OH blocked with inverted C residue

<400> SEQUENCE: 21
kkkkkkkkkk kkkkkkkktt taaaaaaaaa aaaaaaaaaa aaaaaaaaaa a            51
```

DETECTION OF ANTIBIOTIC-RESISTANT MICROORGANISMS

RELATED APPLICATIONS

This application claims the benefit of U.S. Provisional Application No. 61/015,954, filed Dec. 21, 2007; and U.S. Provisional Application No. 61/041,146, filed Mar. 31, 2008. The entire disclosures of these earlier applications are hereby incorporated by reference.

FIELD OF THE INVENTION

The present invention relates to the sub-field of biotechnology that concerns nucleic acid diagnostics. More particularly, the invention relates to the detection of antibiotic-resistant organisms, such as methicillin-resistant *Staphylococcus aureus* (MRSA).

BACKGROUND OF THE INVENTION

Methicillin-resistant *Staphylococcus aureus* (MRSA) is a bacterial pathogen resistant to certain antibiotics that are otherwise effective against methicillin-sensitive *S. aureus* (MSSA). More specifically, strains of *S. aureus* that are oxacillin and methicillin resistant, historically termed MRSA, are resistant to all β-lactam agents, including cephalosporins and carbapenems. Hospital-associated MRSA isolates often are multiply resistant to other commonly used antimicrobial agents, including erythromycin, clindamycin, and tertacycline, while community-associated MRSA isolates are often resistant only to β-lactam agents and erythromycin. (See U.S. CDC publication, "Laboratory Detection of: Oxacillin/Methicillin-Resistant *Staphylococcus aureus*" (2005)) The estimated number of people developing a serious MRSA infection (i.e., invasive) in 2005 was about 94,360. (*JAMA* 298:1763-1771 (2007))

The magnitude of the MRSA problem is growing, and the human and economic tolls are rising. Indeed, approximately 32% of the U.S. population is already colonized with *S. aureus*, and approximately and 0.8% is already colonized MRSA. (Kuehnert et al., *J. Infect. Diseases* 193:172 (2006)) The proportion of healthcare-associated staphylococcal infections due to MRSA has also been increasing: 2% of *S. aureus* infections in U.S. intensive-care units were MRSA in 1974, 22% in 1995, and 64% in 2004. (Klevens et al., *Clin. Infect. Diseases* 42:389 (2006)) The evidence indicates that infections by MRSA and MSSA are associated with similar direct medical costs, but that MRSA infection is associated with more than double the rate of death when compared to infection by MSSA (i.e., 21% versus 8%). (Rubin et al., *Emerg. Infect. Diseases* 5:9 (1999)) Various diagnostic and screening assays that detect MRSA have been developed to support early intervention.

Although screening for MRSA colonization has traditionally relied on culture of specimens, for example using selective broth or agar medium, molecular approaches have been developed to speed the time to diagnosis. For example, Huletsky et al., in *J. Clin. Microbiol.* 42:1875 (2004) described a real-time PCR assay for detecting MRSA in specimens containing a mixture of staphylococci. The assay relied on detection of a mobile genetic element, designated the Staphylococcal Cassette Chromosome mec (SCCmec), integrated at the 3' end of an open reading frame of unknown function, termed "orfX." The SCCmec, which carries the mecA gene that confers drug-resistance in MRSA bacteria, is located at least 9 kb distant from the integration junction detected in the amplification reaction. The technique described by Huletsky et al., requires a collection of five primers that hybridize on one side of the SCCmec right extremity sequence, and one primer and three molecular beacon hybridization probes specific for the *S. aureus* chromosomal orfX gene. The requirement for numerous orfX primers reflects the known sequence divergence among different MRSA isolates. Alternative molecular assays independently detect a first gene sequence specific for *S. aureus*, and a second gene sequence specific for the mecA gene, but fail to establish physical linkage between the two sequences.

Published reports have highlighted certain deficiencies in each of the existing molecular approaches for MRSA detection. For example, Desjardins et al., in *J. Clin*, Microbiol. 44:1219 (2006) described results from procedures carried out using a commercial MRSA assay employing the junction-based amplification procedure for testing nasal specimens. Briefly, the authors noted the recovery of MSSA isolates from samples identified as being MRSA-positive in the real-time assay. This incidence of false-positive results might be explained by the presence of a junction in bacteria that have lost the mecA gene, for example as the result of genetic instability in the absence of antibiotic selective pressure. Moreover, our coworkers have observed that the same commercial assay failed to detect at least one highly drug resistant MRSA isolate, presumably because the junction sequences were highly diverged and did not hybridize amplification primers efficiently. The utility of the screening strategy is further confounded by the fact that the SCC junction is not uniquely associated with the methicillin resistance (see Becker et al., in *J. Clin. Microbiol,* 44:229 (2006), on page 231). Thus, the junction-based MRSA detection approaches are plagued by both false-positive and false-negative results.

Other molecular approaches for MRSA screening have been considered, but also suffer deficiencies. For example, Becker et al., in *J. Clin. Microbiol.* 44:229 (2006) questioned whether nasal colonization by both methicillin-resistant coagulase-negative staphylococci (MR-CoNS) and MSSA strains occur frequently enough to represent a risk of false-positive MRSA determinations by molecular methods. The authors showed that 3-4% of a sample population of patients admitted for hospital procedures showed evidence for nasal colonization by MSSA and MR-CoNS. Thus, samples from colonized individuals included both mecA DNA sequences, and *S. aureus*-specific DNA sequences. The study concluded that a molecular MRSA screening test independently targeting the mecA gene and a *S. aureus*-specific gene would be associated with an unacceptable positive predictive value of 40% when applied directly to clinical specimens in a low MRSA setting.

Existing approaches for MRSA screening ofcomplex samples, such as nasal swab samples, are prone to certain levels of erroneous assignments. Accordingly there remains a need for a rapid molecular approach that reduces false-positive MRSA assignments, particularly in instances of coinfection by *S. aureus* and methicillin-resistant bacteria other than *S. aureus* (e.g., MR-CoNS). The present invention answers this need.

SUMMARY OF THE INVENTION

A first aspect of the invention relates to a composition for amplifying a nucleic acid sequence encoding a *S. aureus*-specific target sequence. The invented composition includes a first oligonucleotide that has a target-complementary base sequence consisting of SEQ ID NO:1, and a second oligonucleotide up to 60 bases in length that has a target-complementary base sequence consisting of SEQ ID NO:4, optionally including a 5' sequence that is not complementary to the S. aureus-specific target sequence. In a preferred embodiment only one of the first and second oligonucleotides has a 3' end that can be extended by a template-dependent DNA polymerase. More preferably, the composition further includes a detectably labeled hybridization probe.

Another aspect of the invention relates to a composition for amplifying a nucleic acid sequence encoding methicillin resistance. The invented composition includes a first oligonucleotide that has a target-complementary base sequence selected from the group consisting of SEQ ID NO:5, SEQ ID NO:6, SEQ ID NO:7, SEQ ID NO:8, and SEQ ID NO:9. The composition also includes a second oligonucleotide that has a target-complementary base sequence consisting of SEQ ID NO:13, optionally including a 5' sequence that is not complementary to the nucleic acid sequence encoding methicillin resistance. In a preferred embodiment, only one of the first and second oligonucleotides has a 3' end that can be extended by a template-dependent DNA polymerase. More preferably, the composition further includes a detectably labeled hybridization probe.

Another aspect of the invention relates to a method of reducing the incidence of false-positive MRSA determinations in a nucleic acid coamplification assay that identifies MRSA by the presence of two amplified sequences. First there is a step for obtaining genomic DNA from a clinical sample to be tested for the presence of MRSA. In accordance with the invented method, this results in a mixture of S. aureus nucleic acids and nucleic acids encoding methicillin-resistance. Next, there is a step for coamplifying a S. aureus-specific target sequence and a methicillin resistance marker in an in vitro nucleic acid amplification reaction performed using as templates the obtained genomic DNA. This is followed by determining time-dependent indicia of amplification for the S. aureus-specific target sequence and for the methicillin resistance marker that coamplified. Next, there is a step for calculating a numerical value that is a function of both of the determined time-dependent indicia of amplification. Next, there is a step for comparing the calculated numerical value with a threshold criterion for identifying MRSA, wherein the threshold criterion excludes a subset of numerical values indicative of clinical samples including mixtures of MSSA and MR-CoNS bacteria, but not including MRSA bacteria. Finally, there is a step for determining that MRSA is present in the clinical sample only if the threshold criterion is met, whereby the incidence of false-positive MRSA determinations is reduced. In a preferred embodiment, the threshold criterion requires that the calculated numerical value is within a range that extends from an upper threshold cut-off value down to a lower threshold cut-off value. In a different preferred embodiment, the calculated numerical value is a numerical $\Delta Ct$ value calculated as a difference between the determined time-dependent indicia of amplification. More preferably, the threshold criterion requires that the numerical $\Delta Ct$ value is within a $\Delta Ct$ range that extends from an empirically determined upper threshold cut-off value down to an empirically determined lower threshold cut-off value. Still more preferably, the methicillin resistance marker includes a mecA target sequence, the numerical $\Delta Ct$ value is calculated by subtracting time-dependent indicia of amplification determined for the mecA target sequence from time-dependent indicia of amplification determined for the S. aureus-specific target sequence, and the threshold criterion requires that the numerical $\Delta Ct$ value is greater than an empirically determined threshold cut-off value. In accordance with a more general embodiment of the invention, the clinical sample is a nasal swab sample. In accordance with a different general embodiment of the invention, the methicillin resistance marker includes a mecA target sequence. In instances wherein the clinical sample is a nasal swab sample, it is preferred that the methicillin resistance marker includes a mecA target sequence. In a highly preferred embodiment, the S. aureus-specific target sequence includes a S. aureus-specific ribosomal nucleic acid sequence.

Another aspect of the invention relates to a method of establishing that a clinical sample contains methicillin-sensitive S. aureus (MSSA) bacteria. In general, the method includes a step for obtaining nucleic acids from the clinical sample. This may involve conventional procedures, such as treatment of the sample with detergent and alkali. Next, there is a step for coamplifying a S. aureus-specific target sequence and a target sequence specific for methicillin resistance in an in vitro nucleic acid amplification reaction. This reaction is performed using as templates the nucleic acids obtained in the earlier step of the procedure. The invented method is particularly used for working with samples wherein each of the two indicated target sequences is included among nucleic acids obtained in the initial obtaining step. Indeed, amplification products for both of the target sequences are produced and detected in the in vitro nucleic acid amplification reaction. This is followed by a step for determining time-dependent indicia of amplification for the S. aureus-specific target sequence and for the target sequence specific for methicillin resistance that coamplified. Next, there is a step for calculating a numerical value that is a function of both of the time-dependent indicia of amplification from the determining step. Next, there is a step for establishing that the biological sample contains methicillin-sensitive S. aureus bacteria if the calculated numerical value satisfies a threshold criterion. The threshold criterion distinguishes the coamplification kinetics of nucleic acids obtained from methicillin-resistant S. aureus bacteria, and from a mixture of methicillin-sensitive S. aureus bacteria and methicillin-resistant coagulase-negative bacteria. In one preferred embodiment, the clinical sample is a nasal swab sample. In another preferred embodiment, the target sequence specific for methicillin resistance includes a mecA target sequence. In still another preferred embodiment, the threshold criterion involves comparison of the calculated numerical value with an empirically determined lower threshold cut-off value, and also with an empirically determined upper threshold cut-off value. In yet another preferred embodiment, the calculated numerical value is a numerical $\Delta Ct$ value that is calculated as a difference between the determined time-dependent indicia of amplification. More preferably, the threshold criterion requires either that the numerical $\Delta Ct$ value is less than an empirically determined lower threshold cut-off value, or that the numerical $\Delta Ct$ value is greater than an empirically determined upper threshold cut-off value in order to establish the presence of methicillin-sensitive S. aureus bacteria. Alternatively, the numerical $\Delta Ct$ value can be calculated by subtracting the time-dependent indicia of amplification determined for the mecA target sequence from the time-dependent indicia of amplification determined the S. aureus-specific target sequence. Further, the threshold criterion requires that the numerical $\Delta Ct$ value is less than an empirically determined threshold cut-off value to establish the presence of methicillin-sensitive S. aureus bacteria. In accordance with a different alternative, the numerical $\Delta Ct$ value can be calculated by subtracting the time-dependent indicia of amplification determined for the mecA target sequence from the time-dependent indicia of amplification determined the S. aureus-specific target sequence. Further, the threshold criterion requires that the numerical $\Delta Ct$ value is greater than an empirically determined threshold cut-off value to establish the presence of methicillin-sensitive *S. aureus* bacteria. In yet another preferred embodiment, the obtaining step involves obtaining genomic DNA. In still yet another preferred embodiment, the in vitro nucleic acid amplification reaction includes a reverse transcriptase enzyme. In still yet another preferred embodiment, the *S. aureus*-specific target sequence is a *S. aureus* ribosomal nucleic acid sequence. In still yet another preferred embodiment, the determining step involves determining the time at which a predetermined level of a detectable signal indicative of amplicon production is achieved. In accordance with more general embodiments of the invention, when the clinical sample is a nasal swab sample, it is preferred that the target sequence specific for methicillin resistance includes a mecA target sequence. When this is the case, the calculated numerical value preferably is a numerical ΔCt value calculated as a difference between the time-dependent indicia of amplification in the determining step. According to one preferred alternative, the threshold criterion involves comparison of the numerical ΔCt value with an empirically determined lower threshold cut-off value and with an empirically determined upper threshold cut-off value. According to another preferred alternative, the threshold criterion requires either that the numerical ΔCt value is less than an empirically determined lower threshold cut-off value, or that the numerical ΔCt value is greater than an empirically determined upper threshold cut-off value to establish the presence of methicillin-sensitive *S. aureus* bacteria. According to still another preferred alternative, the numerical ΔCt value is calculated by subtracting the time-dependent indicia of amplification determined for the mecA target sequence from the time-dependent indicia of amplification determined the *S. aureus*-specific target sequence, and the threshold criterion requires that the numerical ΔCt value is less than an empirically determined threshold cut-off value to establish the presence of methicillin-sensitive *S. aureus* bacteria. According to still yet another preferred alternative, the numerical ΔCt value is calculated by subtracting the time-dependent indicia of amplification determined for the mecA target sequence from the time-dependent indicia of amplification determined the *S. aureus*-specific target sequence, and the threshold criterion requires that the numerical ΔCt value is greater than an empirically determined threshold cut-off value to establish the presence of methicillin-sensitive *S. aureus* bacteria.

Another aspect of the invention relates to a method of designating, with a controllable incidence of false-positive determinations, that a clinical sample contains methicillin-resistant *S. aureus* (MRSA) bacteria. The method begins with a step for obtaining genomic DNA from the clinical sample, whereby there results a mixture of *S. aureus* nucleic acids and nucleic acids encoding methicillin-resistance. This is followed by a step for coamplifying a *S. aureus*-specific target sequence and a methicillin resistance marker in an in vitro nucleic acid amplification reaction using as templates the obtained genomic DNA. Next, there is a step for determining time-dependent indicia of amplification for the *S. aureus*-specific target sequence, and for the methicillin resistance marker that coamplified. Next, there is a step for calculating a numerical value that is a function of both of the determined time-dependent indicia of amplification. Finally, there is a step for designating that the clinical sample contains MRSA if the calculated numerical value satisfies a threshold criterion that distinguishes amplification of nucleic acids obtained from MRSA from amplification of nucleic acids obtained from mixtures of MSSA and MR-CoNS bacteria. It follows from this procedure that false-positive MRSA determinations resulting from mixtures of MSSA and MR-CoNS in the clinical sample are reduced compared with methods that determine the presence of MRSA simply by qualitatively detecting both the *S. aureus*-specific target sequence and the methicillin resistance marker. In one preferred embodiment, the threshold criterion requires that the calculated numerical value is within a range that extends from an empirically determined upper threshold cut-off value down to an empirically determined lower threshold cut-off value. In a different preferred embodiment, the calculated numerical value is a numerical ΔCt value calculated as a difference between the determined time-dependent indicia of amplification. More preferably, the threshold criterion requires that the numerical ΔCt value is within a ΔCt range that extends from an empirically determined upper threshold cut-off value down to an empirically determined lower threshold cut-off value. According to a more general embodiment of the invention, the clinical sample is a nasal swab sample. According to a different general embodiment, the methicillin resistance marker includes a mecA target sequence. In accordance with embodiments wherein the clinical sample is a nasal swab sample, the methicillin resistance marker includes a mecA target sequence. In a highly preferred embodiment, the *S. aureus*-specific target sequence includes a ribosomal nucleic acid sequence.

Another aspect of the invention relates to a method of establishing whether a clinical sample contains methicillin-resistant *S. aureus* (MRSA) bacteria or a mixture of methicillin-sensitive *S. aureus* (MSSA) bacteria and methicillin-resistant coagulase-negative *staphylococcus* (MR-CoNS) bacteria. The method begins with a step for obtaining genomic DNA from the clinical sample, whereby there results a mixture of *S. aureus* nucleic acids and nucleic acids encoding methicillin-resistance. Next, there is a step for coamplifying a *S. aureus*-specific target sequence and a methicillin resistance marker in an in vitro nucleic acid amplification reaction that is performed using as templates the obtained genomic DNA. This is followed by a step for determining time-dependent indicia of amplification for the *S. aureus*-specific target sequence and for the methicillin resistance marker that coamplified. Next, there is a step for calculating a numerical value that is a function of both of the time-dependent indicia of amplification. Finally, there is a step for establishing which of the following two mutually exclusive conditions exists. In the first case, the clinical sample contains MRSA if the calculated numerical value satisfies a threshold criterion that distinguishes coamplification kinetics of nucleic acids obtained from MRSA bacteria and nucleic acids obtained from mixtures of MSSA and MR-CoNS bacteria. In the second case, the clinical sample contains MSSA mixed with MR-CoNS, and does not contain MRSA if the calculated numerical value does not satisfy the threshold criterion. In one preferred embodiment, the threshold criterion requires that the numerical value is within a range that extends from an empirically determined upper threshold cut-off value down to an empirically determined lower threshold cut-off value. In a different preferred embodiment, the numerical value calculated in step (d) is a numerical ΔCt value that is calculated as a difference between the determined time-dependent indicia of amplification determined in step (c). More preferably, the threshold criterion requires that the numerical ΔCt value is within a ΔCt range that extends from an empirically determined upper threshold cut-off value down to an empirically determined lower threshold cut-off value. Still more preferably, the numerical ΔCt value is lower than the empirically determined lower threshold cut-off value, thereby indicating that the clinical sample contains a mixture of MSSA bacteria and MR-CoNS bacteria, where the MSSA bacteria is present in a greater amount than the MR-CoNS bacteria. In accordance with a more general embodiment of the invention, the clinical sample is a nasal swab sample. In accordance with a different general embodiment of the invention, the methicillin resistance marker includes a mecA target sequence. In instances wherein the clinical sample is a nasal swab sample, the methicillin resistance marker preferably includes a mecA target sequence. When this is the case, the S. aureus-specific target sequence can be a ribosomal nucleic acid sequence.

Another aspect of the invention relates to a method of setting sensitivity and specificity parameters in a real-time nucleic acid coamplification assay that identifies kinetic profiles consistent with the presence of MRSA bacteria in a clinical test sample. The method begins with a step for obtaining a collection of clinical samples known to include MRSA bacteria, and a collection of clinical samples known to include MSSA and MR-CoNS, but not MRSA bacteria. This is followed by a step for isolating genomic DNA from each sample among the collections of clinical samples, whereby there results a collection of isolated genomic DNA samples from bacteria including MRSA, and a collection of isolated genomic DNA samples from bacteria including MSSA and MR-CoNS, but not MRSA. Next, there is a step for coamplifying, in separate nucleic acid amplification reactions for each of the isolated genomic DNA samples, a S. aureus-specific target sequence and a methicillin resistance marker. Next, there is a step for determining time-dependent indicia of amplification for the S. aureus-specific target sequence and for the methicillin resistance marker that coamplified in the nucleic acid amplification reactions. Next, there is a step for calculating, for each of the nucleic acid amplification reactions, a numerical value that is a function of both of the time-dependent indicia of amplification determined in the earlier step. This results in a collection of numerical values for samples including MRSA, and a collection of numerical values for samples including MSSA and MR-CoNS, but not MRSA. Finally, there is a step for selecting a threshold criterion for the calculated numerical value that is required for identifying kinetic profiles consistent with the presence of MRSA bacteria in the clinical test sample. The threshold criterion excludes a subset of values among the collection of numerical values for samples including MSSA and MR-CoNS, but not MRSA. This amounts to setting sensitivity and specificity parameters in the real-time nucleic acid coamplification assay. In a preferred embodiment, the subset of values excluded by the threshold criterion includes the highest and lowest values among the collection of numerical values for samples including MSSA and MR-CoNS, but not MRSA. In a different preferred embodiment, there is a further step for changing the selected threshold criterion, thereby modifying sensitivity and specificity parameters of the real-time nucleic acid coamplification assay.

DEFINITIONS

The following terms have the indicated meanings in the specification unless expressly indicated to have a different meaning.

By "sample" or "test sample" is meant any substance suspected of containing a target organism or nucleic acid derived from the target organism. The substance may be, for example, an unprocessed clinical specimen, such as a nasal swab specimen, a buffered medium containing the specimen, a medium containing the specimen and lytic agents for releasing nucleic acid belonging to the target organism, or a medium containing nucleic acid derived from the target organism which has been isolated and/or purified in a reaction receptacle or on a reaction material or device.

By "derived" is meant that the referred to nucleic acid is obtained directly from an organism or is the product of a nucleic acid amplification. Thus, a nucleic acid that is derived from an organism may be, for example, an antisense RNA molecule which does not naturally exist in the organism.

"Sample preparation" refers to any steps or methods that prepare a sample for subsequent amplification and detection of nucleic acids present in the sample. Sample preparation may include any known method of liberating or concentrating components from a larger sample volume or from a substantially aqueous mixture. Sample preparation may include lysis of cellular components and removal of debris, may include denaturation of double-stranded nucleic acids, and may include use of nucleic acid oligomers to selectively capture the target nucleic acid from other sample components.

By "lyse" or "lysis" is meant, with reference to a cell, to cause to be in an altered state permitting nucleic acid to be released therefrom.

By "isolate" or "isolating" is meant that at least a portion of the target nucleic acid present in a test sample is concentrated within a reaction receptacle or on a reaction device or solid carrier (e.g., test tube, cuvette, microtiter plate well, nitrocellulose filter, slide or pipette tip) in a fixed or releasable manner so that the target nucleic acid can be purified without significant loss of the target nucleic acid from the receptacle, device or carrier.

By "separating" or "purifying" is meant that one or more components of the biological sample are removed from one or more other components of the sample. Sample components include nucleic acids in a generally aqueous solution phase which may also include materials such as proteins, carbohydrates, lipids and labeled probes. Preferably, the separating or purifying step removes at least about 70%, more preferably at least about 90% and, even more preferably, at least about 95% of the other components present in the sample.

"Nucleic acid" refers to a multimeric compound comprising nucleosides or nucleoside analogs which have nitrogenous heterocyclic bases, or base analogs, which are linked by phosphodiester bonds or other linkages to form a polynucleotide. Nucleic acids include RNA, DNA, or chimeric DNA-RNA polymers, and analogs thereof. A nucleic acid "backbone" may be made up of a variety of linkages, including one or more of sugar-phosphodiester linkages, peptide-nucleic acid (PNA) bonds (PCT No. WO 95/32305), phosphorothioate linkages, methylphosphonate linkages, or combinations thereof. Sugar moieties of the nucleic acid may be either ribose or deoxyribose, or similar compounds having known substitutions, such as 2' methoxy substitutions and 2' halide substitutions (e.g., 2'-F). Nitrogenous bases may be conventional bases (A, G, C, T, U), analogs thereof (e.g., inosine), derivatives of purine or pyrimidine bases, such as $N^4$-methyl deoxygaunosine, deaza- or aza-purines, deaza- or aza-pyrimidines, pyrimidine bases having substituent groups at the 5 or 6 position, purine bases having an altered or replacement substituent at the 2, 6 and/or 8 position, such as 2-amino-6-methylaminopurine, $O^6$-methylguanine, 4-thio-pyrimidines, 4-amino-pyrimidines, 4-dimethylhydrazine-pyrimidines, and $O^4$-alkyl-pyrimidines, and pyrazolo-compounds, such as unsubstituted or 3-substituted pyrazolo[3,4-d]pyrimidine (U.S. Pat. Nos. 5,378,825, 6,949,367 and PCT No. WO 93/13121). Nucleic acids may include "abasic" positions in which the backbone does not include a nitrogenous base for one or more residues (see U.S. Pat. No. 5,585,481). Nucleic acids also include "locked nucleic acids" (LNA), an analog containing one or more LNA nucleotide monomers with a bicyclic furanose unit locked in an RNA mimicking sugar conformation (Vester et al., 2004, *Biochemistry* 43(42): 13233-41). A nucleic acid may comprise only conventional sugars, bases, and linkages as found in RNA and DNA, or may include conventional components and substitutions (e.g., conventional bases linked by a 2' methoxy backbone, or a nucleic acid including a mixture of conventional bases and one or more base analogs). Methods for synthesizing nucleic acids in vitro are well known in the art.

By "oligonucleotide" or "oligomer" is meant a polymer made up of two or more nucleoside subunits or nucleobase subunits coupled together. Oligonucleotides preferably have a length in the range of from 10-100 nucleotides, more preferably 10-80 nucleotides, and still more preferably from 15-60 nucleotides. The oligonucleotide may be DNA and/or RNA and analogs thereof. The sugar groups of the nucleoside subunits may be ribose, deoxyribose and analogs thereof, including, for example, ribonucleosides having a 2'-O-methylsubstitution to the ribofuranosyl moiety. Oligonucleotides including nucleoside subunits having 2' substitutions and which are useful as detection probes, capture oligos and/or amplification oligonucleotides are disclosed by Becker et al., in U.S. Pat. No. 6,130,038. The nucleoside subunits may be joined by linkages such as phosphodiester linkages, modified linkages, or by non-nucleotide moieties which do not prevent hybridization of the oligonucleotide to its complementary target nucleic acid sequence. Modified linkages include those linkages in which a standard phosphodiester linkage is replaced with a different linkage, such as a phosphorothioate linkage or a methylphosphonate linkage. The nucleobase subunits may be joined, for example, by replacing the natural deoxyribose phosphate backbone of DNA with a pseudo-peptide backbone, such as a 2-aminoethylglycine backbone which couples the nucleobase subunits by means of a carboxymethyl linker to the central secondary amine. (DNA analogs having a pseudo-peptide backbone are commonly referred to as "peptide nucleic acids" or "PNA", and are disclosed by Nielsen et al., "Peptide Nucleic Acids," U.S. Pat. No. 5,539,082.) Other non-limiting examples of oligonucleotides or oligomers contemplated by the present invention include nucleic acid analogs containing bicyclic and tricyclic nucleoside and nucleotide analogs referred to as "Locked Nucleic Acids," "Locked Nucleoside Analogues" or "LNA." (Locked Nucleic Acids are disclosed by Wang, "Conformationally Locked Nucleosides and Oligonucleotides," U.S. Pat. No. 6,083,482; Imanishi et al., "Bicyclonucleoside and Oligonucleotide Analogues," U.S. Pat. No. 6,268,490; and Wengel et al., "Oligonucleotide Analogues," U.S. Pat. No. 6,670,461.) Any nucleic acid analog is contemplated by the present invention, provided that the modified oligonucleotide can hybridize to a target nucleic acid under either stringent hybridization conditions or amplification reaction conditions.

An "amplification oligonucleotide" or the equivalent "amplification oligomer" is an oligonucleotide that hybridizes to a target nucleic acid, or its complement, and participates in a nucleic acid amplification reaction. An example of an amplification oligonucleotide is a "primer" that hybridizes to a template nucleic acid and contains a 3' hydroxyl end that is extended by a polymerase in an amplification process. Another example is an oligonucleotide that participates in or facilitates amplification but is not extended by a polymerase, for example because it has a 3' blocked end. Preferred size ranges for amplification oligonucleotides include those that are about 10 to about 60 nt long and contain at least about 10 contiguous bases, and more preferably at least 12 contiguous bases that are complementary to a region of the target nucleic acid sequence (or its complementary sequence). The contiguous bases are preferably at least 80%, more preferably at least 90%, and most preferably about 100% complementary to the target sequence to which the amplification oligonucleotide binds. An amplification oligonucleotide may optionally include modified nucleotides or analogs, or optionally an additional sequence that participate in an amplification reaction but are not complementary to or contained in or complementary to the target or template sequence. For example, a "promoter primer" is an amplification oligonucleotide that includes a 5' promoter sequence that is non-complementary to the target nucleic acid but is adjacent or near to the complementary sequence of the primer. Those skilled in the art will understand that an amplification oligonucleotide that functions as a primer may be modified to include a 5' promoter sequence, and thus function as a promoter-primer, and a promoter-primer can function as a primer independent of its promoter sequence (i.e., the oligonucleotide may be modified by removal of, or synthesis without, its promoter sequence). An amplification oligonucleotide referred to equivalently as a "promoter provider" or "promoter oligonucleotide" includes a promoter sequence that serves as a template for polymerization but the oligonucleotide is not extended from its 3' end which is blocked and, therefore, not available for extension by a DNA polymerase activity.

By "substantially homologous," "substantially corresponding," or "substantially corresponds" is meant that the subject oligonucleotide has a base sequence containing an at least 10 contiguous base region that is at least 80% homologous, preferably at least 90% homologous, and most preferably 100% homologous to an at least 10 contiguous base region present in a reference base sequence (excluding RNA and DNA equivalents). Those skilled in the art will readily appreciate modifications that could be made to the hybridization assay conditions at various percentages of homology to permit hybridization of the oligonucleotide to the target sequence while preventing unacceptable levels of non-specific hybridization. The degree of similarity is determined by comparing the order of nucleobases making up the two sequences and does not take into consideration other structural differences that may exist between the two sequences, provided the structural differences do not prevent hydrogen bonding with complementary bases. The degree of homology between two sequences can also be expressed in terms of the number of base mismatches present in each set of at least 10 contiguous bases being compared, which may range from 0 to 2 base differences.

By "substantially complementary" is meant that the subject oligonucleotide has a base sequence containing an at least 10 contiguous base region that is at least 70% complementary, preferably at least 80% complementary, more preferably at least 90% complementary, and most preferably 100% complementary to an at least 10 contiguous base region present in a target nucleic acid sequence (excluding RNA and DNA equivalents). The degree of complementarity is determined by comparing the order of bases making up the two sequences and does not take into consideration other structural differences which may exist between the two sequences, provided the structural differences do not prevent hydrogen bonding with complementary bases. The degree of complementarity between two sequences can also be expressed in terms of the number of base mismatches present in each set of at least 10 contiguous bases being compared, which may range from 0-3 base mismatches.

As used herein, "amplification" or "amplifying" refers to an in vitro procedure for obtaining multiple copies of a target nucleic acid sequence, its complement or fragments thereof.

For example, an in vitro amplification reaction is an enzyme-catalyzed reaction that results in the synthesis of multiple copies of a target nucleic acid sequence, its complement or fragments thereof. Examples of amplification methods that can be used for preparing in vitro amplification reactions are given below. An "isothermal" in vitro amplification reaction is an in vitro amplification reaction that synthesizes multiple copies of a target nucleic acid sequence, its complement or fragments thereof at a constant temperature (i.e., without thermal cycling). Preferred in vitro amplification reactions synthesize amplicons in an exponential fashion, meaning that one amplicon serves as the template for production of new amplicons.

As used herein, monitoring amplicon production "as a function of time" refers to the process of taking periodic measurements of the amount of amplicon present in an in vitro amplification reaction, and associating that measured amount with an elapsed reaction time. For example, periodic measurements can be taken at the same point of different cycles of an amplification reaction, or at periodic time intervals (such as every 20 seconds) during a reaction that does not involve physical cycling of reaction steps.

As used herein, the phrase "indicia of amplification" refers to features of real-time run curves which indicate a predetermined level of progress in nucleic acid amplification reactions. Such indicia are commonly determined by mathematical analysis of run curves, sometimes referred to as "growth curves," which display a measurable signal (such as a fluorescence reading) whose intensity is related to the quantity of an amplicon present in a reaction mixture as a function of time, cycle number, etc.

By "target nucleic acid" or "target" is meant a nucleic acid molecule containing a target nucleic acid sequence.

By "target nucleic acid sequence" or "target sequence" or "target region" is meant a specific deoxyribonucleotide or ribonucleotide sequence comprising all or part of the nucleotide sequence of a single-stranded nucleic acid molecule, and possibly comprising (when specified) the deoxyribonucleotide or ribonucleotide sequence complementary thereto. In general, a target nucleic acid sequence that is to be amplified will be positioned between two oppositely disposed amplification oligonucleotides, and will include the portion of the target nucleic acid molecule that is partially or fully complementary to each of the amplification oligonucleotides. In the context of the invention, a target nucleic acid molecule may be, for example, a ribosomal nucleic acid molecule or a mecA nucleic acid molecule. The portion of the target nucleic acid molecule to be amplified in an in vitro nucleic acid amplification reaction would be referred to as the "target nucleic acid sequence" to be amplified.

As used herein, by "methicillin resistance marker" or "target sequence specific for methicillin resistance" or "methicillin resistance target" is meant a nucleic acid sequence present in methicillin-resistant bacteria, but absent from bacteria that are sensitive to growth inhibition by methicillin. An example methicillin resistance marker is the mecA nucleic acid sequence detected in the nucleic acid amplification reaction described herein.

As used herein, a "*S. aureus*-specific" target sequence is a nucleic acid sequence that is present in *S. aureus* bacteria, but absent from CoNS bacteria. Preferably, the *S. aureus*-specific target sequence also is absent from bacteria in the genus *Enterococcus*. Still more preferably, the *S. aureus*-specific target sequence is unique to *S. aureus* when compared with sequences found in other Gram(+) bacteria. An example *S. aureus*-specific target sequence is the 23S rDNA sequence detected in the nucleic acid amplification reaction described herein. Other *S. aureus*-specific target sequences will be known to those having an ordinary level of skill in the art.

As used herein, the "target-hybridizing sequence" of a hybridization probe or an amplification oligonucleotide refers to the base sequence of the probe or amplification oligonucleotide which participates in a duplex structure upon hybridization to an appropriate target nucleic acid. In the case of a promoter-provider that includes a downstream sequence complementary to the target nucleic acid and an upstream T7 promoter sequence which is not complementary to the target nucleic acid, the non-complementary promoter sequence of the amplification oligonucleotide would not be considered a target-hybridizing sequence. Conversely, a downstream primer sequence sufficiently complementary to the target nucleic acid to be able to form a duplex structure upon hybridization to the target nucleic acid would be a target-hybridizing sequence. If the target-hybridizing sequence of the primer contains occasional mismatches to the target nucleic acid sequence, then it would not be fully complementary to the target nucleic acid sequence within the target nucleic acid molecule.

By "fully complementary" is meant 100% base complementarity between two nucleic acid molecules over the length of the target-hybridizing sequence.

By "amplicon" or "amplification product" is meant a nucleic acid molecule generated in a nucleic acid amplification reaction. An amplicon or amplification product contains a target nucleic acid sequence that may be of the same or opposite sense as the target nucleic acid.

By "amplification conditions" is meant conditions permitting nucleic acid amplification. Acceptable amplification conditions could be readily ascertained without the exercise of anything more than routine experimentation by someone having ordinary skill in the art depending on the particular method of amplification employed. Exemplary amplification conditions are given herein.

By "transcription-associated amplification" is meant any type of nucleic acid amplification that uses an RNA polymerase to produce multiple RNA transcripts from a nucleic acid template. Conventionally, these amplification reactions employ at least one primer having a 3'-end that can be extended by the activity of a DNA polymerase. One example of a transcription-associated amplification method, called "Transcription Mediated Amplification" (TMA), generally employs an RNA polymerase, a DNA polymerase, deoxyribonucleoside triphosphates, ribonucleoside triphosphates, and a promoter-containing oligonucleotide complementary to the target nucleic acid. Variations of TMA are well known in the art as disclosed in detail in Burg et al., U.S. Pat. No. 5,437,990; Kacian et al., U.S. Pat. Nos. 5,399,491 and 5,554,516; Kacian et al., PCT No. WO 93/22461; Gingeras et al., PCT No. WO 88/01302; Gingeras et al., PCT No. WO 88/10315; Malek et al., U.S. Pat. No. 5,130,238; Urdea et al., U.S. Pat. Nos. 4,868,105 and 5,124,246; McDonough et al., PCT No. WO 94/03472; and Ryder et al., PCT No. WO 95/03430. Other transcription-associated amplification methods employing only a single primer that can be extended by a DNA polymerase, as disclosed in the U.S. patent application Ser. No. 11/213,519 are particularly embraced by the definition and are highly preferred for use in connection with the method disclosed herein.

By "hybridization" or "hybridize" is meant the ability of two completely or partially complementary nucleic acid strands to come together under specified hybridization assay conditions to form a stable structure having a double-stranded region. The two constituent strands of this double-stranded structure, sometimes called a "hybrid," are held together by hydrogen bonds. Although these hydrogen bonds most commonly form between nucleotides containing the bases adenine and thymine or uracil (A and T or U) or cytosine and guanine (C and G) on single nucleic acid strands, base pairing can also form between bases which are not members of these "canonical" pairs. Non-canonical base pairing is well-known in the art.

As used herein, a "hybridization probe" is an oligonucleotide that hybridizes specifically to a target sequence in a nucleic acid, preferably in an amplified nucleic acid, under conditions that promote hybridization, to form a detectable hybrid. A probe optionally may contain a detectable moiety which either may be attached to the end(s) of the probe or may be internal. The nucleotides of the probe which combine with the target polynucleotide need not be strictly contiguous, as may be the case with a detectable moiety internal to the sequence of the probe. Detection may either be direct (i.e., resulting from a probe hybridizing directly to the target sequence or amplified nucleic acid) or indirect (i.e., resulting from a probe hybridizing to an intermediate molecular structure that links the probe to the target sequence or amplified nucleic acid). The "target" of a probe generally refers to a sequence contained within an amplified nucleic acid sequence which hybridizes specifically to at least a portion of a probe oligonucleotide using standard hydrogen bonding (i.e., base pairing). A probe may comprise target-specific sequences and optionally other sequences that are non-complementary to the target sequence that is to be detected. These non-complementary sequences may comprise a promoter sequence, a restriction endonuclease recognition site, or sequences that contribute to three-dimensional conformation of the probe (e.g., described in U.S. Pat. Nos. 5,118,801, 5,312,728, U.S. Pat. Nos. 6,849,412, 6,835,542, 6,534,274, and 6,361,945 and US 2006-0068417 A1). Sequences that are "sufficiently complementary" allow stable hybridization of a probe oligonucleotide to a target sequence that is not completely complementary to the probe's target-specific sequence.

By "sufficiently complementary" is meant a contiguous sequence that is capable of hybridizing to another sequence by hydrogen bonding between a series of complementary bases, which may be complementary at each position in the sequence by standard base pairing (e.g., G:C, A:T or A:U pairing) or may contain one or more positions, including abasic ones, which are not Complementary bases by standard hydrogen bonding. Contiguous bases are at least 80%, preferably at least 90%, and more preferably about 100% complementary to a sequence to which an oligomer is intended to specifically hybridize. Sequences that are "sufficiently complementary" allow stable hybridization of a nucleic acid oligomer to its target sequence under the selected hybridization conditions, even if the sequences are not completely complementary. Appropriate hybridization conditions are well known in the art, can be predicted readily based on base sequence composition, or can be determined by using routine testing (e.g., Sambrook et al., *Molecular Cloning, A Laboratory Manual*, 2$^{nd}$ ed. (Cold Spring Harbor Laboratory Press, Cold Spring Harbor, N.Y., 1989), §§1.90-1.91, 7.37-7.57, 9.47-9.51 and 11.47-11.57, particularly at §§9.50-9.51, 11.12-11.13, 11.45-11.47 and 11.55-11.57).

By "antisense," "opposite sense," or "negative sense" is meant a nucleic acid molecule perfectly complementary to a reference, or sense, nucleic acid molecule.

By "sense," "same-sense," or "positive sense" is meant a nucleic acid molecule perfectly homologous to a reference nucleic acid molecule.

By "RNA and DNA equivalents" is meant RNA and DNA molecules having the same complementary base pair hybridization properties. RNA and DNA equivalents have different sugar moieties (i.e., ribose versus deoxyribose) and may differ by the presence of uracil in RNA and thymine in DNA. The differences between RNA and DNA equivalents do not contribute to differences in homology because the equivalents have the same degree of complementarity to a particular sequence.

By "nucleic acid duplex," "duplex," "nucleic acid hybrid" or "hybrid" is meant a stable nucleic acid structure comprising a double-stranded, hydrogen-bonded region. Such hybrids include RNA:RNA, RNA:DNA and DNA:DNA duplex molecules and analogs thereof. The structure is sufficiently stable to be detectable by any known means, including means that do not require a probe associated label.

By "capture oligonucleotide" is meant an oligonucleotide that is capable of binding to a target nucleic acid (preferably in a region other than that targeted by a detection probe) and, either directly or indirectly, to a solid support, thereby providing means for immobilizing and isolating the target nucleic acid in a test sample. The capture oligo includes a target binding region that hybridizes to the target nucleic acid, and an immobilized probe binding region that hybridizes to an immobilized probe bound to a solid support. The target binding and immobilized probe binding regions may be contained within the same oligonucleotide, directly adjoining each other or separated by one or more optionally modified nucleotides, or these regions may be joined to each other by means of a non-nucleotide linker. The target binding region that hybridizes to the target nucleic acid may do so by sequence-specific or non-specific mechanisms.

By "immobilized probe" or "immobilized nucleic acid" is meant an oligonucleotide for joining a capture oligonucleotide to an immobilized support. The immobilized probe is joined either directly or indirectly to the solid support by a linkage or interaction which remains stable under the conditions employed to hybridize the capture probe to the target nucleic acid and to the immobilized probe, whether those conditions are the same or different. The immobilized probe facilitates separation of the bound target nucleic acid from unbound materials in a sample.

As used herein, a "detectable label" is a chemical species that can be detected or can lead to a detectable response. Detectable labels in accordance with the invention can be linked to polynucleotide probes either directly or indirectly, and include radioisotopes, enzymes, haptens, chromophores such as dyes or particles that impart a detectable color (e.g., latex beads or metal particles), luminescent compounds (e.g., bioluminescent, phosphorescent or chemiluminescent moieties) and fluorescent compounds.

A "homogeneous detectable label" refers to a label that can be detected in a homogeneous fashion by determining whether the label is on a probe hybridized to a target sequence. That is, homogeneous detectable labels can be detected without physically removing hybridized from unhybridized forms of the label or labeled probe. Homogeneous detectable labels are preferred when using labeled probes for detecting nucleic acids. Examples of homogeneous labels have been described in detail by Arnold et al., U.S. Pat. No. 5,283,174; Woodhead et al., U.S. Pat. No. 5,656,207; and Nelson et al., U.S. Pat. No. 5,658,737. Preferred labels for use in homogenous assays include chemiluminescent compounds (e.g., see Woodhead et al., U.S. Pat. No. 5,656,207; Nelson et al., U.S. Pat. No. 5,658,737; and Arnold, Jr., et al., U.S. Pat. No. 5,639,604). Preferred chemiluminescent labels are acridinium ester ("AE") compounds, such as standard AE or derivatives thereof (e.g., naphthyl-AE, ortho-AE, 1- or 3-methyl-AE, 2,7-dimethyl-AE, 4,5-dimethyl-AE, ortho-dibromo-AE, ortho-dimethyl-AE, meta-dimethyl-AE, ortho-methoxy-AE, ortho-methoxy(cinnamyl)-AE, ortho-methyl-AE, ortho-fluoro-AE, 1- or 3-methyl-ortho-fluoro-AE, 1- or 3-methyl-meta-difluoro-AE, and 2-methyl-AE).

A "homogeneous assay" refers to a detection procedure that does not require physical separation of hybridized probe from non-hybridized probe prior to determining the extent of specific probe hybridization. Exemplary homogeneous assays, such as those described herein, can employ molecular torches, molecular beacons or other self-reporting probes which have a stem-and-loop structure and emit fluorescent signals when hybridized to an appropriate target, chemiluminescent acridinium ester labels which can be selectively destroyed by chemical means unless present in a hybrid duplex, and other homogeneously detectable labels that will be familiar to those having an ordinary level of skill in the art.

By "stringent hybridization conditions," or "stringent conditions" is meant conditions permitting a detection probe to preferentially hybridize to a target nucleic acid and not to a non-target nucleic. Stringent hybridization conditions may vary depending upon factors including the GC content and length of the probe, the degree of similarity between the probe sequence and sequences of non-target sequences which may be present in the test sample, and the target sequence. Hybridization conditions include the temperature and the composition of the hybridization reagents or solutions. Preferred hybridization assay conditions for detecting target nucleic acids with the probes of the present invention correspond to a temperature of about 60° C. when the salt concentration is in the range of about 0.6-0.9 M. Specific hybridization assay conditions are set forth in the Examples section. Other acceptable stringent hybridization conditions could be easily ascertained by those having ordinary skill in the art.

By "assay conditions" is meant conditions permitting stable hybridization of an oligonucleotide to a target nucleic acid. For example, real-time format amplification allows that probe hybridization and detection can occur under the same assay conditions used for conducting the nucleic acid amplification reaction. Example amplification assay conditions that permit both amplification of a target and hybridization of a probe to an amplicon are given herein.

As used herein, "acceptance criteria" define in measurable terms what must be true for a real-time nucleic acid amplification reaction to be judged as indicating a particular target nucleic acid has been amplified. For example, a fluorescent signal indicating the presence of an amplicon may be monitored as a function of time, and may be used for establishing indicia of amplification based on analysis of a real-time run curve. The acceptance criteria may require that the fluorescent signal exceed a threshold value within a predetermined time frame to be considered positive. Alternatively, the acceptance criteria may require production of a minimum fluorescent signal, in combination with indicia of amplification meeting certain preset requirements (e.g., the measured indicia must fall within a particular time window).

As used herein, a "false-positive" result is one wherein a truly negative sample is falsely identified as positive. For example, a truly MRSA-negative sample identified as being MRSA-positive would be a false-positive result.

As used herein, a "false-negative" result is one wherein a truly positive sample is falsely identified as negative. For example, a truly MRSA-positive sample identified as being MRSA-negative would be a false-negative result.

As used herein, a "look-up table" refers to a collection of data representing possible combinations of positive and negative amplification results associated with $\Delta Ct$ values expressed relative to (e.g., < or 24) a threshold value. Each combination in the collection is associated with an interpretation that assigns positive or negative status to an organism type. A look-up table can be stored on computer-readable media, and conventionally is used for decoding experimental results to provide an organism identification.

In the context of the invention, certain methods are used for making or outputting a diagnostic determination. For example, based on a set of data there will be a conclusion that the likelihood of a particular organism being present is very high. An output result of the method can indicated as a step for "determining" or "assigning" or "establishing" or "calling" that a particular organism is present, or perhaps absent. It is to be understood that all diagnostic assays are associated with levels of false-positive and false-negative results. One feature of the invented method relates to an approach for controlling the balance between these, as may be reflected by assay sensitivity and specificity.

By "consists essentially of" or "consisting essentially of," when used with reference to an oligonucleotide herein, is meant that the oligonucleotide has a base sequence substantially homologous to a specified base sequence and may have up to four additional bases and/or two bases deleted therefrom. Thus, these phrases contain both a sequence length limitation and a sequence variation limitation. Any additions or deletions are non-material variations of the specified base sequence which do not prevent the oligonucleotide from having its claimed property, such as being able to preferentially hybridize under stringent hybridization conditions to its target nucleic acid over non-target nucleic acids. The oligonucleotide may contain a base sequence substantially similar to a specified nucleic acid sequence without any additions or deletions. However, a probe or primer containing an oligonucleotide consisting essentially of a specified base sequence may include other nucleic acid molecules which do not participate in hybridization of the probe to the target nucleic acid and which do not affect such hybridization.

DESCRIPTION OF THE PREFERRED EMBODIMENTS

Figure 1A:
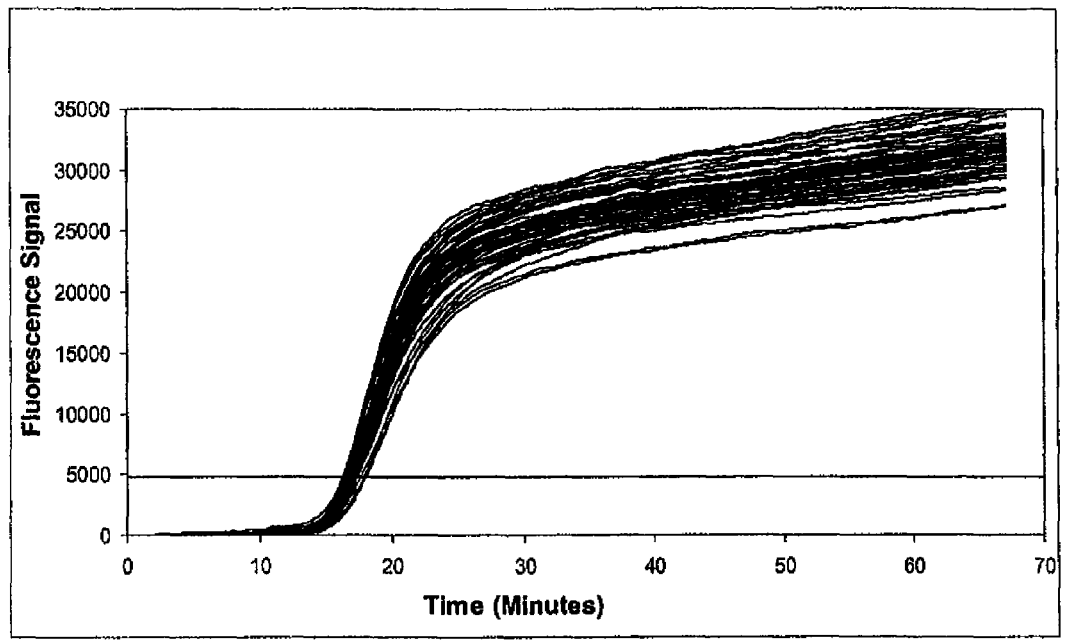
FIGS. 1A-1B are graphical presentations of real-time run curves for amplification of the S. aureus marker (panel A) and of the mecA marker (panel B) in reactions preformed using 160 CFU of MRSA and 100,000 CFU each of S. epidermidis and S. haemolyticus bacteria. The vertical axes show fluorescent signals, measured in RFU, for 52 amplification reactions. The horizontal lines drawn at 5,000 RFU (panel A) and at 2,500 RFU (panel B) on the vertical axes represent partial criteria used for determining positive amplification results.

Generally speaking, the invention relates to methods of detecting the genetic signature of an organism in a test sample. In a preferred embodiment, the test sample is a clinical sample obtained from a single individual (i.e., as distinguished from pooled clinical samples obtained from multiple individuals). The clinical sample may comprise a mixed population of organisms, as may be obtained when an individual co-infected with two or more organisms. In accordance with a different preferred embodiment, the sample undergoing testing can be a pooled sample prepared by first combining clinical samples obtained from a plurality of individuals. Of course, the invented methods also can be applied to the analysis of a cultured sample representing only a single type of organism.

The invented method preferably is carried out by detecting the presence of two genetic markers (i.e., nucleic acid sequences "A" and "B"), where those markers are present in a particular ratio that is characteristic of an organism or a physiological condition. The particular ratio can be a fixed ratio. For example, the two markers may be present on a single chromosome of a bacterial cell so that the copy number of the markers, and so the ratio of one to the other, is constant. Alternatively, the two markers may be present on different chromosomes in a single cell of an organism and still exhibit a fixed ratio in cells of that organism. The genetic marker may be present in DNA obtained from the clinical sample (e.g., a bacterial DNA sample), or may be present in RNA obtained from the clinical sample.

The disclosed threshold-based approach for analyzing real-time run curves offers certain advantages over prior systems and approaches. Indeed, the approach can distinguish a sample containing an organism having both genetic markers (i.e., A/B) from a mixture of two different types organism, where each type separately contributes only one marker (i.e., A+B). Moreover, the approach also can detect the presence of an organism having both genetic markers (i.e., A/B), even when mixed with another organism having only one of the two markers (e.g., B only). For example, the technique can be used for detecting the presence of a species-specific marker (e.g., a ribosomal nucleic acid sequence) and an antibiotic-resistance marker to detect a particular species of antibiotic resistant bacteria. A particular example of antibiotic resistant bacteria that can be detected by the disclosed method is MRSA. As the method is practiced, it is possible to distinguish a sample of MRSA from a sample that contains both MSSA and MR-CoNS bacteria. Moreover, the MRSA bacteria can be detected in the presence of methicillin resistant bacteria other than *S. aureus* (e.g., MR-CoNS bacteria).

There also is flexibility in the manner of performing the amplification reactions of the invention. In one embodiment, two nucleic acid targets used for identifying the organism are amplified independently (i.e., in amplification reactions not in fluid communication with each other). Indicia of amplification can be determined for each of the different targets, and those indicia used for assessing the presence or absence of an organism. In a different embodiment, a multiplex amplification reaction is performed wherein the two nucleic acid targets are coamplified in a single amplification reaction. One advantage of the multiplex amplification format is the potential for enhancing the measurable ΔCt difference relative to the ΔCt that would be determined using independent amplification reactions. This enhancement may result when the reactions that amplify the two nucleic acid targets compete for shared resources (e.g., ribonucleotide triphosphates, primers, and the like). Notably, the organism identification made by the technique disclosed herein is based on a threshold cutoff that avoids the need for quantifying the number of copies of each target nucleic acid.

Particularly disclosed are nucleic acid-based methods, compositions, algorithms, systems and kits for detecting MRSA and MSSA bacteria. The invention is illustrated using multiplex isothermal amplification reactions, where amplicon synthesis was monitored as a function of time as the reaction was occurring (i.e., in a real-time format). The nucleic acid marker for methicillin-resistance was a mecA nucleic acid sequence. The nucleic acid marker for *S. aureus* was a 23S ribosomal DNA sequence unique to that organism.

In contrast to the accepted practice in the field, the invention detects both MRSA and MSSA bacteria by detecting two different nucleic acid target sequences and employs an threshold-based algorithm for misinterpretations that characterize other screening systems based on detection of two targets. Moreover, the disclosed approach advantageously detected a highly drug-resistant MRSA isolate that was missed by a commercial MRSA screening kit based on detection of an SCCmec insertion junction. Thus, the invention provides a solution to the problem of being able to detect a wide range of MRSA isolates without being confounded by mixed populations of organisms representing co-infection by one organism that carries a marker specific for *S. aureus*, and a second marker specific for methicillin resistance.

Introduction and Overview

Below there are described example methods for preparing, amplifying and detecting nucleic acids of MRSA and MSSA bacteria. More particularly, there are disclosed methods for determining the presence of MRSA bacteria in environmental or biological samples by detecting the combination of a mecA nucleic acid sequence and a *S. aureus* ribosomal nucleic acid sequence. The technique advantageously detected MRSA among high backgrounds of methicillin-sensitive CoNS bacteria (i.e., *Staphylococcus epidermidis* and *Staphylococcus haemolyticus*), and among high backgrounds of MSSA. Additionally, the technique advantageously detected MSSA among high backgrounds of methicillin-sensitive CoNS bacteria (i.e., *S. epidermidis* and *S. haemotyticus*). Although independent amplification reactions for the mecA and *S. aureus* ribosomal nucleic acid sequences are contemplated, and are within the scope of the invention, it is preferred to amplify and detect this combination of nucleic acid sequences in a single multiplex nucleic acid amplification reaction (i.e., in a single reaction tube or vessel). Using akinetic analysis of real-time amplification results, it was possible to distinguish MRSA infection from a co-infection of MSSA (i.e., providing a source of *S. aureus* sequences) and MR-CoNS (i.e., providing a source of mecA sequences), and distinguish MSSA from MR-CoNS or MRSA using clinical samples.

Preferred methods include performing a nucleic acid amplification reaction and detecting amplified products, typically by using nucleic acid probes that specifically hybridize to the amplified products to provide detectable signals indicating the presence of mecA and *S. aureus* ribosomal nucleic acids in a test sample. The amplification step preferably includes contacting the sample with one or more amplification oligonucleotides specific for a target sequence in 23S rDNA to produce an amplified product if *S. aureus* rDNA is present in the sample. Although there may be independent reactions for amplifying ribosomal and mecA target nucleic acids, the amplification step preferably further includes contacting the sample with one or more amplification oligonucleotides specific for a mecA target DNA to produce an amplified product if the sample contains a methicillin resistant organism. When both the mecA target sequence and *S. aureus* ribosomal nucleic acid sequences are detected, the presence of MRSA can be deduced by kinetic analysis of the amplification reactions monitored as a function of time.

Particularly disclosed are selected oligonucleotide sequences that recognize target sequences of 23S rDNA and mecA DNA, including complementary sequences. Such oligonucleotides may function as amplification oligonucleotides (e.g., as priming oligonucleotides, promoter oligonucleotides, terminating oligonucleotides, and promoter primer oligonucleotides. It is also contemplated that oligonucleotides having the sequences disclosed herein could serve alternative functions in assays for detecting analyte nucleic acids. For example, the capture oligonucleotides disclosed herein could serve as hybridization probes, the hybridization probes disclosed herein could be used as amplification oligonucleotides, and the amplification oligonucleotides disclosed herein could be used as hybridization probes in alternative detection assays.

Preferred amplification reactions synthesize multiple copies of the target sequence or its complement by using at least one nucleic acid polymerase to extend an amplification oligonucleotide (e.g., a primer) in a template-dependent fashion. Preferred embodiments for detecting the amplified product involve contacting the amplified product with at least one probe specific for an amplified sequence (e.g., a sequence contained in the target sequence, or the complement thereof, that is flanked by a pair of amplification oligonucleotides). The detecting step may be performed after the amplification reaction is completed (i.e., sometimes referred to as "end point" detection), or may be performed concurrently with the amplification reaction in a format referred to as "real-time" amplification. In preferred embodiments, the amplified product is detected using a probe detectable in a homogeneous reaction. Examples of homogeneous detection of nucleic acids are given in U.S. Pat. Nos. 5,639,604 and 5,283,174. In preferred embodiments that detect the amplified product near or at the end of the amplification step, a probe hybridizes to the amplified product to provide a signal indicating hybridization of the probe to the amplified sequence. In other preferred embodiments that use real-time detection, the probe preferably includes a reporter moiety that provides the detected signal when the probe binds to the amplified product. For example, the probe may include a detectable moiety or label, such as a fluorophore, attached to one end of the probe and an interacting moiety, such as quencher, attached to the opposite end of a stem-and-loop structure to inhibit signal production when the stem structure is in the "closed" conformation and not hybridized to the amplified product. When the probe is hybridized to a complementary sequence, the probe is converted to an "open" conformation able to produce a detectable signal. Specific examples of preferred probes include a molecular torch, a molecular beacon, and a hybridization switch probe (e.g., U.S. Pat. Nos. 5,118,801 and 5,312,728, Lizardi et al., U.S. Pat. Nos. 5,925,517 and 6,150,097, Tyagi et al., U.S. Pat. Nos. 6,849,412, 6,835,542, 6,534,274, and 6,361,945, Becker et al., U.S. Ser. No. 11/173,915, Becker et al., and U.S. Pub. No. 2006-0194240 A1, Arnold Jr. et al.).

Useful Sample Preparation Techniques

Generally speaking, preferred methods of preparing samples for use in the disclosed amplification procedures involve collecting and then lysing samples of bacteria to release genomic DNA, and then denaturing the genomic DNA at least partially. The methods may include procedures for separating and/or concentrating organisms contained in a sample from other sample components (e.g., filtration of particulate matter from the samples) prior to the lysis step. Sample preparation may include chemical, mechanical, and/or enzymatic disruption of cells to release intracellular contents, including DNA encoding the 23S rRNA and mecA genes. Certain preferred methods for lysing bacteria, releasing genomic DNA, and capturing the released genomic DNA onto a solid support include an optional heating step. More preferably, the optional heating step is omitted, and the entire sample preparation procedure, including bacterial lysis, release of genomic DNA, and capture of genomic DNA onto a solid support is carried out at room temperature. Although enzymes, such as lysostaphin, may be used for sample preparation, highly preferred procedures do not employ enzymes. A step for target capture prior to nucleic acid amplification may specifically or non-specifically separate the target nucleic acids from other sample components based on the nucleic acid sequence of the target. Nonspecific target preparation methods may selectively precipitate nucleic acids from a substantially aqueous mixture, adhere nucleic acids to a support that is washed to remove other sample components, or use other means to physically separate nucleic acids from a mixture that contains other components. In certain embodiments, the captured nucleic acids are released from the solid support prior to amplification. In other embodiments, the captured nucleic acids are amplified without first being released from the solid support.

Nucleic acids can be isolated from test samples by various different approaches. Preferably, an alkaline lysis protocol is employed, optionally including an enzyme to aid in the lysis. One version of the alkaline lysis procedure is detailed by Sambrook et al., *Molecular Cloning. A Laboratory Manual*, 2nd ed. (Cold Spring Harbor Laboratory Press, Cold Spring Harbor, N.Y., 1989) under §§1.25-1.28. Preferred alkaline solutions can include strong bases, such as NaOH, LiOH, and the like. Detergents useful in the alkaline lysis procedure may be anionic detergents, non-ionic detergents, zwitterionic detergents, or cationic detergents. Of these, the anionic detergents are the most preferred. Strong anionic detergents, including sulfates of alkyl alcohols and N-acyl-amino acids are highly preferred. While the precise nature of the detergent used for the sample preparation procedure is not believed critical, examples of particularly preferred detergents include sodium dodecyl sulfate (SDS), and lithium lauryl sulfate (LLS). It is highly preferred to carry out the sample preparation procedure at ambient room temperature. The particular method of isolating nucleic acids to be used in the procedures described herein is not believed critical.

Preferably, nucleic acids are isolated from clinical samples, such as swab samples. This generally involved transferring the tip of a collection swab to a disposable plastic reaction tube, adding to the tube a volume of a buffered EDTA solution, and then vortexing to suspend any cellular material. An aliquot of the suspension typically was mixed with a volume of lysis buffer that included lithium lauryl sulfate and LiOH, and the mixture then vortexed briefly. Following a brief incubation at room temperature, the mixture was neutralized by adding a volume of HEPES-buffered solution containing a capture probe and magnetic beads displaying oligo(dT). Nucleic acids from the neutralized mixture were captured and washed using a KINGFISHER96 platform (Thermo Fisher Scientific, Inc.; Waltham, Mass.) prior to use as templates in nucleic acid amplification reactions.

Useful Amplification Methods

Amplification methods useful in connection with the present invention include: Transcription Mediated Amplification (TMA), Nucleic Acid Sequence-Based Amplification (NASBA), the Polymerase Chain Reaction (PCR), Strand Displacement Amplification (SDA), and amplification methods using self-replicating polynucleotide molecules and replication enzymes such as MDV-1 RNA and Q-beta enzyme. Methods for carrying out these various amplification techniques respectively can be found in U.S. Pat. No. 5,399,491, U.S. Pat. No. 5,554,517, U.S. Pat. No. 4,965,188, U.S. Pat. No. 5,455,166, U.S. Pat. No. 5,472,840 and Lizardi et al., *BioTechnology* 6:1197 (1988). Preferably, the target nucleic acid containing the sequence to be amplified is provided to the amplification reaction mixture as single-stranded nucleic acid, or at least partially single-stranded nucleic acid.

In one preferred embodiment of the invention, nucleic acid sequences are amplified using a TMA protocol. According to this protocol, the reverse transcriptase which provides the DNA polymerase activity also possesses an endogenous RNase H activity. One of the primers used in this procedure contains a promoter sequence positioned upstream of a sequence that is complementary to one strand of a target nucleic acid that is to be amplified. In the first step of the amplification, a promoter-primer hybridizes to the target DNA at a defined site. Reverse transcriptase creates a first complementary DNA copy of the target DNA by extension from the 3' end of the promoter-primer. A displacer oligonucleotide then hybridizes to the target DNA strand, and also is extended by the reverse transcriptase enzyme, thereby separating the first complementary DNA copy of the target DNA from the target DNA template. Following interaction of an opposite strand primer with the first complementary DNA strand, a second strand of DNA (i.e., having the same polarity as the original target DNA template) is synthesized by reverse transcriptase-mediated extension of the primer, thereby creating a double-stranded DNA molecule. RNA polymerase recognizes the double-stranded promoter sequence and initiates transcription. Each of the newly synthesized RNA amplicons re-enters the TMA process and serves as a template for a new round of replication, thereby leading to an exponential expansion of the RNA amplicon. The entire process is autocatalytic and is performed at a constant temperature.

In another preferred embodiment of the invention, a different transcription associated amplification method uses one primer and one or more additional amplification oligonucleotides to amplify nucleic acids in vitro by making transcripts that indicate the presence of the target nucleic acid in a sample. This method has been described in detail by Becker et al., in U.S. 2006-0046265 A1. Briefly, this method uses a primer or "priming oligomer," a "promoter oligonucteotide" that is modified to prevent synthetic extension from its 3' end (e.g., by including a 3'-blocking moiety) and, optionally, a 3'-blocked "terminating oligo" to terminate elongation of a cDNA from the target strand at a defined 3'-end. This method includes the steps of binding the target DNA that contains the target sequence with a priming oligo and a terminating oligonucleotide. The priming oligo hybridizes to the 3' end of the target strand and enzymatic RT activity initiates primer extension from the 3' end of the priming oligo to produce a cDNA, thereby creating a duplex of the new cDNA strand and the target DNA strand (i.e., a cDNA:DNA duplex). The terminating oligomer hybridizes to the target strand adjacent to the 5' end of the target sequence to be amplified. When the priming oligonucleotide is extended by the DNA polymerase activity of RT to produce the cDNA strand, polymerization stops when the primer extension product reaches the terminating oligonucleotide hybridized to the target strand and, thus, the 3' end of the cDNA is determined by the position of the terminating oligonucleotide on the target strand, making the 3' end of the cDNA complementary to the 5' end of the target sequence. The cDNA strand of the duplex is separated from the template strand, for example by denaturation or displacement by extension of a displacer oligonucleotide. Next, the promoter oligonucleotide hybridizes to the cDNA strand near its 3' end. The promoter oligonucleotide includes a 5' promoter sequence, a 3' region complementary to a sequence in the 3' region of the cDNA, and a modified 3' end that includes a blocking moiety to prevent initiation of DNA synthesis from its 3' end. In the duplex that includes the promoter oligonucleotide and the cDNA strand, the 3'-end of the cDNA is extended by the DNA polymerase activity of the RT enzyme, using the promoter oligonucleotide as a template to create a functional double-stranded promoter. An RNA polymerase specific for the functional promoter sequence then binds to the promoter and transcribes RNA transcripts complementary to the cDNA which are substantially identical to the target region sequence that was amplified from the initial target strand. The amplified RNA transcripts then serve as substrates in the amplification process by hybridizing to the priming oligonucleotide and serving as templates for further cDNA production.

Structural Features of Amplification Oligonucleotides

Promoter Oligonucleotides

As is well known in the art, a promoter is a specific nucleic acid sequence that is recognized by a DNA-dependent RNA polymerase as a signal to bind to the nucleic acid and initiate RNA transcription at a specific site. The template nucleic acid (the sequence to be transcribed) need not be double-stranded. Individual DNA-dependent RNA polymerases recognize a variety of different promoter sequences, which can vary markedly in their efficiency in promoting transcription. When an RNA polymerase binds to a promoter sequence to initiate transcription, that promoter sequence is not part of the sequence transcribed. Thus, the RNA transcripts produced thereby will not include that sequence.

According to the present invention, a "promoter oligonucleotide" refers to an oligonucleotide comprising first and second regions, and which is preferably modified to prevent the initiation of DNA synthesis from its 3'-terminus. The "first region" of a promoter oligonucleotide of the present invention comprises a base sequence which hybridizes to a DNA template, where the hybridizing sequence is situated 3', but not necessarily adjacent to, a promoter region. The hybridizing portion of a promoter oligonucleotide of the present invention is typically at least 10 nucleotides in length, and may extend up to 15, 20, 25, 30, 35, 40, 50 or more nucleotides in length. The "second region" comprises a promoter for an RNA polymerase. A promoter oligonucleotide of the present invention is engineered so that it is incapable of extension by a DNA polymerase (e.g., reverse transcriptase), and preferably comprises a blocking moiety at its 3'-terminus. Suitable and preferred promoter oligonucleotides are described herein.

Priming Oligonucleotide

A priming oligonucleotide is an oligonucleotide, at least the 3'-end of which is complementary to a nucleic acid template, and which hybridizes with the template to give a primer:template complex suitable for initiation of synthesis by a DNA polymerase. A priming oligonucleotide is extended by the addition of nucleotides to its 3'-terminus in a template-dependent manner. The result is a primer extension product. A priming oligonucleotide of the present invention is typically at least 10 nucleotides in length, and may extend up to 15, 20, 25, 30, 35, 40, 50 or more nucleotides in length. Suitable and preferred priming oligonucleotides are described herein. Virtually all DNA polymerases (including reverse transcriptases) that are known require complexing of an oligonucleotide to a single-stranded template ("priming") to initiate DNA synthesis, whereas RNA transcription (copying of RNA from DNA) generally does not require a primer. By its very nature of being extended by a DNA polymerase, a priming oligonucleotide does not comprise a 3'-blocking moiety.

Displacer Oligonucleotide

A "displacer oligonucleotide" is a priming oligonucleotide which hybridizes to a template nucleic acid upstream from a neighboring priming oligonucleotide hybridized to the 3'-end of a target sequence (referred to herein as the "forward priming oligonucleotide"). By "upstream" is meant that a 3'-end of the displacer oligonucleotide complexes with the template nucleic acid 5' to a 3'-end of the forward priming oligonucleotide. When hybridized to the template nucleic acid, the 3'-terminal base of the displacer oligonucleotide is preferably adjacent to or spaced apart from the 5-terminal base of the forward priming oligonucleotide. More preferably, the 3'-terminal base of the displacer oligonucleotide is spaced from 5 to 35 bases from the 5'-terminal base of the forward priming oligonucleotide. The displacer oligonucleotide may be provided to a reaction mixture contemporaneously with the forward priming oligonucleotide or after the forward priming oligonucleotide has had sufficient time to hybridize to the template nucleic acid. Extension of the forward priming oligonucleotide can be initiated prior to or after the displacer oligonucleotide is provided to a reaction mixture. Under amplification conditions, the displacer oligonucleotide is extended in a template-dependent manner, thereby displacing a primer extension product comprising the forward priming oligonucleotide which is complexed with the template nucleic acid. Once displaced from the template nucleic acid, the primer extension product comprising the forward priming oligonucleotide is available for complexing with a promoter oligonucleotide. The forward priming oligonucleotide and the displacer oligonucleotide both preferentially hybridize to the target nucleic acid. Examples of displacer oligonucleotides and their uses are disclosed by Becker et al., in U.S. patent application Ser. No. 11/681,104.

Blocking Moiety

Preferably, oligomers that are not extended by a nucleic acid polymerase include a "blocking moiety" that replaces the 3' OH to prevent enzyme-mediated extension of the oligomer in an amplification reaction. As used herein, a blocking moiety is a substance used to "block" the 3'-terminus of an oligonucleotide or other nucleic acid so that it cannot be efficiently extended by a nucleic acid polymerase. A blocking moiety may be a small molecule (e.g., a phosphate or ammonium group), or it may be a modified nucleotide (e.g., a 3'2' dideoxynucleotide or 3' deoxyadenosine 5'-triphosphate (cordycepin)), or other modified nucleotide. Additional blocking moieties include, for example, a nucleotide or a short nucleotide sequence having a 3'-to-5' orientation, so that there is no free hydroxyl group at the 3'-terminus, a 3' alkyl group, a 3' non-nucleotide moiety (see, Arnold et al., "Non-Nucleotide Linking Reagents for Nucleotide Probes," U.S. Pat. No. 6,031,091), phosphorothioate, alkane-diol residues, peptide nucleic acid (PNA), nucleotide residues lacking a 3' hydroxyl group at the 3'-terminus, or a nucleic acid binding protein. Preferably, the 3'-blocking moiety comprises a nucleotide or a nucleotide sequence having a 3'-to-5' orientation or a 3' non-nucleotide moiety, and not a 3'2'-dideoxynucleotide or a 3' terminus having a free hydroxyl group. Additional methods to prepare 3'-blocking oligonucleotides are well known to those of ordinary skill in the art.

Terminating Oligonucleotide

A "terminating oligonucleotide" is an oligonucleotide comprising a base sequence that is complementary to a region of the target nucleic acid in the vicinity of the 5'-end of the target sequence, so as to "terminate" primer extension of a nascent nucleic acid that includes a priming oligonucleotide, thereby providing a defined 3'-end for the nascent nucleic acid strand. A terminating oligonucleotide is designed to hybridize to the target nucleic acid at a position sufficient to achieve the desired 3'-end for the nascent nucleic acid strand. The positioning of the terminating oligonucleotide is flexible depending upon its design. A terminating oligonucleotide may be modified or unmodified. In certain embodiments, terminating oligonucleotides are synthesized with at least one or more LNA nucleotide analogs. These modified nucleotides have demonstrated higher thermal stability of complementary duplexes that include DNA. Other modifications, such as 2'-O-ME ribonucleotides, also may be utilized in certain embodiments. A terminating oligonucleotide of the present invention typically includes a blocking moiety at its 3'-terminus to prevent extension. A terminating oligonucleotide of the present invention is typically at least 10 bases in length, and may extend up to 15, 20, 25, 30, 35, 40, 50 or more nucleotides in length. Suitable and preferred terminating oligonucleotides are described herein. It should be noted that while a terminating oligonucleotide typically or necessarily includes a 3'-blocking moiety, "3'-blocked" oligonucleotides are not necessarily terminating oligonucleotides.

Useful Probes and Labeling Systems

Nucleic acid amplification products of the type disclosed herein can be detected by any conventional means. For example, amplification products can be detected by hybridization with a detectably labeled probe and measurement of the resulting hybrids. Design criteria in selecting probes for detecting particular target sequences are well known in the art and are described in, for example, Hogan et al., "Methods for Making Oligonucleotide Probes for the Detection and/or Quantitation of Non-Viral Organisms," U.S. Pat. No. 6,150, 517. Hogan teaches that probes should be designed to maximize homology for the target sequence(s) and minimize homology for possible non-target sequences. To minimize stability with non-target sequences, Hogan instructs that guanine and cytosine rich regions should be avoided, that the probe should span as many destabilizing mismatches as possible, and that the length of perfect complementarity to a non-target sequence should be minimized. Stability of the probe with the target sequence(s) should be maximized, adenine and thymine rich regions should be avoided, probe: target hybrids are preferably terminated with guanine and cytosine base pairs, extensive self-complementarity is generally to be avoided, and the melting temperature of probe: target hybrids should be about 2-10° C. higher than the assay temperature.

Certain probes that are preferred for detecting analyte nucleic acid sequences as disclosed herein have a probe sequence, which includes the target-complementary sequence of bases together with any base sequences that are not complementary to the nucleic acid that is to be detected, in the length range of from 10-100 nucleotides. Certain specific probes that are preferred for detecting the amplified analyte nucleic acid sequences have target-complementary sequences in the length range of from 10-50, from 10-20, or from 10-15 nucleotides. Of course, these target-complementary sequences may be linear sequences, or may be contained in the structure of a molecular torch, molecular beacon or other construct having one or more optional nucleic acid sequences that are non-complementary to the analyte target sequence that is to be detected. Probes may be made of DNA, RNA, a combination of DNA and RNA, a nucleic acid analog, or contain one or more modified nucleosides (e.g., a ribonucleoside having a 2'-O-methyl substitution to the ribofuranosyl moiety).

In a particular embodiment, an amplification product can be assayed by the Homogenous Protection Assay ("HPA"), which involves hybridizing a chemiluminescent oligonucleotide probe to the target sequence (e.g., an acridinium ester-labeled ("AE") probe), selectively hydrolyzing the chemiluminescent label present on unhybridized probe, and measuring the chemiluminescence produced from the remaining probe in a luminometer. The HPA assay technique has been detailed by Arnold et al., in U.S. Pat. No. 5,283,174.

In further embodiments, the present invention provides evaluation of the amplification process in real-time by methods described herein. Evaluation of an amplification process in "real-time" involves determining the amount of amplicon in the reaction mixture either continuously or periodically during the amplification reaction. The determined values can be used to calculate the amount of target sequence initially present in the sample. A variety of methods are available for determining the amount of initial target sequence present in a sample based on real-time amplification. These include those disclosed by Wittwer et al., "Method for Quantification of an Analyte," U.S. Pat. No. 6,303,305, and Yokoyama et al., "Method for Assaying Nucleic Acid," U.S. Pat. No. 6,541, 205. Another method for determining the quantity of target sequence initially present in a sample, but which is not based on a real-time amplification, is disclosed by Ryder et al., "Method for Determining Pre-Amplification Levels of a Nucleic Acid Target Sequence from Post-Amplification Levels of Product," U.S. Pat. No. 5,710,029. Amplification products may be detected in real-time through the use of various self-hybridizing probes, most of which have a stem-loop structure. Such self-hybridizing probes are labeled so that they emit differentially detectable signals, depending on whether the probes are in a self-hybridized state or hybridized to a target sequence.

By way of example, "molecular torches" are a type of self-hybridizing probe that includes distinct regions of self-complementarity (referred to as "the target binding domain" and "the target closing domain") which are connected by a joining region (e.g., non-nucleotide linker) and which hybridize to each other under predetermined hybridization assay conditions. In a preferred embodiment, molecular torches contain single-stranded base regions in the target binding domain that are from 1 to about 20 bases in length and are accessible for hybridization to a target sequence present in an amplification product under strand displacement conditions. Under strand displacement conditions, hybridization of the two complementary regions (which may be fully or partially complementary) of the molecular torch is favored, except in the presence of the target sequence, which will bind to the single-stranded region present in the target binding domain and displace all or a portion of the target closing domain. The target binding domain and the target closing domain of a molecular torch include a detectable label or a pair of interacting labels (e.g., luminescent/quencher) positioned so that a different signal is produced when the molecular torch is self-hybridized than when the molecular torch is hybridized to the target sequence, thereby permitting detection of probe:target duplexes in a test sample in the presence of unhybridized molecular torches. Molecular torches and a variety of types of interacting label pairs are disclosed by Becker et al., "Molecular Torches," U.S. Pat. No. 6,534,274.

Another example of a detection probe having self-complementarity is a "molecular beacon." Molecular beacons include nucleic acid molecules having a target complement sequence, an affinity pair (or nucleic acid arms) holding the probe in a closed conformation in the absence of a target sequence present in an amplification product, and a label pair that interacts when the probe is in a closed conformation. Hybridization of the target sequence and the target complementary sequence separates the members of the affinity pair, thereby shifting the probe to an open conformation. The shift to the open conformation is detectable due to reduced interaction of the label pair, which may be, for example, a fluorophore and a quencher (e.g., DABCYL and EDANS). Molecular beacons are disclosed by Tyagi et al., "Detectably Labeled Dual Confirmation Oligonucleotide Probes, Assays and Kits," U.S. Pat. No. 5,925,517, and Tyagi et al., "Nucleic Acid Detection Probes Having Non-FRET Fluorescence Quenching and Kits and Assays Including Such Probes," U.S. Pat. No. 6,150,097.

Other self-hybridizing probes for use in the present invention are well known to those of ordinary skill in the art. For example, probe binding pairs having interacting labels, such as those disclosed by Morrison, "Competitive Homogenous Assay," U.S. Pat. No. 5,928,862 and Gelfand et al., U.S. Pat. No. 5,804,375 for PCR reactions, also can be adapted for use in the present invention. Additional detection systems include "molecular switches," as disclosed by Arnold et al., "Oligonucleotides Comprising a Molecular Switch," U.S. Pat. Appln. Pub. No. US 2005-0042638 A1. Other probes, such as those comprising intercalating dyes and/or fluorochromes, might be useful for detection of amplification products in the present invention. See, e.g., Ishiguro et al., "Method of Detecting Specific Nucleic Acid Sequences," U.S. Pat. No. 5,814,447.

In those methods of the present invention where the initial target sequence and the RNA transcription product share the same sense, it may be desirable to initiate amplification before adding probe for real-time detection. Adding probe prior to initiating an amplification reaction may slow the rate of amplification since probe which binds to the initial target sequence has to be displaced or otherwise remove during the primer extension step to complete a primer extension product having the complement of the target sequence. The initiation of amplification is judged by the addition of amplification enzymes (e.g., a reverse transcriptase and an RNA polymerase).

Useful Interactive Labels

Molecular torches and molecular beacons preferably are labeled with an interactive pair of detectable labels. Examples of detectable labels that are preferred as members of an interactive pair of labels interact with each other by FRET or non-FRET energy transfer mechanisms. Fluorescence resonance energy transfer (FRET) involves the radiationless transmission of energy quanta from the site of absorption to the site of its utilization in the molecule, or system of molecules, by resonance interaction between chromophores, over distances considerably greater than interatomic distances, without conversion to thermal energy, and without the donor and acceptor coming into kinetic collision. The "donor" is the moiety that initially absorbs the energy, and the "acceptor" is the moiety to which the energy is subsequently transferred. In addition to FRET, there are at least three other "non-FRET" energy transfer processes by which excitation energy can be transferred from a donor to an acceptor molecule.

When two labels are held sufficiently close that energy emitted by one label can be received or absorbed by the second label, whether by a FRET or non-FRET mechanism, the two labels are said to be in "energy transfer relationship" with each other. This is the case, for example, when a molecular beacon is maintained in the closed state by formation of a stem duplex, and fluorescent emission from a fluorophore attached to one arm of the probe is quenched by a quencher moiety on the opposite arm.

Examples of donor/acceptor label pairs that may be used in connection with the invention, making no attempt to distinguish FRET from non-FRET pairs, include fluorescein/tetramethylrhodamine, IAEDANS/fluororescein, EDANS/DABCYL, coumarin/DABCYL, fluorescein/fluorescein, BODIPY FL/BODIPY FL, fluorescein/DABCYL, lucifer yellow/DABCYL, BODIPY/DABCYL, eosine/DABCYL, erythrosine/DABCYL, tetramethylrhodamine/DABCYL, Texas Red/DABCYL, CY5/BH1, CY5/BH2, CY3/BH1, CY3/BH2 and fluorescein/QSY7 dye. Those having an ordinary level of skill in the art will understand that when donor and acceptor dyes are different, energy transfer can be detected by the appearance of sensitized fluorescence of the acceptor or by quenching of donor fluorescence. When the donor and acceptor species are the same, energy can be detected by the resulting fluorescence depolarization. Non-fluorescent acceptors such as DABCYL and the QSY 7 dyes advantageously eliminate the potential problem of background fluorescence resulting from direct (i.e., non-sensitized) acceptor excitation. Preferred fluorophore moieties that can be used as one member of a donor-acceptor pair include fluorescein, ROX, and the CY dyes (such as CY5). Highly preferred quencher moieties that can be used as another member of a donor-acceptor pair include DABCYL, TAMRA and the BLACK HOLE QUENCHER moieties which are available from Biosearch Technologies, Inc., (Novato, Calif.).

Examples of Useful Indicia of Amplification

By the methods disclosed herein, numerical values indicating a predetermined level of progress in nucleic acid amplification reactions (referred to herein as "indicia of amplification") were compared to provide information about the presence of MRSA bacteria in a sample. Although many different indicia of amplification may be used for this purpose, the invention was illustrated using threshold-based indicia of amplification (resulting in determination of "Ct" values). The invention was further illustrated using multiplex nucleic acid amplification reactions carried out under isothermal conditions. Rather than monitoring reaction progress as a function of amplification cycles, reaction progress was monitored as a function of reaction time. Thus, the Ct values reported herein represented the time required for particular amplification reactions to produce amplicon amounts sufficient to result in a fluorescent signal that reached a threshold value. Of course, numerous variations will suggest themselves as equivalent. For example, there can be normalization and/or background-subtraction steps so that the threshold value to be met or exceeded may be other than a raw fluorescence reading. Preferred methods of comparing indicia of amplification for two nucleic acid targets in a multiplex amplification reaction include subtraction, addition, division and multiplication. Preferably, the comparison is based on the difference between indicia of amplification.

As stated above, a variety of indicia of amplification can be used in connection with the disclosed method. For example, mathematical and computing techniques that will be familiar to those having an ordinary level of skill in the art can be used to identify the time of occurrence of the maximum of the first derivative, or the time of occurrence of the maximum of the second derivative of a real-time run curve. Approaches for determining these features of a growth curve have been detailed by Wittwer et al., in U.S. Pat. No. 6,503,720. Other useful approaches involve calculating a derivative of a growth curve, identifying a characteristic of the growth curve, and then determining the threshold time or cycle number corresponding to the characteristic of the derivative. Such techniques have been disclosed in U.S. Pat. No. 6,783,934. Other useful indicia of amplification include threshold-based indicia, such as those described by Higuchi et al., in published European patent application EP 0 640 828 A1, or "TTime" values determined by the method disclosed in U.S. patent application Ser. No. 60/659,874, the disclosure of these applications being incorporated by reference herein. Simply stated, threshold-based indicia of amplification estimate the time at which a particular threshold indicating amplicon production is passed in a real-time amplification reaction. Still other useful indicia include "TArc" and "OTArc," each of these being determined using vector-based analyses of real-time run curves. These indicia of amplification identify the point in time at which a growth curve begins to curve or "inflect" upward. Detailed presentations concerning the determination and use of TArc and OTArc values appear in U.S. patent application Ser. No. 11/474,698, the disclosure of this application being incorporated by reference herein.

Comparing Indicia of Amplification

In accordance with the invention, a numerical value that is a function of indicia of amplification determined for the coamplified *S. aureus*-specific target nucleic acid and mecA target nucleic acid are calculated. Simply stated, target level differences can be inferred from the amplification kinetics for the two coamplified nucleic acid targets. Preferably, the two indicia of amplification from a single coamplification reaction (i.e., indicia for each of the *S. aureus*-specific target nucleic acid and mecA target nucleic acid) are used as variables to solve an equation of some sort. Examples of mathematical relationships that contemplated to be useful for this purpose used include multiplication, division, addition and subtraction. Mathematically relating the two indicia of amplification by subtraction (i.e., to establish the difference therebetween) is most highly preferred, and simplifies establishment of a threshold cut-off value. The difference between two indicia of amplification can be represented by the term, "$\Delta Ct$." These $\Delta Ct$ values can be compared with threshold-based criteria to make a determination about the output result of a diagnostic method.

Establishment and Use of the Threshold Cut-Off Value

In accordance with the invention, a threshold cut-off value is used for determining whether a test sample comprises MRSA, or a mixture of MSSA and MR-CoNS. For example, if the numerical value calculated as the solution of a mathematical equation using as variables indicia of amplification determined for the *S. aureus*-specific target nucleic acid and mecA target nucleic acid (e.g., the $\Delta Ct$ value) for an MRSA-positive sample is $-1$, and if the similarly calculated value using indicia of amplification for a sample comprising a mixture of MSSA and MR-CoNS but not MRSA is $-3$, then setting a threshold cut-off value of $-2$ would distinguish one sample from the other. Stated differently, in this instance the $\Delta Ct$ value for the MRSA sample (i.e., $-1$) would be "separated" from the $\Delta Ct$ value for the MSSA sample (i.e., $-3$) by a threshold cut-off value set to $-2$. Notably, adjusting or changing the value of the threshold cut-off would modify the sensitivity and specificity of the assay. This can be appreciated by understanding that changing the value of the threshold cut-off value shown as the horizontal line in FIG. 7B from $-2$ to $-4$ would correctly include an additional 1-2 MRSA-positive samples, but would also include an additional MRSA-negative sample (i.e., increase the false-negative assignments). Thus, simply adjusting the value of the threshold cut-off used for making the mutually exclusive MRSA or MSSA assignment modifies the sensitivity and specificity of the assay.

Apparatus for Implementing an Algorithm

The methods disclosed herein can be conveniently implemented in-part using a computer or similar processing device ("computer" hereafter). In different preferred embodiments, software or machine-executable instructions for performing an algorithm can be loaded or otherwise held in a memory component of a freestanding computer, or in a memory component of a computer linked to a device used for monitoring, preferably as a function of time, the amount of an a product undergoing analysis. In a highly preferred embodiment, software for executing the algorithm is held in a memory component of a computer that is linked to, or that is an integral part of a device capable of monitoring the amount of an amplicon present in a reaction mixture as a function of time.

Indeed, either or both of a controller system for controlling a real-time amplification device and/or the detection system of the real-time amplification device can be coupled to an appropriately programmed computer which functions to instruct the operation of these instruments in accordance with preprogrammed or user input instructions. The computer preferably also can receive data and information from these instruments, and interpret, manipulate and report this information to the user. Outputs of the algorithm may take various forms, including paper printouts, or outputs to a computer monitor, display device, or other interface. Results also may be stored in electronic or magnetic media.

In general, the computer typically includes appropriate software for receiving user instructions, either in the form of user input into a set of parameter fields, or in the form of preprogrammed instructions (e.g., preprogrammed for a variety of different specific operations). The software then converts these instructions to appropriate language for instructing the operation of the real-time amplification controller to carry out the desired operation. The computer also is capable of receiving data from the one or more sensors/detectors included within the system, and interprets the data in accordance with the programming. The system preferably includes software that correlates a feature of a growth curve representing the quantity of amplified copies of the nucleic acid of interest as a function of time, as detected by the detector, to the number of copies of the nucleic acid of interest present in a test sample.

Preferably, when the computer used for executing the disclosed method is an integral component of an apparatus for performing and analyzing real-time nucleic acid amplification reactions, the apparatus preferably comprises a temperature-controlled incubator, a detection device for collecting signals, an analyzing device (e.g., a computer or processor) for analyzing signals and an output device for displaying data obtained or generated by the analyzing device. The analyzing device may be connected to the temperature-controlled incubator through an input device known in the art, and/or connected to an output device known in the art for data display. In one embodiment, the temperature-controlled incubator is capable of temperature cycling.

Generally speaking, the various components of an apparatus for performing the real-time nucleic acid amplification useful in connection with the disclosed methods will be conventional components that will be familiar to those having an ordinary level of skill in the art. The temperature-controlled incubator used to perform and analyze real-time nucleic acid amplification may be of a conventional design which can hold a plurality of reaction tubes, or reaction samples in a temperature-controlled block in standard amplification reaction tubes or in wells of a multiwell plate. In one aspect, the detection system is suitable for detecting optical signals from one or more fluorescent labels. The output of the detection system (e.g., signals corresponding to those generated during the amplification reaction) can be fed to the computer for data storage and manipulation. In one embodiment, the system detects multiple different types of optical signals, such as multiple different types of fluorescent labels and has the capabilities of a microplate fluorescence reader. The detection system is preferably a multiplexed fluorimeter containing an excitation light source, which may be a visible light laser or an ultraviolet lamp or a halogen lamp, a multiplexer device for distributing the excitation light to the individual reaction tubes and for receiving fluorescent light from the reaction tubes, a filtering means for separating the fluorescence light from the excitation light by their wavelengths, and a detection means for measuring the fluorescence light intensity. Preferably, the detection system of the temperature-controlled incubator provides a broad detection range that allows flexibility of fluorophore choice, high sensitivity and excellent signal-to-noise ratio. Optical signals received by the detection system are generally converted into signals which can be operated on by the processor to provide data which can be viewed by a user on a display of a user device in communication with the processor. The user device may comprise a user interface or may be a conventional commercially available computer system with a keyboard and video monitor. Examples of data which can be displayed by the user device include amplification plots, scatter plots, sample value screens for all the tubes or reaction vessels in the assembly and for all labels used, an optical signal intensity screen (e.g., fluorescent signal intensity screen), final call results, text reports, and the like.

Preferred Amplification Oligonucleotides

Amplification oligonucleotides useful for conducting amplification reactions can have different lengths to accommodate the presence of extraneous sequences that do not participate in target binding, and that may not substantially affect amplification or detection procedures. For example, promoter oligonucleotides useful for performing amplification reactions in accordance with the invention have at least a minimal sequence that hybridizes to the target nucleic acid, and a promoter sequence positioned upstream of that minimal sequence. However, insertion of sequences between the target binding sequence and the promoter sequence could change the length of the primer without compromising its utility in the amplification reaction. Additionally, the lengths of the amplification primers and detection probes are matters of choice as long as the sequences of these oligonucleotides conform to the minimal essential requirements for hybridizing the desired complementary sequence.

Tables 1-3 present specific examples of oligonucleotide sequences that were used to illustrate the invention. Table 1 presents the sequences of amplification oligonucleotides used for amplifying *S. aureus* 23S rDNA sequences. Table 2 presents the sequences of amplification oligonucleotides used for amplifying mecA DNA sequences. Table 3 presents the sequences of amplification oligonucleotides used for amplifying the internal control DNA. All promoter oligonucleotides used for illustrating the invention include at their 3' ends sequences complementary to one of the target sequence, and at their 5' ends a T7 promoter sequence (presented in lowercase). Additionally, the 3' termini of all promoter oligonucleotides were blocked using a reverse polarity C nucleotide that could not be extended by a DNA polymerase. In terminating oligonucleotide SEQ ID NO:3, positions 1-3, 6, 9-10, 17-18, 21, and 25 were LNA nucleotide analogs, and the 3'terminus was blocked using a reverse polarity C nucleotide that could not be extended by a DNA polymerase. In terminating oligonucleotide SEQ ID NO:12, positions 3-5, 11-13, 17-19 were LNA nucleotide analogs, and the 3' terminus was blocked using a reverse polarity C that could not be extended by a DNA polymerase. In terminating oligonucleotide SEQ ID NO:16, positions 5-7, 11-13 and 17-19 were occupied by LNA analogs, and the 3' terminus was blocked using a reverse polarity C that could not be extended by a DNA polymerase.

TABLE 1

Polynucleotide Sequences of Amplification Oligonucleotides: *S. aureus* 23S rDNA Target

| Oligo Function | Sequence | Oligo Name |
|---|---|---|
| Priming Oligo | TGG GGT TGT AGG ACA CTC T | SEQ ID NO: 1 |
| Displacer Oligo | GAG AAA GAA AAT TCG ATT CCC TT | SEQ ID NO: 2 |
| Terminating Oligo | TTG AGT GGA TCC TGA GTA CGA CGG AG | SEQ ID NO: 3 |
| Promoter Oligo | aat tta ata cga ctc act ata ggg aga CCA CAA CGG TCT CAA GAG AGA CAA CAT TTT CGA | SEQ ID NO: 4 |

TABLE 2

Polynucleotide Sequences of Amplification Oligonucleotides: mecA Target

| Oligo Function | Sequence | Oligo Name |
|---|---|---|
| Priming Oligo | GCA ACG TTC AAT TTA ATT TTG TTA AAG | SEQ ID NO: 5 |
| Priming Oligo | GCAACGTTCAATTTAATTTTGT | SEQ ID NO: 6 |
| Priming Oligo | GCAACGTTCAATTTAATTTTGTT | SEQ ID NO: 7 |
| Priming Oligo | GCAACGTTCAATTTAATTTTGTTAAA GAAGATGG | SEQ ID NO: 8 |
| Priming Oligo | GCAACGTTCAATTTAATTTTGTTAAA GAAGATGGTA | SEQ ID NO: 9 |
| Displacer Oligo | AAC GAG TAG ATG CTC AAT ATA AA | SEQ ID NO: 10 |
| | CAA ACT ACG GTA ACA TTG | SEQ ID NO: 11 |
| Terminating Oligo | AGA CCA AAG CAT ACA TAT TGA A | SEQ ID NO: 12 |
| Promoter Oligo | aat tta ata cga ctc act ata ggg aga TGG TCT TTC TGC ATT CCT GGA ATA ATG A | SEQ ID NO: 13 |

TABLE 3

Polynucleotide Sequences of Amplification Oligonucleotides: Internal Control

| Oligo Function | Sequence | Oligo Name |
|---|---|---|
| Priming Oligo | GAC CAT GTC CCA ATT CGC ACC AGG | SEQ ID NO: 14 |
| Displacer Oligo | GCG ATG ATT GAC TTG TGA TTC CGC | SEQ ID NO: 15 |
| Terminating Oligo | AAT CTA TTG TCA CTT CCT TGA | SEQ ID NO: 16 |
| Promoter Oligo | aat tta ata cga ctc act ata ggg aga AGA TTA TAT AGG ACG ACA AGT AAA AAT TA | SEQ ID NO: 17 |

Preferred Detection Probes

Hybridization probes useful for detecting analyte nucleic acid sequences include a sequence of bases substantially complementary to either a *S. aureus* rDNA target nucleic acid sequence, to a mecA target nucleic acid sequence, or to an internal control target nucleic acid. Thus, probes of the invention preferably hybridize one strand of an amplified target nucleic acid sequence, or the complement thereof. These probes may optionally have additional bases outside of the targeted nucleic acid region which may or may not be complementary to the target nucleic acid that is to be detected.

Highly preferred probes are able to hybridize to amplified *S. aureus* 23S ribosomal nucleic acid, to mecA nucleic acid, or to internal control nucleic acids under conditions suitable for performing a nucleic acid amplification reaction, such as those described herein. Tables 4-6 respectively present the full sequences of some of the hybridization probes that were used for detecting *S. aureus* 23S ribosomal, mecA and internal control amplicons. The molecular torch presented in Table 4 was labeled with a hexachloro-fluorescein moiety at its 5' end, and with a DABCYL quencher moiety at its 3' end. The molecular torch presented in Table 5 was labeled with a fluorescein moiety at its 5' end, and with a DABCYL quencher moiety at its 3' end. The molecular torch presented in Table 6 was labeled with a ROX moiety at its 3' end, and with a TAMRA quencher moiety at its 5' end. Non-nucleotide 9 carbon (C9) spacers separated base positions 5-6 in the molecular torches presented in Tables 4-5, and base positions 17-18 in the molecular torch presented in Table 6. All of the probes were synthesized using 2'-methoxy nucleotide analogs.

TABLE 4

Polynucleotide Sequences of *S. aureus* 23S Detection Probe

| Sequence | Name: |
|---|---|
| CAU GUC AAA GGA CGA CAU G | SEQ ID NO: 18 |

TABLE 5

Polynucleotide Sequences of mecA Detection Probe

| Sequence | Name: |
|---|---|
| CCA AUU GGA AGU UAG AUU GG | SEQ ID NO: 19 |

TABLE 6

Polynucleotide Sequences of the Internal Control Detection Probe

| Sequence | Name: |
|---|---|
| CCA CUU GCG AUG UUU UAA GUG G | SEQ ID NO: 20 |

As indicated above, any number of different backbone structures can be used as a scaffold for the nucleobase sequences of the invented hybridization probes. In certain highly preferred embodiments, probe sequences used for detecting RNA amplicons include a methoxy backbone, or at least one methoxy linkage in the nucleic acid backbone.

Selection and Use of Capture Oligonucleotides

Simply stated, preferred target capture methods employ one or more nucleic acid oligomers for non-specifically hybridizing target nucleic acid and then separating it from other components of a sample preparation. Details regarding highly preferred non-specific target capture approaches for purifying nucleic acids prior to amplification are given by Becker et al., in the U.S. patent application identified by Ser. No. 11/832,367.

Methods for isolating target nucleic acids prior to amplification preferably involve mixing a sample containing the target nucleic acid with a non-specific capture probe. The capture probe preferably includes a first sequence of bases that hybridize non-specifically with the target nucleic acid. The first oligonucleotide sequence is preferably a random poly-(K) sequence comprising G and T nucleotides or G and U nucleotides. Preferred capture oligonucleotides have covalently attached to the first sequence a second sequence (i.e., a "tail" sequence) that serves as a target for immobilization onto a solid support. The tail sequence, which is preferably at the 3' end of a capture oligonucleotide, is used to hybridize to a complementary base sequence immobilized on the solid support to provide a means for capturing the hybridized analyte nucleic acid in preference to other components in the biological sample. A reaction mixture containing the solid support, the target nucleic acid, and the non-specific capture probe can be incubated under hybridization conditions that allow hybridization of the capture probe and the target nucleic acid to form a hybridization complex that becomes immobilized to the support. Thereafter, there is a step for separating the solid support from a solution phase of the reaction mixture to separate the hybridization complex linked thereto from other sample components, thereby isolating the target nucleic acid from other sample components. In a preferred embodiment, the capturing step takes place by sequentially hybridizing the capture oligonucleotide with the target nucleic acid and then adjusting the hybridization conditions to allow hybridization of the tail portion of the capture oligonucleotide with an immobilized complementary sequence (e.g., as described in PCT No. WO 98/50583).

Retrieving the target nucleic acid:capture oligonucleotide:immobilized probe complex effectively concentrates the target nucleic acid, relative to its concentration in the biological sample, and purifies the target nucleic acid from amplification inhibitors which may be present in the biological sample. The captured target nucleic acid may be washed one or more times, further purifying the target, for example, by resuspending the particles with the attached target nucleic acid:capture oligonucleotide:immobilized probe complex in a washing solution and then retrieving the particles with the attached complex from the washing solution as described above. After the capturing step and any optional washing steps have been completed, the target nucleic acid can then be amplified. To limit the number of handling steps, the target nucleic acid optionally can be amplified without releasing it from the capture oligonucleotide.

The capture oligonucleotide used for illustrating the invention is presented in Table 7. Positions 1-18 of the capture oligonucleotide were a random poly-(K) sequence of G and T bases. A poly-(dA) tail sequence was located at the 3' end of the oligonucleotide. The capture oligonucleotide also included a spacer made up of three optional thymidine nucleotides interposed between the non-specific target-hybridizing sequence and the poly-(dA) tail. The presence of these thymidine nucleotides is not believed to be essential for success of the capture procedure. The three thymidine nucleotides and the poly-(dA) tail were synthesized using DNA precursors, while the non-specific target hybridizing portion of the oligonucleotide was synthesized using a combination of DNA precursors and LNA nucleotide analogs. More specifically, the capture oligonucleotide was DNA except for LNA analogs at positions 1-3, 7-9 and 13-15. The 3' terminus of the oligonucleotide was blocked using a reverse polarity C nucleotide that could not be extended by a DNA polymerase.

TABLE 7

Non-specific Target Capture Oligonucleotide

| Sequence | Name |
|---|---|
| KKK KKK KKK KKK KKK KKK TTT AAA AAA AAA AAA AAA AAA AAA AAA AAA AAA | SEQ ID NO: 21 |

Internal Control

Assays for detecting amplified nucleic acids may optionally include an internal control (IC) nucleic acid that is amplified and detected in the same amplification reaction mixture. The IC may be amplified by using amplification oligonucleotides and detection probes specific for the IC sequence. Detection of a signal from the amplified IC sequence demonstrates that the assay reagents, conditions, and procedural steps were properly used and performed in the assay if no signal is obtained for the intended analyte nucleic acid (e.g., samples that provide negative results for *S. aureus* and mecA analyte nucleic acids). A preferred IC embodiment is a randomized sequence that has been derived from a naturally occurring source (e.g., an HIV sequence that has been rearranged in a random manner). A preferred IC may be an RNA transcript or DNA molecule isolated from a naturally occurring source, or synthesized chemically or by in vitro techniques. The primers and probe for the IC target sequence are designed and synthesized by using any well known method provided that the primers and probe function for amplification and detection of the IC sequence using substantially the same assay conditions used to amplify and detect the analyte target sequence. In preferred embodiments that include a target capture-based purification step, a target capture probe specific for the IC target is included in the target capture step so that the IC is treated in the same conditions as used for the intended analyte in all of the assay steps.

Alternative *S. aureus*-Specific Target Sequences

In addition to *S. aureus*-specific ribosomal nucleic acid sequences, other *S. aureus*-specific nucleic acid sequences can be substituted for the ribosomal nucleic acid sequence disclosed herein. For example, the above-referenced orfX gene sequence is known to be highly conserved in *S. aureus*, and is known to be the site of SCCmec integration. Accordingly, the present invention is intended to embrace methods comprising amplification and detection of *S. aureus*-specific orfX nucleic acid sequences in place of *S. aureus*-specific nucleic acid sequences. Of course, these procedures can involve amplification of only a portion of the orfX sequence, such as amplification of the portion of orfX near or including the integrated sequence that confers resistance to methicillin. Embodiments of the invention that rely on amplification across the integration junction are particularly preferred in coamplification reactions with mecA sequences. Application of the threshold criterion to kinetic results obtained in such an amplification reaction can enhance specificity with respect to MRSA identification. More particularly, such an application can reduce the incidence of false-positive MRSA identifications that would otherwise result from either: (1) detection of the insertion junction as a direct indicator of the presence of MRSA in a clinical sample (e.g., a nasal swab sample); or (2) qualitative detection of the insertion junction and mecA nucleic acid sequences as a direct indicator of the presence of MRSA in the clinical sample. Compositions and methods for amplifying portions of the orfX sequence, or across the orfX junction contained in MRSA bacteria are readily available to those having an ordinary level of skill in the art (e.g., see U.S. Pat. No. 6,156,507, and U.S. Pat. No. 7,449,289).

Methods of Resolving Complex Mixtures of Bacteria in Clinical Samples

Proceeding from the results obtained using the real-time amplification system described herein, we examined clinical specimens (i.e., nasal swabs) that had been typed as MRSA-positive or MRSA-negative using gold standard microbiology techniques.

Figure 1B:
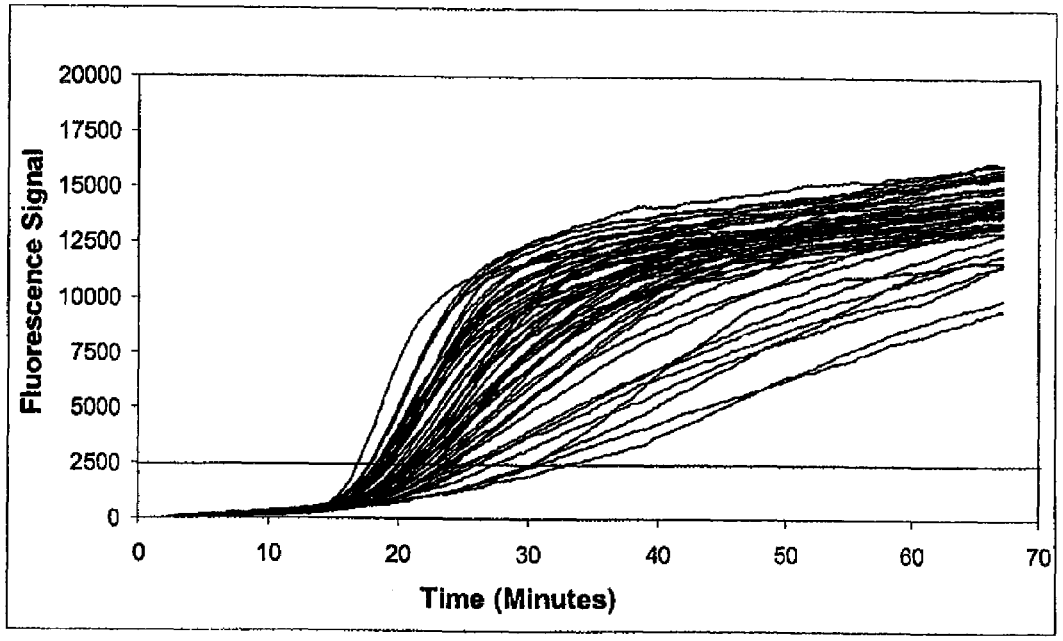
Figure 2A:
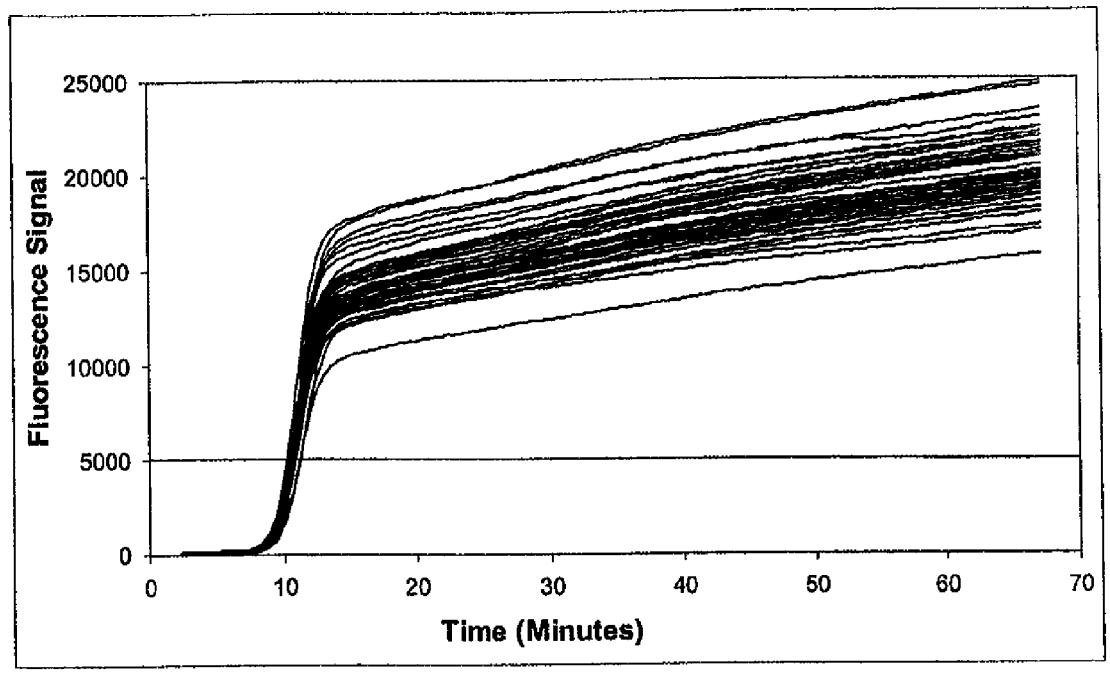
FIGS. 2A-2B are graphical presentations of real-time run curves for amplification of the S. aureus marker (panel A) and of the mecA marker (panel B) in reactions preformed using 160 CFU of MRSA and 100,000 CFU of MSSA bacteria. The vertical axes show fluorescent signals, measured in RFU, for 50 amplification reactions. The horizontal lines drawn at 5,000 RFU (panel A) and at 2,500 RFU (panel B) on the vertical axes represent partial criteria used for determining positive amplification results.
Figure 2B:
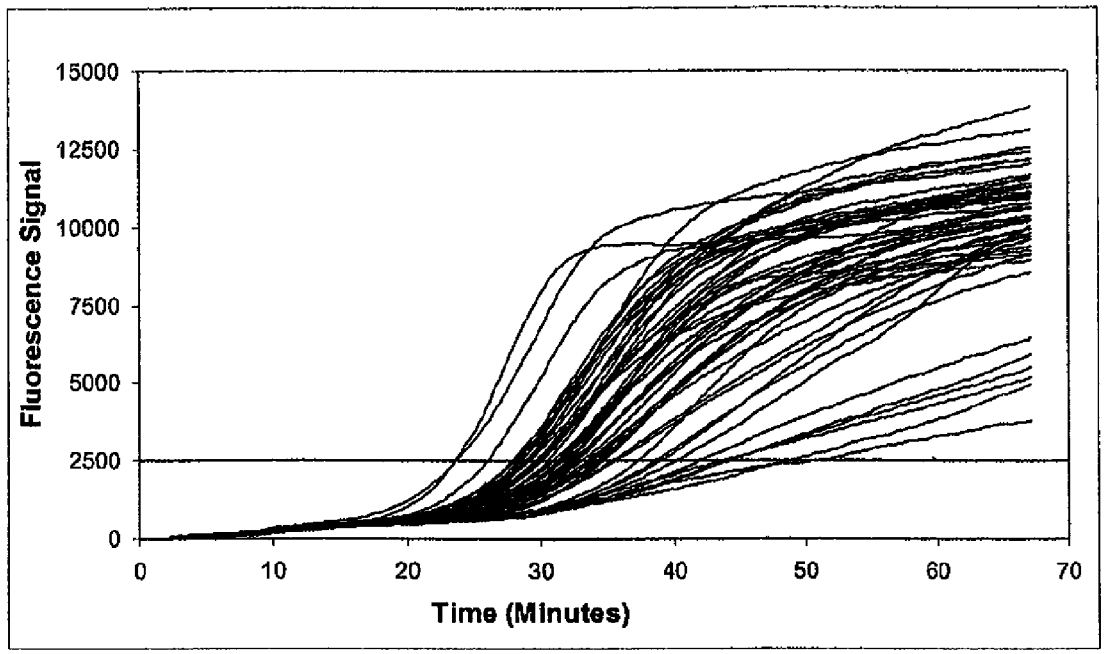

The results presented in FIGS. 1-3 supported an approach for detecting co-infected samples. FIG. 1 presents results for amplification of *S. aureus* and mecA target sequences in a multiplex reaction using templates derived from a small number of MRSA bacteria in the presence of a large number of non-target bacteria. FIG. 2 presents results for amplification of *S. aureus* and mecA target sequences in a multiplex reaction using templates derived from a small number of MRSA bacteria in the presence of a large number of MSSA bacteria. Since the number of copies of the *S. aureus* target sequence was substantially higher in the reaction giving rise to results presented in FIG. 2A when compared to the results presented in FIG. 1A, the run curves for the *S. aureus* target generally emerged from background fluorescence levels at earlier times during the reaction for the trial having proportionately greater *S. aureus* 23S rDNA targets. At the same time, the run curves for the mecA target sequence generally emerged from background levels at later times during the reaction (e.g., compare the run curves in FIGS. 2B and 2A). Stated differently, the Ct value for the *S. aureus* target (i.e., "Ct(Sau)") was reduced, and the Ct value for the mecA target (i.e., "Ct(mec)") was increased relative to a trial carried out using only templates contributed by MRSA bacteria. Thus, the difference between Ct values determined for the *S. aureus* and mecA target nucleic acids (i.e., calculated as $\Delta Ct=Ct(Sau)-Ct(mecA)$) reflected the contributions of the two target sequences in the multiplex amplification reaction. Notably, a relative increase in the copy number of one target was associated with a more rapid emergence of the run curve for that target (i.e., a smaller Ct value), and with a corresponding delay in the emergence time of the run curve representing the second target (i.e., a larger Ct value) in the same multiplex amplification reaction.

Notably, the method of assessing complex mixtures of bacteria (e.g., MRSA and MSSA bacteria) using $\Delta Ct$ values does not require that the S, aureus-specific and mecA-specific amplification reactions influence each other, for example by competing for amplification resources in a multiplex reaction.

When MSSA and MRSA are both present in a sample undergoing testing, amplification of the *S. aureus* target from MSSA competes for amplification resources, slowing down the amplification of the mecA target sequence in a multiplex reaction (i.e., both targets being amplified in a single reaction). The extent of this competition will vary with the nature of the amplification system, and could be substantially non-existent as, for example, in PCR. Nevertheless, a ΔCt will still exist. Thus, ΔCt does not depend upon competition.

The consequence of this was profound for several reasons. First, it explicitly illustrated a trend that would be expected for test samples containing mixtures of MRSA and MSSA bacteria. More particularly, a mixture of those target organisms could be recognized by an increase in the separation between the Ct values of run curves for the *S. aureus*-specific and mecA-specific amplification reactions (i.e., the magnitude of ΔCt would increase). If ΔCt is calculated by the equation given above, the value of ΔCt would become more negative than the ΔCt value that would be expected for a sample containing MRSA only. By contrast, a mixture of MRSA and MR-CoNS would be expected to yield run curves spaced more closely together when compared with run curves obtained using a pure MRSA sample. This is because the increased number of mecA templates in the multiplex amplification reaction would cause the mecA run curve to emerge from background at an earlier time relative to the MRSA control, and cause the *S. aureus*-specific run curve to be delayed in its emergence time relative to the MRSA control. In this instance, the value of ΔCt calculated by the equation given above would increase (i.e., become more positive) when compared with the value expected for a sample containing MRSA only. Finally, a mixture of MSSA and MR-CoNS would be expected to yield *S. aureus*-specific and mecA-specific run curves spaced apart by the amount characteristic of a pure MRSA culture control only infrequently (e.g., when the relative number of *S. aureus*-specific and mecA-specific templates exactly matched the relative numbers found in authentic MRSA bacteria). Whether the ΔCt value calculated for such a mixture would be greater or less than the ΔCt value characteristic of a reaction carried out using templates isolated from a sample of pure MRSA was not predictable.

Objects of the kinetic analysis procedure included: (1) identifying infection by MRSA; (2) identifying infection by MSSA; (3) minimizing false-positive MRSA identifications arising from co-infection by MSSA and MR-CoNS; and (4) minimizing false-negative results. The preferred approach relied on the use of at least one empirically determined threshold for designating samples as being MRSA-positive.

Figure 4A:
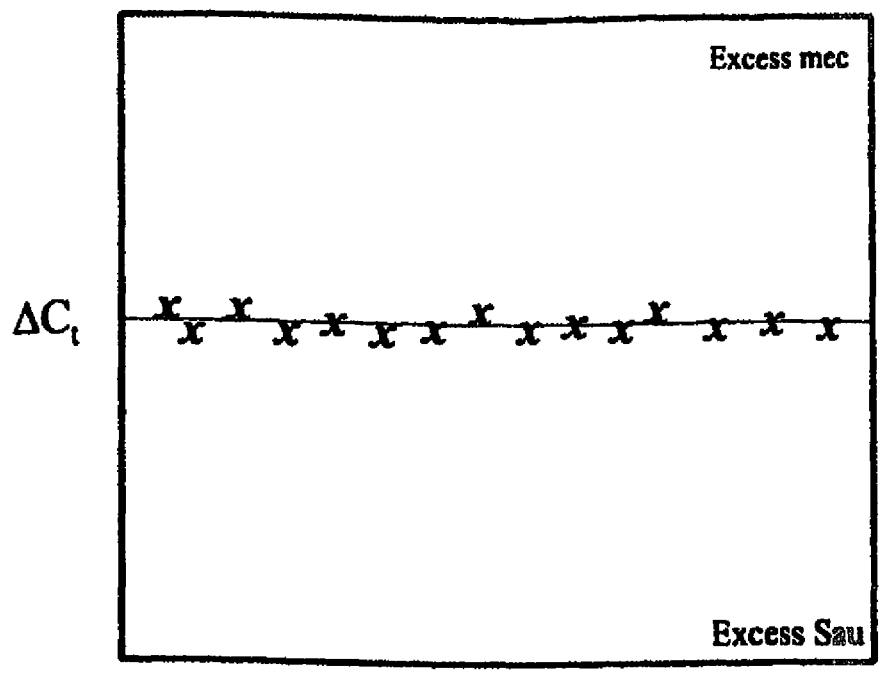
FIGS. 4A-4B present schematic plots of ΔCt values for different multiplex amplification trials using truly positive MRSA samples ("X"), and truly negative MRSA samples ("x"). Panel A shows results for 15 MRSA pure cultures (i.e., MRSA-positive samples not containing MSSA or MR-CoNS), and demonstrates that the ΔCt values determined from those multiplex amplification reactions are substantially constant. The results define a horizontal line or threshold on the plot. Panel B shows ΔCt values determined for 8 truly positive MRSA samples, and for 8 truly negative MRSA trials scored as false-positives.

Based on the description above, samples that included MRSA, but that did not include MSSA or MR-CoNS, were expected to yield ΔCt values substantially equal to an empirically determined value. This is illustrated by the horizontal line drawn in FIG. 4A. In our experiments ΔCt equaled about −2 minutes. It was a reasonable assumption that clinical samples would represent complex mixtures of bacteria, including mixtures of: (1) MSSA and MR-CoNS, (2) MRSA and MSSA, (3) MRSA and MR-CoNS. Allowing that the relative numbers of these different bacteria would be distributed somewhat randomly across different samples, the result shown in FIG. 4B was expected. As illustrated in the figure, truly MRSA-positive samples (X) would yield ΔCt values falling on the line (i.e., indicating single infection by MRSA), above the line (i.e., indicating co-infection by MRSA and MR-CoNS), and below the line (i.e., indicating co-infection by MRSA and MSSA). Likewise, false-positive trials (x) resulting from co-infection by MSSA and MR-CoNS would be expected to have ΔCt values falling on the line (i.e., when relative proportions of the two target nucleic acids matched the proportions naturally found in MRSA bacteria), above the line (i.e., resulting from a relative excess of the mecA template compared to the amount naturally found in MRSA bacteria), and below the line (i.e., resulting from a relative excess of the *S. aureus* template compared to the amount naturally found in MRSA bacteria).

Figure 4B:
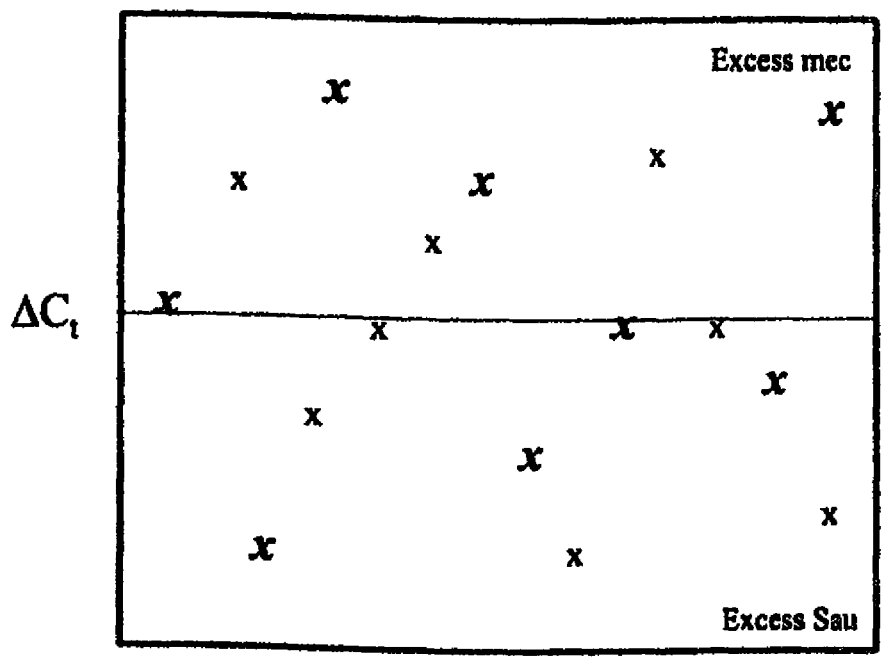

Contrary to expectations based on the model illustrated in FIG. 4B, and as supported by the empirical observations presented in the Examples below, the distribution of truly positive and false-positive results showed dramatically different partitioning with respect to a ΔCt threshold value. More specifically, there was an overwhelming tendency to identify co-infections of MRSA with MR-CoNS rather than with MSSA. These trials clustered above the horizontal line drawn in FIGS. 4A-4B. Rather than clustering in some fashion, false-positives arising from co-infection by MSSA and MR-CoNS were substantially evenly distributed above and below a ΔCt threshold, although there appeared to be a slight preference for false-positive trials to partition below the line shown in the figures. Based on these observations, it was possible to establish a threshold value that could be used for designating or assigning MRSA-positive samples. Thus, in accordance with the invention, MRSA-positive samples were identified as those samples giving rise to ΔCt values that substantially equaled or exceeded a threshold value.

Kits for Detecting MRSA and MSSA Nucleic Acids

In addition to the methods described herein, the present invention is drawn to kits comprising one or more of the reagents required for carrying out the methods described herein. Kits comprising various components used in carrying out the present invention may be configured for use in any procedure requiring amplification of nucleic acid target molecules, and such kits can be customized for various different end-users. Kits of the present invention provide one or more of the components necessary to carry out nucleic acid amplifications according to the invention. Kits may include reagents suitable for amplifying nucleic acids from one particular target or may include reagents suitable for amplifying multiple targets. Kits of the present invention may further provide reagents for real-time detection of one or more nucleic acid targets in a single sample, for example, one or more self-hybridizing probes having stem-and-loop structures as described above. Kits may comprise a carrier that may be compartmentalized to receive in close confinement one or more containers such as vials, test tubes, wells, and the like. Preferably at least one of such containers contains one or more components or a mixture of components needed to perform the amplification methods of the present invention.

A kit according to one embodiment of the present invention can include, for example, in one or more containers, a priming oligonucleotide, a terminating oligonucleotide for terminating a primer extension reaction, and, optionally, an extender oligonucleotide and/or a capping oligonucleotide. If real-time detection is used, the one or more containers may include one or more reagents for real-time detection of at least one nucleic acid target sequence in a single sample, for example, one or more self-hybridizing probes having stem-and-loop structures, as described above. Another container may contain an enzyme reagent, such as a heat stable DNA polymerase for performing a PCR or RT-PCR reaction, or a mixture of a reverse transcriptase (either with or without RNAse H activity), an RNA polymerase, and optionally an additional selective RNAse enzyme for a transcription-based amplification reaction. These enzymes may be provided in concentrated form or at working concentration, usually in a form which promotes enzyme stability. The enzyme reagent may also be provided in a lyophilized form, for example, as taught by Shen et al., in U.S. Pat. No. 5,834,254. Another one or more containers may contain an amplification reagent in concentrated form, or at working concentration. An amplification reagent will contain one or more of the components necessary to run the amplification reaction (e.g., a buffer, $MgCl_2$, KCl, dNTPs, rNTPs, EDTA), stabilizing agents, etc. Certain of the components (e.g., $MgCl_2$ and rNTPs), may be provided separately from the remaining components, allowing the end user to titrate these reagents to achieve more optimized amplification reactions. Another one or more containers may include reagents for detection of amplification products, including one or more labeled oligonucleotide probes. Probes may be labeled in a number of alternative ways (e.g., with radioactive isotopes, fluorescent labels, chemiluminescent labels, nuclear tags, bioluminescent labels, intercalating dyes, or enzyme labels). In some embodiments, a kit of the present invention will also include one or more containers having one or more positive and negative control target nucleic acids which can be utilized in amplification experiments in order to validate the test amplifications carried out by the end user. In some instances, one or more of the reagents listed above may be combined with an internal control. Of course, it is also possible to combine one or more of these reagents in a single tube or other containers. Supports suitable for use with the invention (e.g., test tubes, multi-tube units, multi-well plates, microfluidic cartridges, etc.), may also be supplied with kits of the invention. Finally a kit of the present invention may include one or more instruction manuals.

Kits of the invention may contain virtually any combination of the components set out above or described elsewhere herein. As one skilled in the art would recognize, the components supplied with kits of the invention will vary with the intended use for the kits, and the intended end user. Thus, kits may be specifically designed to perform various functions set out in this application and the components of such kits will vary accordingly.

WORKING EXAMPLES

The general principles of the present invention may be more fully appreciated by reference to the following non-limiting Examples.

Example 1 illustrates the detection of MRSA and MSSA bacteria using a multiplex real-time amplification assay. Three independent single-primer transcription-associated amplification assays were used for amplifying and detecting *S. aureus* 23S rDNA, mecA DNA and an unrelated artificial internal control DNA in a single tube. Each of the three nucleic acid targets in the procedure was amplified using unique amplification oligonucleotides, and was detected using unique molecular torches. As described below, procedures were performed to assess detection of small quantities of MRSA bacteria in samples containing large excesses of either (a) the combination of two different methicillin-sensitive coagulase-negative *staphylococcus* bacteria (i.e., *S. haemolyticus* and *S. epidermidis*), or (b) MSSA. As well, detection of small quantities of MSSA bacteria in samples containing large excesses of the two methicillin-sensitive coagulase-negative *staphylococcus* bacteria also was assessed.

Example 1

Detection of MRSA and MSSA in the Presence of Closely Related Organisms

Samples containing bacterial targets used for testing were prepared as follows. Sterile BBL CULTURE SWABS (Becton, Dickinson and Company) were inserted into companion tubes containing Stuart's Medium and allowed to stand for at least 6 hours at room temperature to simulate batch collection conditions. Individual swabs were transferred into 1.7 ml Eppendorf reaction tubes containing 250 µl of a sample buffer solution consisting of 10 mM Tris (pH 8.0) and 1 mM EDTA. Excess lengths of swab applicator handles were removed to permit containment of the swabs in the reaction tubes. Tubes were subsequently capped shut and vortexed for 30 seconds. Swabs were removed immediately after vortexing. Next, 80 µl of residual sample buffer was transferred into each of two 1.7 ml Eppendorf reaction tubes. Replicate tubes next received 20 µl aliquots containing known quantities of bacteria for one of three different challenge conditions. These conditions were: (a) 160 colony forming units (CFU) of MRSA bacteria, and 100,000 CFU each of *S. epidermidis* and *S. haemolyticus* bacteria, (b) 160 CFU of MRSA bacteria and 100,000 CFU of *S. aureus* (MSSA) bacteria, and (c) 160 CFU of MSSA bacteria, and 100,000 CFU each of *S. epidermidis* and *S. haemolyticus* bacteria. Each tube then received a 100 µl aliquot of lysis buffer containing 5,000 copies of the internal control DNA. Tubes were vortexed 1-2 seconds, and allowed to stand at room temperature for 10 minutes. Each tube then received a 40 µl aliquot of Target Capture Reagent (TCR) made 1M HEPES (pH 6.5), 500 µg/ml of oligo-(dT) magnetic beads (Seradyn Corp.; Indianapolis, Ind.), and 200 µmol/ml of the 3' blocked non-specific target capture oligonucleotide of SEQ ID NO:21. After vortexing briefly, 200 µl aliquots of the mixtures were transferred into the wells of a 96 well KF200 plate (Thermo Fisher Scientific, Inc.; Waltham, Mass.) for subsequent processing. This was designated Plate 1.

Automated washing of nucleic acids captured non-specifically onto the magnetic beads was carried out using a KING-FISHER 96 (Thermo Fisher Scientific, Inc.; Waltham, Mass.) magnetic particle processor. First there were prepared two microtiter plates, each containing 200 µl of wash reagent (Plates 2 and 3). The wash reagent was a HEPES buffered solution that included 150 mM NaCl and 0.1% (w/v) sodium dodecyl sulfate. Another microtiter plate (MJ Research 96 well plate) for conducting amplification reactions (Plate 4) was also prepared, with each well to be used for a reaction containing 30 µl of amplification reagent. The amplification reagent included a pH buffered mixture of ribonucleotide triphosphates, deoxyribonucleotide triphosphates, salts and cofactors, as will be familiar to those having an ordinary level of skill in the art (for example, see U.S. patent application Ser. No. 11/681,104). The amplification reagent further included priming oligonucleotides (SEQ ID NO:1, SEQ ID NO:5, and SEQ ID NO:14), terminating oligonucleotides (SEQ ID NO:3, SEQ ID NO:12, and SEQ ID NO:16), and promoter oligonucleotides (SEQ ID NO:4, SEQ ID NO:13, and SEQ ID NO:17). Notably, in certain procedures the oligonucleotide of SEQ ID NO:5 was substituted by one of SEQ ID NOs:6-9 for amplification of mecA sequences with excellent results. Thus, each of SEQ ID NOs:6-9 represents a preferred oligonucleotide in accordance with the invention, either alone or in combination with other amplification and detection oligonucleotides. All four plates (Plates 1-4) were loaded into the magnetic particle processor unit. Magnetic beads harboring nucleic acid complexes were isolated from Plate 1, washed first in Plate 2, transferred into Plate 3 for another cycle of washing, and finally transferred into the wells of Plate 4 in preparation for amplification, all using standard procedures familiar to those having an ordinary level of skill in the art.

Real-time monitoring of isothermal nucleic acid amplification reactions was carried out using a temperature-controlled MX3005p instrument (Stratagene; La Jolla, Calif.). Plate 4 was first removed from the KINGFISHER 96 magnetic particle processor unit, and then placed into the temperature-controlled instrument. The plate was first incubated at 60° C. for 3 minutes, and then incubated at 42° C. for 5 minutes. The microtiter plate was next transferred onto an EPPENDORF THERMOMIXER® (Eppendorf North America; Westbury, N.Y.) set at 44° C. Each reaction well received a 10 µl aliquot of enzyme reagent containing displacer oligonucleotides (SEQ ID NO:2, SEQ ID NO:10, SEQ ID NO:11, and SEQ ID NO:15), and molecular torches (SEQ ID NO:18, SEQ ID NO:19, and SEQ ID NO:20). The enzyme reagent included a pH buffered mixture of Moloney murine leukemia virus ("MMLV") reverse transcriptase, T7 RNA polymerase, as will be familiar to those having an ordinary level of skill in the art (for example, see U.S. patent application Ser. No. 11/681,104). The plate was sealed with an adhesive cover, gently shaken for 1 minute, and then transferred into the real-time instrument that had been set to incubate at 42° and read fluorescent signals from the three molecular torches every 16 seconds. Fluorescent signals were measured in relative fluorescence units (RFU). Threshold-based TTime values, which served as indicators of the amount of amplicon synthesized, were determined from the monitored fluorescence signals essentially according to the methods disclosed by Light et al., in U.S. Pub. No. 2006-0276972 A1.

Acceptance criteria for valid results required that at least one of the three reactions in the multiplex reaction yielded a positive amplification result using the criteria set forth immediately below. More particularly, negative amplification results for the *S. aureus* and mecA amplification reactions required positive amplification of the internal control nucleic acid to be reported as valid. Scoring of the internal control amplification reaction was only relevant when the two other analytes yielded negative results. Negative results for all three reactions would indicate failure of an amplification reaction, as may occur, for example, if a reaction component was omitted or the reaction was strongly inhibited.

Generally speaking, a positive amplification result indicating the presence of one of the analytes in a multiplex reaction was determined when two conditions were met. First, the magnitude of the difference between the minimum and maximum fluorescence signals measured during the amplification reaction for that analyte must have exceeded a predetermined threshold value. Second, the TTime value determined for that analyte in the multiplex reaction must have occurred within a predetermined range. When both criteria were met for one of analytes in the multiplex amplification reaction, the analyte was determined to be present.

The positive signal criteria were chosen to be different for each of the three analytes in the multiplex amplification reaction. The *S. aureus* 23S DNA target was scored as being present when the range of the fluorescent signal during the reaction period was greater than 5,000, and when the TTime value was less than or equal to 20.65 minutes. The mecA DNA target was scored as being present when the range of the fluorescent signal during the reaction period was greater than 2,500, and when the TTime value was less than or equal to 32.8 minutes. Finally, the internal control was regarded as positive when the range of the fluorescent signal during the reaction period was greater than 5,000. There was no TTime threshold due to the high variability in amplification for this analyte.

Figure 3A:
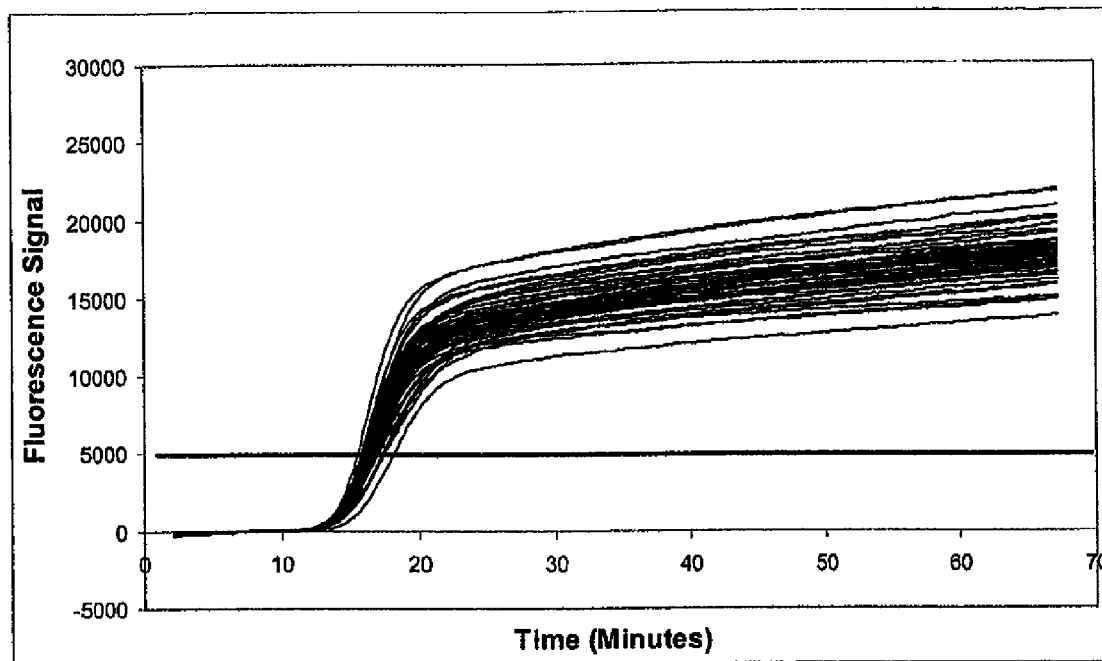
FIGS. 3A-3B are graphical presentations of real-time run curves for amplification of the S. aureus marker (panel A) and of the mecA marker (panel B) in reactions preformed using 160 CFU of MSSA and 100,000 CFU each of S. epidermidis and S. haemolyticus bacteria. The vertical axes show fluorescent signals, measured in RFU, for 52 amplification reactions. The horizontal lines drawn at 5,000 RFU (panel A) and at 2,500 RFU (panel B) on the vertical axes represent partial criteria used for determining positive amplification results.
Figure 3B:
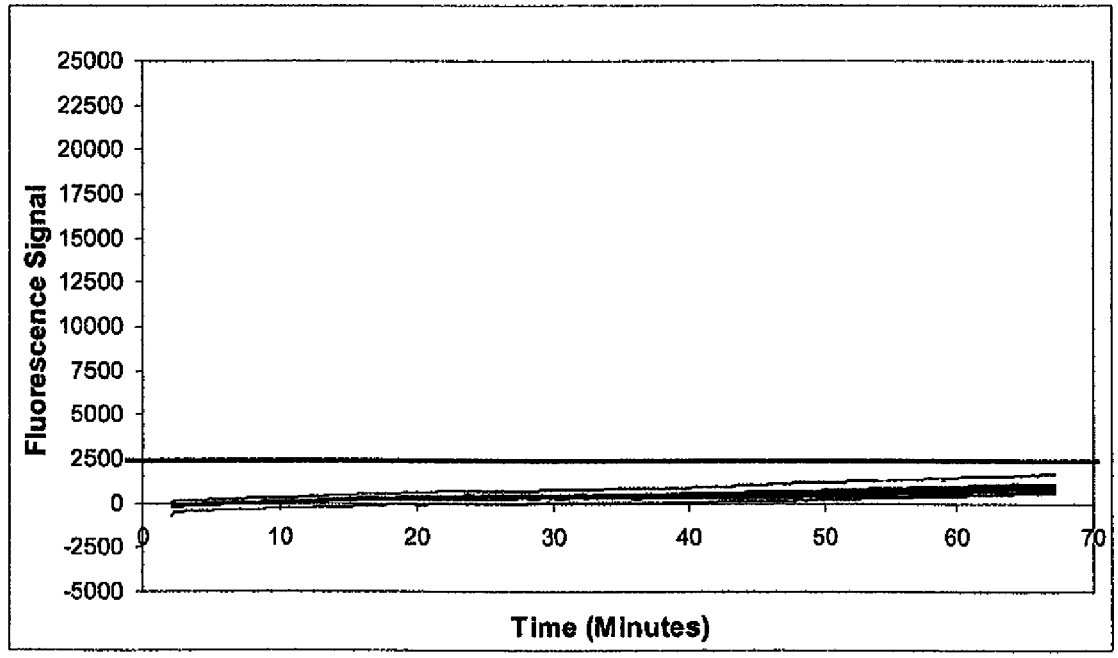

FIGS. 1-3 show representative results from the real-time nucleic acid amplification reactions. FIGS. 1A-1B present raw fluorescence results from time-dependent monitoring of *S. aureus* 23S rDNA (panel A) and mecA DNA (panel B) amplicon synthesis in samples containing low levels of MRSA challenged with high levels of methicillin-sensitive coagulase-negative *staphylococcus* bacteria. FIGS. 2A-2B present raw fluorescence results from time-dependent monitoring of *S. aureus* 23S rDNA (panel A) and mecA DNA (panel B) amplicon synthesis in samples containing low levels of MRSA challenged with high levels of MSSA bacteria. FIGS. 3A-3B present representative raw fluorescence results from time-dependent monitoring of *S. aureus* 23S rDNA (panel A) and mecA DNA (panel B) amplicon synthesis in samples containing low levels of MSSA challenged with high levels of methicillin-sensitive coagulase-negative *staphylococcus* bacteria. In all trials appearing in this latter set of graphs, the *S. aureus* target was detected and the mecA target was not detected, again as expected. In every instance, the difference between the minimum and maximum fluorescence signals measured during an amplification reaction represented in FIGS. 1-3 met the acceptance criteria. Accordingly, although each reaction gave a valid positive amplification result for the internal control, it was unnecessary to consult the internal control results to validate the procedures. Table 8 quantifies the results obtained for all samples that underwent testing.

TABLE 8

Summary of MRSA and MSSA Identification Under Challenge Conditions

| Sample | Number of Trials | Correct Identification | % Correct Identification |
|---|---|---|---|
| MRSA challenged with *S. epidermidis* and *S. haemolyticus* | 104 | 103 | 99% |
| MRSA challenged with MSSA | 101 | 100 | 99% |
| MSSA challenged with *S. epidermidis* and *S. haemolyticus* | 104 | 104 | 100% |

A multiplex amplification system essentially as described above was used for testing a collection of clinical samples (nasal swabs) that had been demonstrated to be negative for MRSA using gold standard microbiological techniques. Because the clinical samples contained complex mixtures of bacteria (e.g., MRSA, MSSA, MR-CoNS, etc.), it was possible to detect the two nucleic acid targets (i.e., *S. aureus* 23S rDNA and mecA targets) originating from different organisms. As a result, it was possible to detect the *S. aureus* 23S rDNA target sequence originating from MSSA present in the sample, and to detect the mecA target sequence originating from MR-CoNS bacteria present in the same sample. Concluding that the presence of both targets in the sample indicated the presence of MRSA would be an error in this instance. Thus, co-infections present a challenge for analysis of clinical samples using independent target nucleic acids. Accordingly, there was a need to control or eliminate the number of false-positive MRSA assignments when analyzing clinical samples.

The following Example describes results obtained using clinical samples (i.e., nasal swab samples) established by independent analysis to be MRSA-negative. Three swab samples were obtained from individual participants. The first swab was subjected to gold standard microbiological testing to establish the presence or absence of MRSA bacteria. The second swab was stored in a frozen archive. The third swab was subjected to sample processing to isolate DNA, and the isolated DNA used as a source of templates for multiplex amplification of *S. aureus* 23S rDNA and mecA targets, essentially as described under Example 1.

Example 2

Real-Time Analysis of MRSA-Negative Clinical Samples

Fifty-five nasal swab samples negative for MRSA were tested in a multiplex real-time amplification system, and determinations of the presence or absence of the *S. aureus* and mecA target nucleic acids made essentially as described under Example 1. Real-time run curves were analyzed to determine indicia of amplification based on attainment of a threshold fluorescence value using MXPRO QPCR real-time analytical software (Stratagene; La Jolla, Calif.). Where Ct values were determined, the values were averaged and used for calculation of ΔCt values.

Figure 5A:
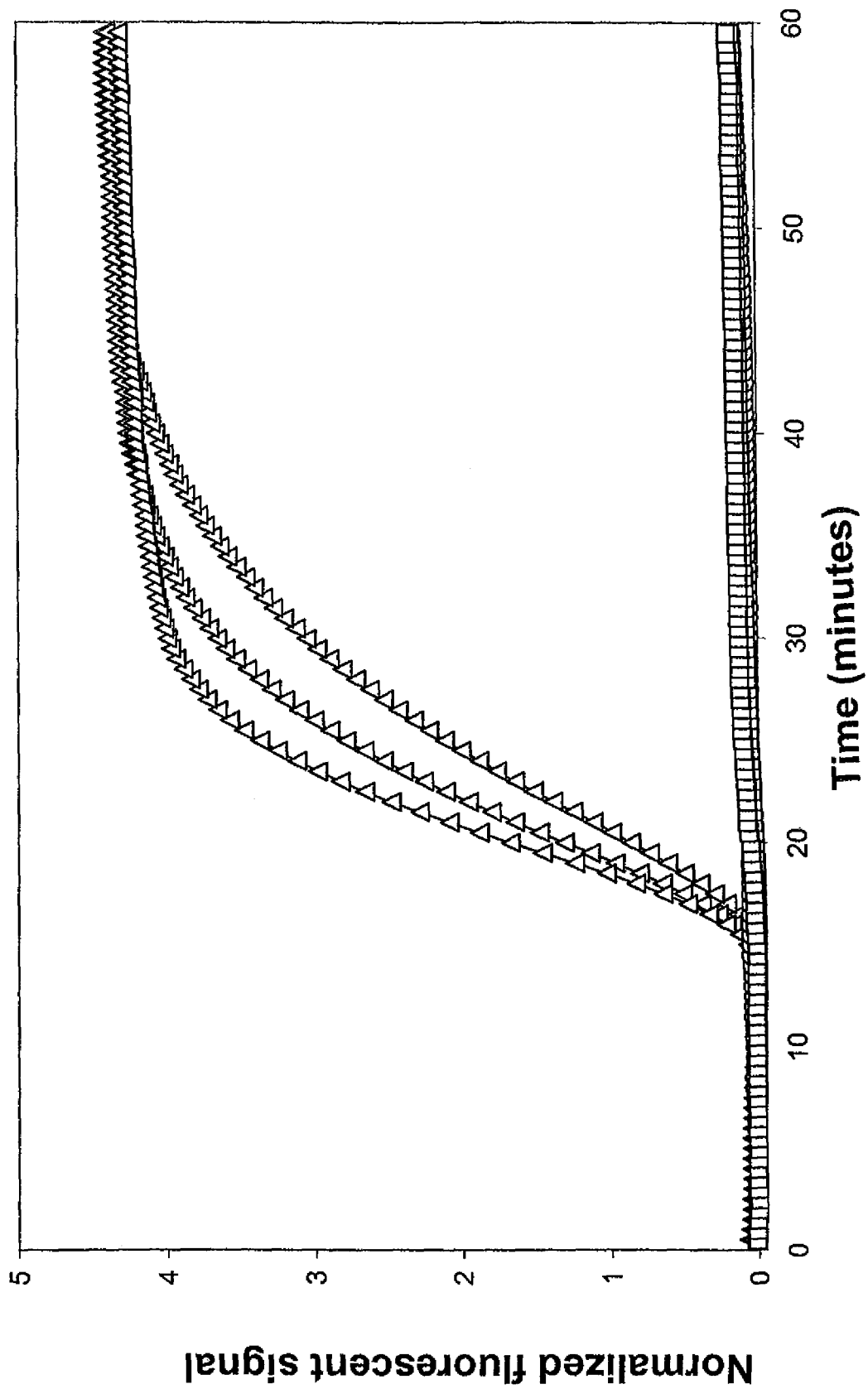
FIGS. 5A-5E are graphs presenting real-time run curves for multiplex amplification reactions carried out using negative and positive controls, as well as three different clinical samples established by microbiological testing to be MRSA-negatives. Each graph shows fluorescent signals measured as a function of time for *S. aureus* 23S rDNA (□), mecA (○), and internal control (Δ) nucleic acid targets. Panel A presents results for a negative control. Panel B presents results for an MRSA-positive control that does not include MSSA or MR-CoNS. Panel C presents results for sample 3136. Panel D presents results for sample 1253. Panel E presents results for sample 1238. Amplification reactions were performed in replicates of two or three, Notably, the y-axes of the control graphs show signal-to-noise values. The y-axes of graphs obtained using the clinical samples show raw fluorescence data.
Figure 5B:
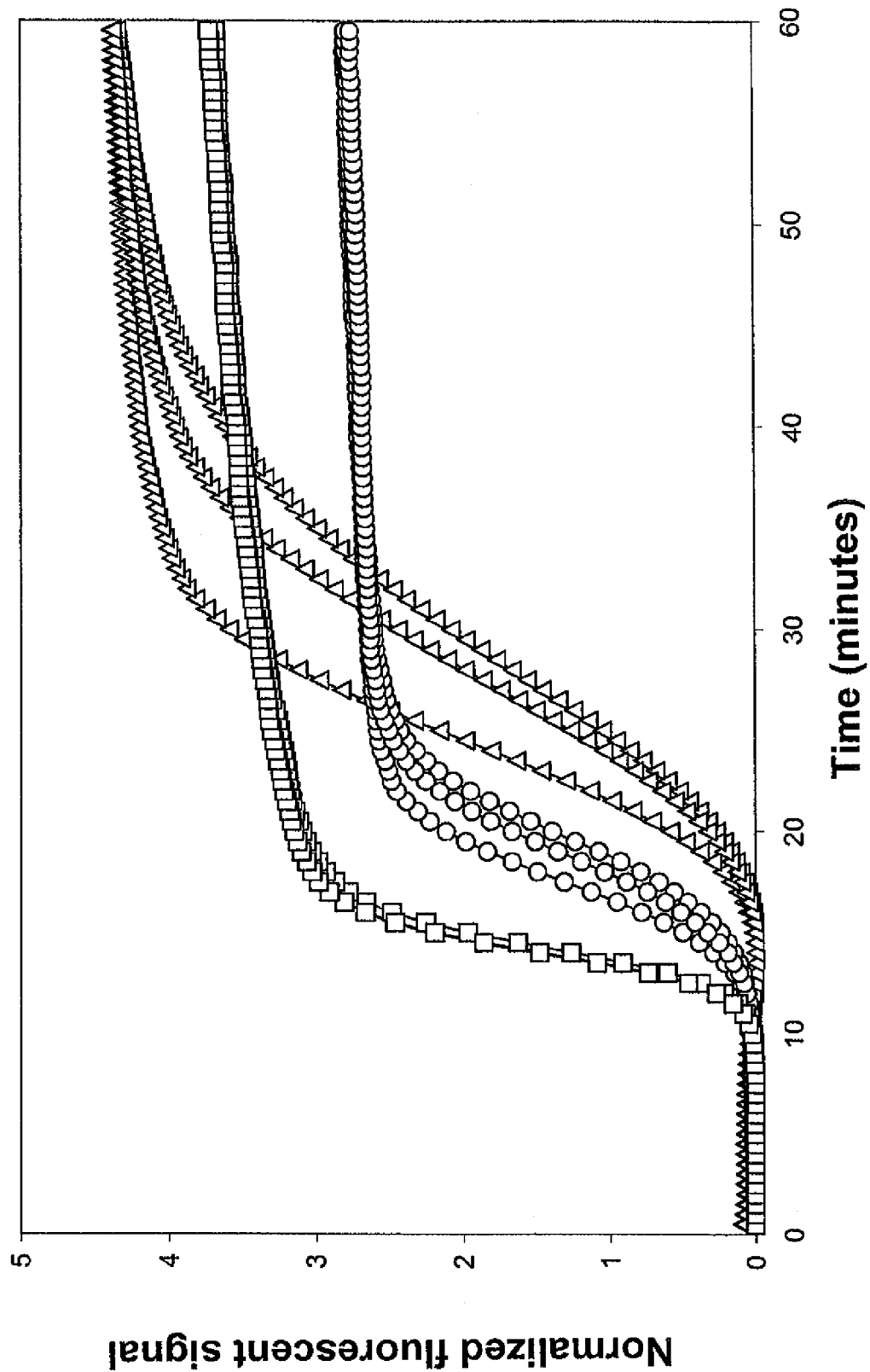
Figure 5C:
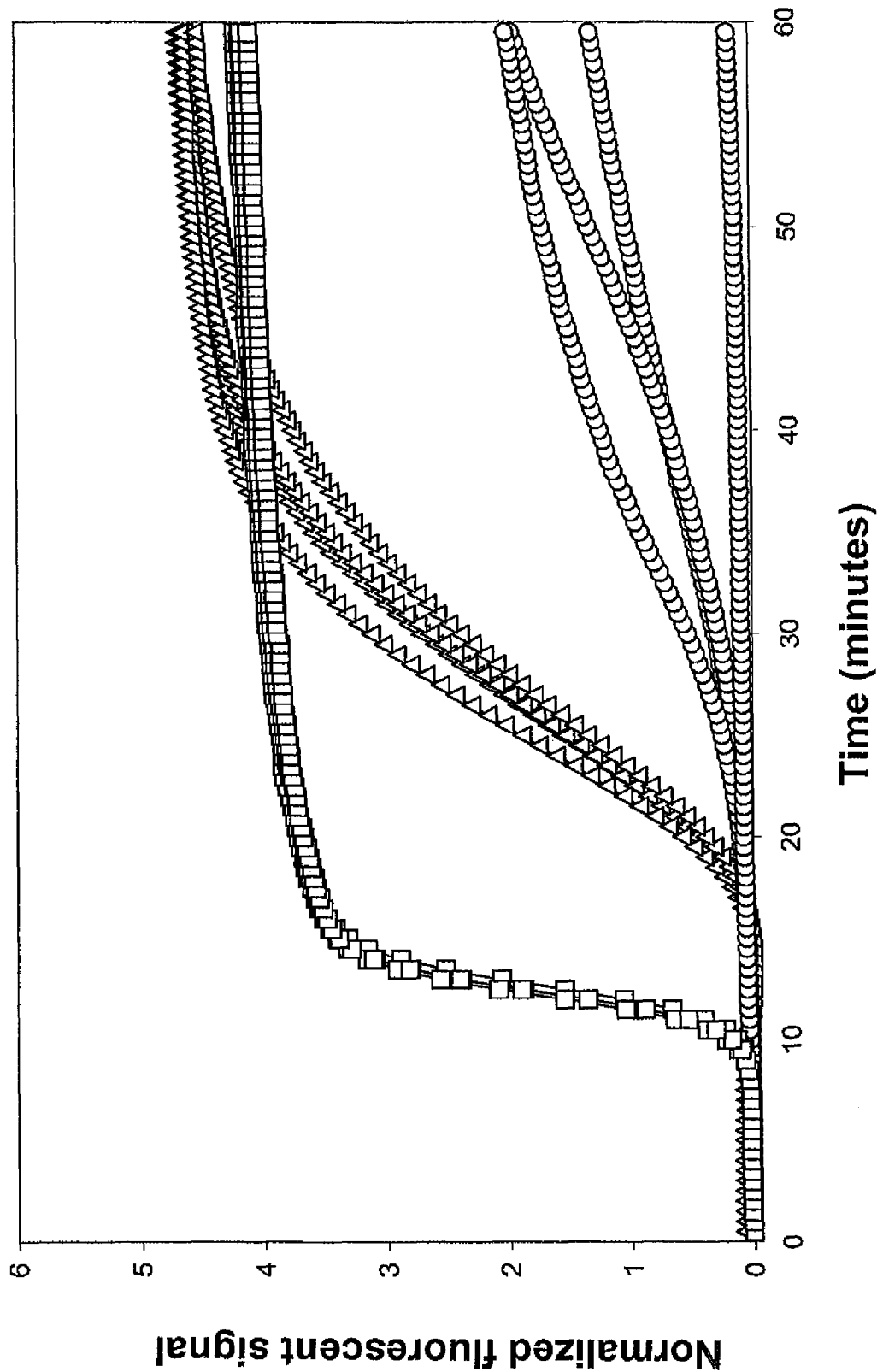
Figure 5D:
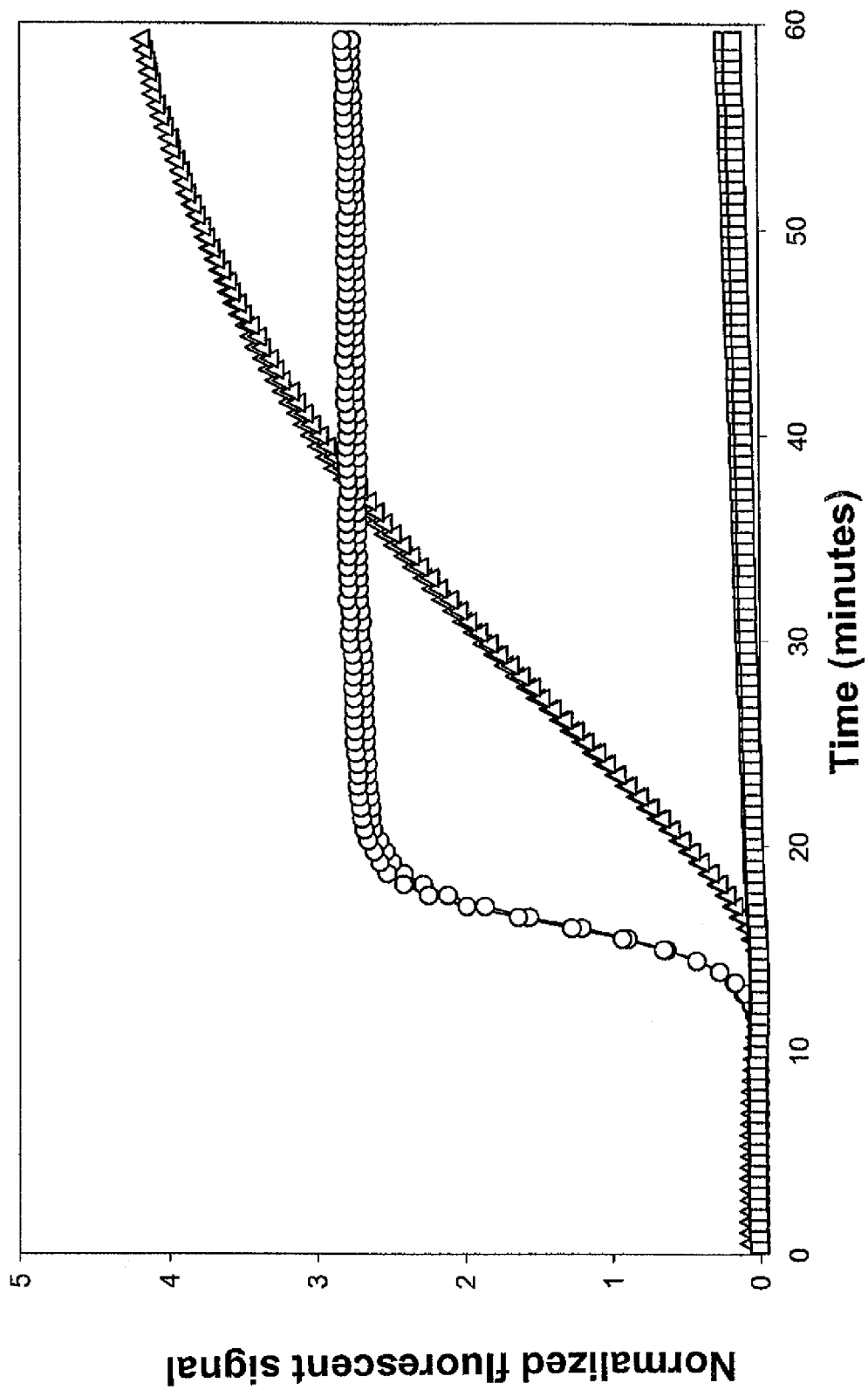
Figure 5E:
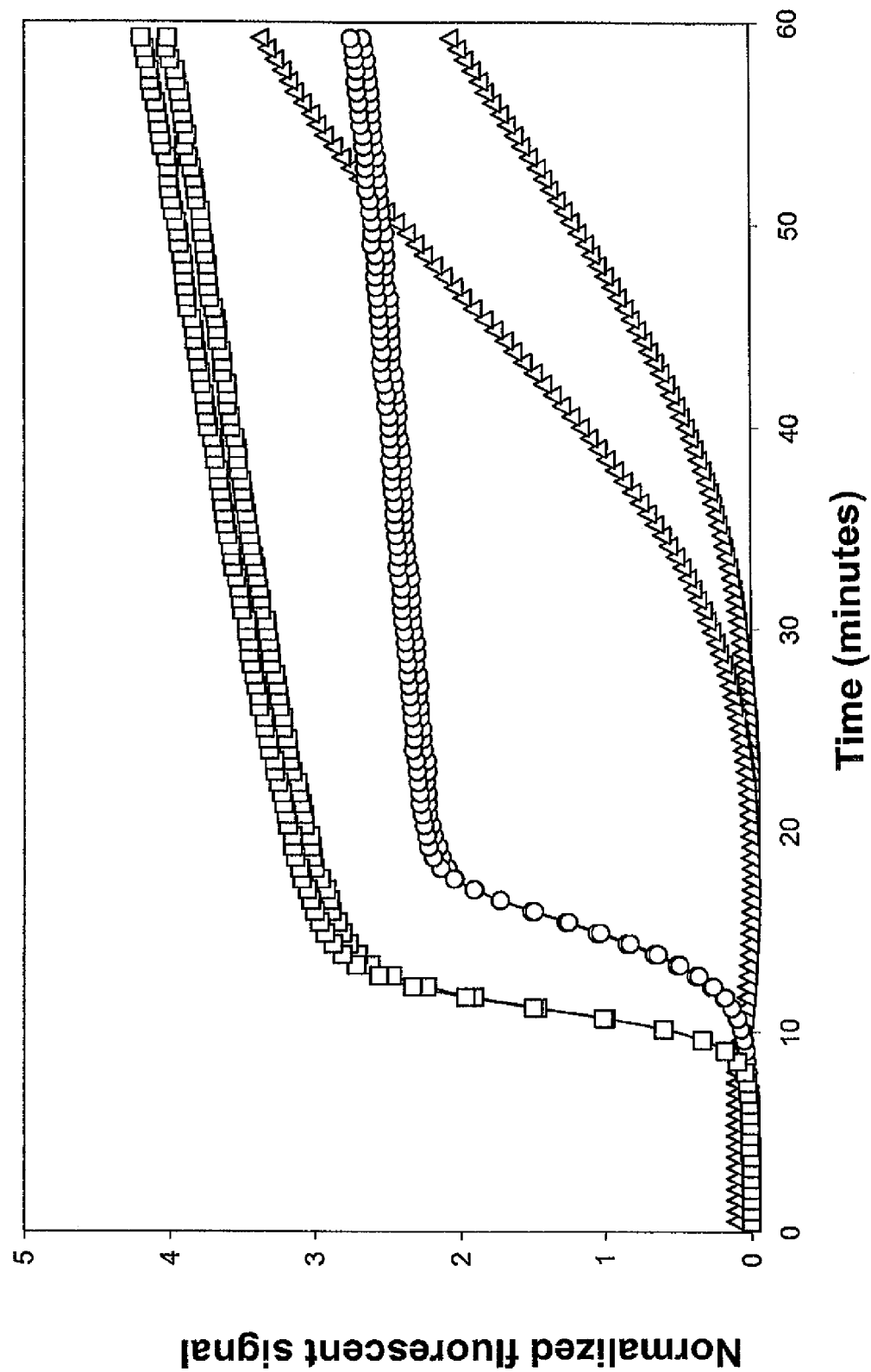

Representative run curves from the real-time amplification procedure are shown in FIGS. 5A-5E. All panels graphically depict results for amplification of internal control, *S. aureus* 23S rDNA, and mecA target sequences. Individual amplification reactions were scored as positive using acceptance criteria essentially as described under Example 1. FIG. 5A shows results for a negative control trial that did not include either *S. aureus* or mecA nucleic acids. Only the internal control signal showed evidence for amplification, as expected. FIG. 5B shows results for a positive MRSA control reaction (i.e., using about 500 cfu MRSA bacteria). In this instance, all of the *S. aureus*, mecA and internal control signals showed evidence for amplification. Notably, the controls shown in FIGS. 5A-5B were also useful for interpreting results presented under Example 3, below. FIG. 5C shows results wherein the *S. aureus* and internal control signals showed evidence for amplification, but the mecA signal was substantially delayed such that the criteria required for scoring a positive result were not met. The profile shown in this panel would not be characteristic of MRSA infection, but instead would be characteristic of infection by MSSA, possibly with minor amounts of mecA-containing bacteria other than *S. aureus*. FIG. 5D shows results wherein the mecA and internal control signals showed evidence for amplification, but the *S. aureus* signal did not. This profile would be characteristic of infection by MR-CoNS bacteria. FIG. 5E shows results wherein both the *S. aureus* and mecA signals showed evidence for amplification, with the internal control being positive, although somewhat delayed (e.g., as the result of robust amplification of the two other target sequences in the multiplex reaction). This profile would be characteristic of co-infection by MSSA and MR-CoNS bacteria. Results from all trials carried out using the known MRSA-negative clinical samples are summarized in Table 9,

TABLE 9

Qualitative Real-Time Testing of MRSA-Negative Clinical Samples

| Negative Sample No. | Sample Identifier | S. aureus | mecA | Internal Control | MRSA assignment |
|---|---|---|---|---|---|
| 1 | 1315 | negative | positive | positive | negative |
| 2 | 1424 | positive | positive | positive | positive |
| 3 | 3117 | negative | positive | positive | negative |
| 4 | 3136 | positive | negative | positive | negative |
| 5 | 3318 | negative | negative | positive | negative |
| 6 | 1246 | positive | negative | positive | negative |
| 7 | 3273 | negative | positive | positive | negative |
| 8 | 1253 | negative | positive | positive | negative |
| 9 | 1414 | negative | positive | positive | negative |
| 10 | 1248 | negative | positive | positive | negative |
| 11 | 3196 | negative | positive | positive | negative |
| 12 | 1435 | negative | negative | positive | negative |
| 13 | 1438 | positive | negative | positive | negative |
| 14 | 1238 | positive | positive | positive | positive |
| 15 | 1314 | positive | positive | positive | positive |
| 16 | 3118 | positive | positive | positive | positive |
| 17 | 1234 | negative | positive | positive | negative |
| 18 | 1242 | negative | positive | positive | negative |
| 19 | 1262 | negative | positive | positive | negative |
| 20 | 3078 | positive | negative | positive | negative |
| 21 | 1413 | negative | negative | positive | negative |
| 22 | 1313 | negative | negative | positive | negative |
| 23 | 1434 | negative | positive | positive | negative |
| 24 | 1317 | negative | positive | positive | negative |
| 25 | 3454 | negative | positive | positive | negative |
| 26 | 1240 | negative | positive | positive | negative |
| 27 | 3466 | negative | positive | positive | negative |
| 28 | 3099 | negative | positive | positive | negative |
| 29 | 3102 | negative | positive | positive | negative |
| 30 | 1427 | positive | positive | positive | positive |
| 31 | 3264 | negative | positive | positive | negative |
| 32 | 3134 | negative | positive | positive | negative |
| 33 | 3109 | negative | positive | positive | negative |
| 34 | 3105 | negative | negative | positive | negative |
| 35 | 1244 | negative | positive | negative | negative |
| 36 | 3097 | negative | negative | positive | negative |
| 37 | 3278 | negative | positive | negative | negative |
| 38 | 3148 | negative | positive | negative | negative |
| 39 | 1241 | negative | negative | negative | negative |
| 40 | 3307 | negative | negative | positive | negative |
| 41 | 3112 | negative | negative | positive | negative |
| 42 | 3471 | negative | positive | positive | negative |
| 43 | 3123 | negative | positive | positive | negative |
| 44 | 1235 | negative | positive | positive | negative |
| 45 | 1419 | negative | positive | positive | negative |
| 46 | 1261 | negative | positive | negative | negative |
| 47 | 3459 | negative | positive | negative | negative |
| 48 | 3138 | negative | positive | negative | negative |
| 49 | 1265 | negative | positive | negative | negative |
| 50 | 1418 | positive | positive | negative | positive |
| 51 | 3086 | negative | positive | positive | negative |
| 52 | 3455 | negative | negative | negative | negative |
| 53 | 3121 | negative | positive | positive | negative |
| 54 | 3276 | positive | positive | positive | positive |
| 55 | 3452 | negative | negative | positive | negative |

The results appearing in Table 9 identified seven MRSA-negative clinical samples (i.e., 1424, 1238, 1314, 3118, 1427, 1418 and 3276) that were positive for both the *S. aureus* and mecA target nucleic acids, a profile that would also be expected for MRSA bacteria. However, clinical samples identified as MRSA-positive based simply on the presence of the *S. aureus* and mecA nucleic acids as summarized in Table 9 would be "false-positives." This is because all clinical samples used for obtaining the results summarized in Table 9 had been established to be MRSA-negative based on microbiological characterization.

The Ct values of the seven false-positive samples are summarized in Table 10. Imposing an arbitrary requirement for ΔCt values to exceed an arbitrary threshold cut-off of −2 minutes would have eliminated 4 of 7 false-positives, thereby improving the results. The basis for selection of the arbitrary threshold is illustrated under Example 4.

TABLE 10

Assessment of Potential False-Positive Samples

| Sample No. | S. aureus | mecA | Internal Control | Ct(Sau) (min) | Ct(mecA) (min) | ΔCt (min) |
|---|---|---|---|---|---|---|
| 1424 | positive | positive | positive | 10.2 | 16.6 | −6.4 |
| 1238 | positive | positive | positive | 9.7 | 12.9 | −3.2 |
| 1314 | positive | positive | positive | 13.0 | 20.0 | −7.0 |
| 3118 | positive | positive | positive | 13.3 | 14.4 | −1.1 |
| 1427 | positive | positive | positive | 10.0 | 20.14 | −10.1 |
| 1418 | positive | positive | negative | 12.3 | 13.8 | −1.5 |
| 3276 | positive | positive | positive | 13.5 | 14.0 | −0.5 |

The following Example describes procedures employing clinical samples that had been first identified as MRSA-positive using gold standard microbiological testing. In the procedure described below, nucleic acids were isolated from nasal swab samples, and the isolated nucleic acids then used in the above-described real-time multiplex amplification procedure.

Example 3

Real-Time Analysis of MRSA-Positive Clinical Samples

Fifty nasal swab samples positive for MRSA were tested in a multiplex real-time amplification system, and determinations of the presence or absence of the S. aureus and mecA target nucleic acids made essentially as described under Example 1. Reactions were carried out in replicates of two or three. Indicia of amplification (i.e., Ct values) were determined as described under the preceding Example. Where Ct values were determined, the values were averaged and used for calculation of ΔCt values.

Figure 6A:
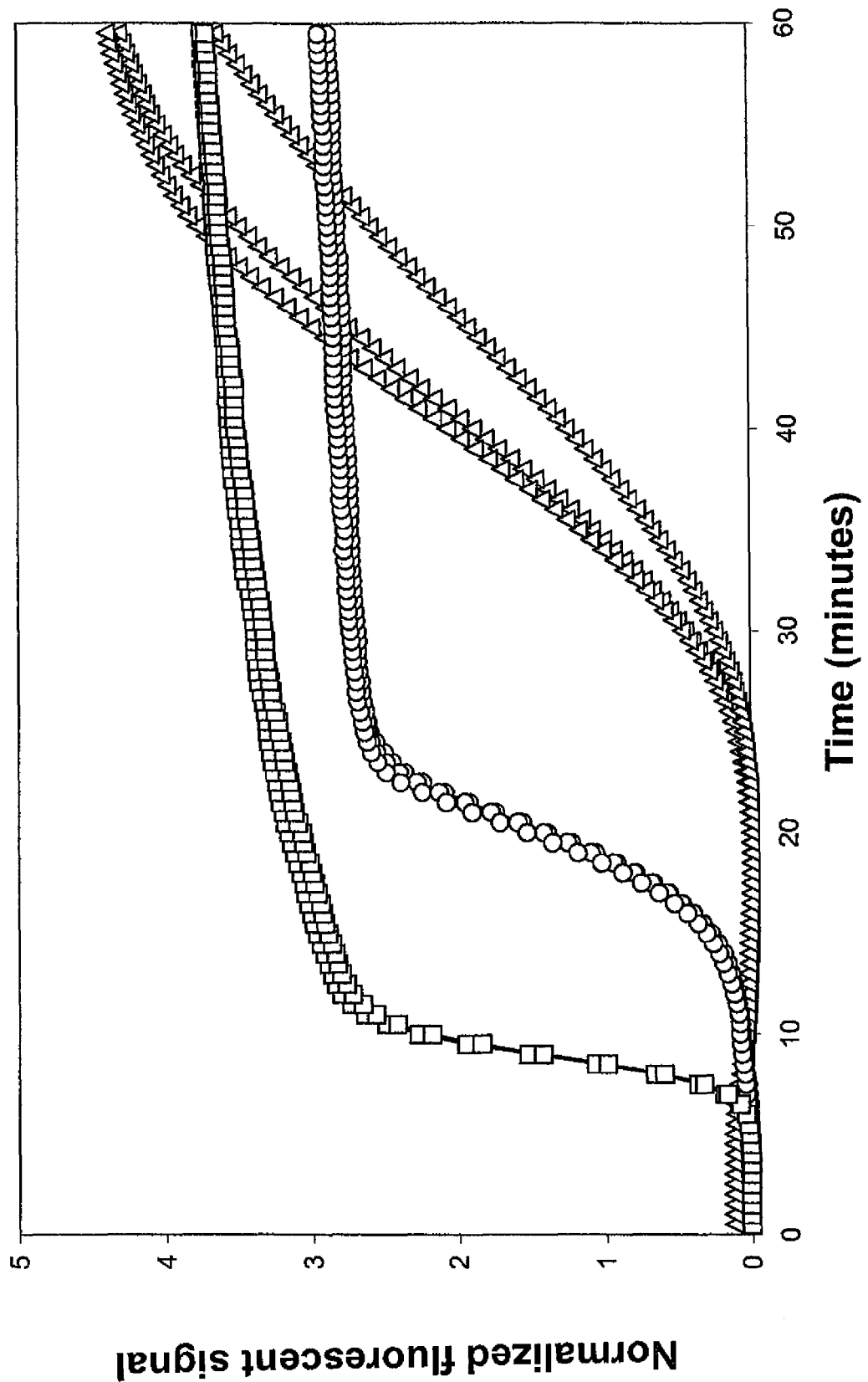
FIGS. 6A-6C are graphs presenting real-time run curves for multiplex amplification reactions carried out using three different clinical samples established by microbiological testing to be MRSA-positive. Each graph shows fluorescent signals measured as a function of time for *S. aureus* 23S rDNA (□), mecA (○), and internal control (Δ) nucleic acid targets. Panel A presents results for sample 1630. Panel B presents results for sample 2115. Panel C presents results for sample 1301. Amplification reactions were performed in replicates of two or three. Notably, the y-axes in all graphs show signal-to-noise values.
Figure 6B:
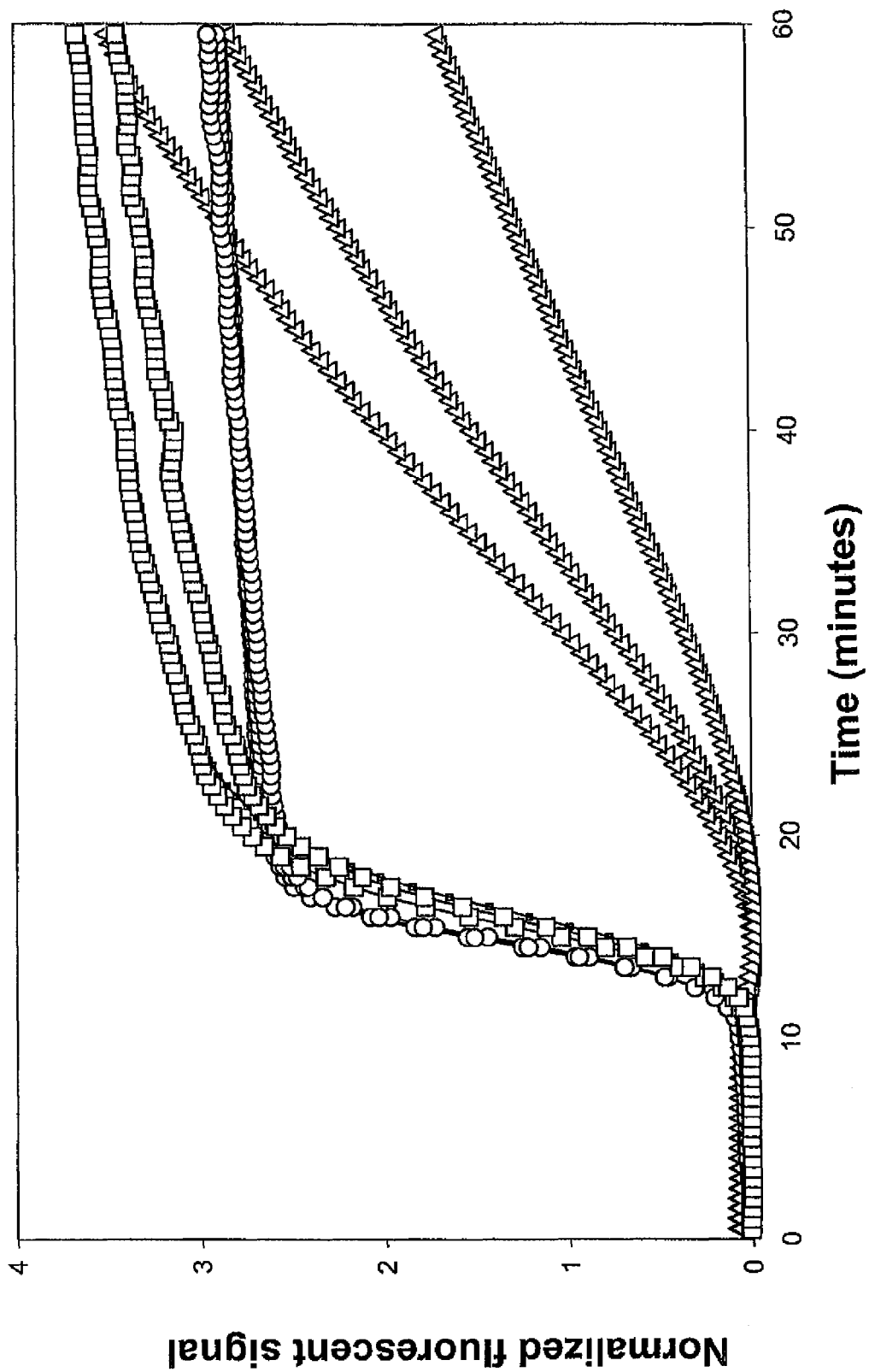
Figure 6C:
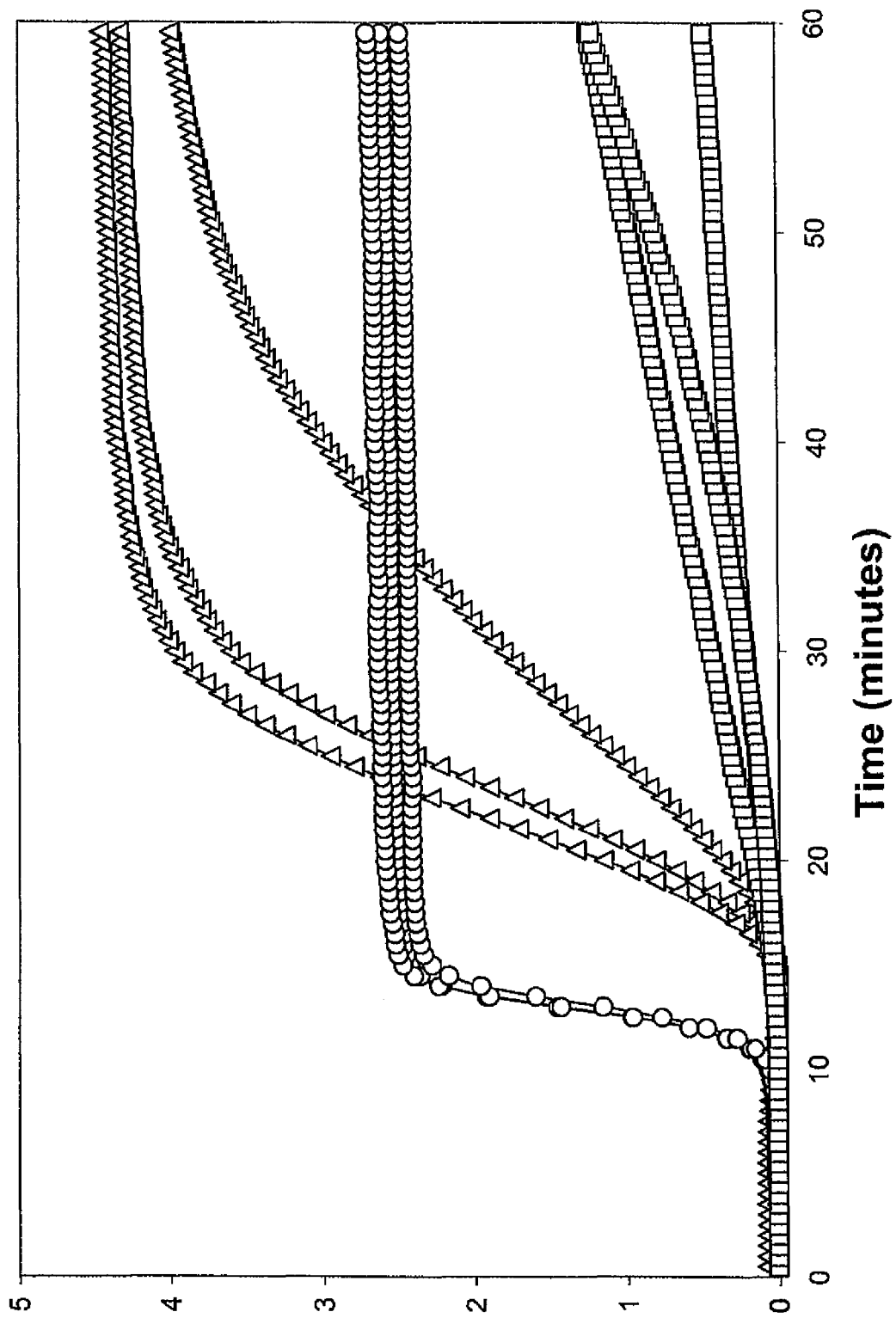

Representative run curves from these procedures are shown in FIGS. 6A-6C. FIG. 6A shows results wherein all of the S. aureus, mecA and internal control signals showed evidence for amplification. The average ΔCt value calculated for this trial was −7.7 minutes. As discussed below, a ΔCt value of this magnitude was consistent with a sample representing co-infection by MRSA and MSSA. FIG. 6B also shows results wherein all of the S. aureus, mecA and internal control signals showed evidence for amplification. However, in contrast to the MRSA-positive control trial illustrated in FIG. 5B, the mecA signal was the first to emerge from background levels. As a consequence, the ΔCt value calculated for this trial was 0.8 minutes (i.e., a positive number). This result was consistent with a sample representing co-infection by MRSA and MR-CoNS. FIG. 6C shows results wherein the mecA and internal control signals showed evidence for robust amplification, but wherein the S. aureus signal was delayed to the point that criteria for a positive score were not met. Despite the fact that the sample used to obtain this result had been identified as MRSA-positive by gold standard microbiological testing, the conclusion based on kinetic analysis of real-time amplification results did not agree. More particularly, because it was not possible to calculate a Ct(Sau) value from the real-time run curves, the sample was classified as MRSA-negative.

Results from all trials carried out using clinical samples identified as MRSA-positive by preliminary microbiological testing are summarized in Table 11. As indicated in the table, three samples initially identified as MRSA-positive by microbiological testing (i.e., samples 3076, 1301 and 3028) yielded negative results for amplification of the S. aureus 23S rDNA target nucleic acid. One of these samples (i.e., 3028) also failed to show evidence for amplification of the mecA target nucleic acids. Each of the three discordant samples was subjected to rigorous follow-up analysis using a combination of microbiological and molecular (e.g., DNA sequencing) techniques. Results from these analyses confirmed that the original MRSA assignment had been a false-positive assignment. This illustrated how the real-time assay correctly identified MRSA in clinical samples, and reduced false-positive results that occurred in other testing systems. Column 5 in the table confirms that the remaining truly MRSA-positive samples were correctly identified using the real-time assay. Thus, none of the MRSA-containing samples were misidentified as false-negatives. Three different clinical samples (i.e., samples 1630, 1237 and 3387) yielded real-time run curves where the separations between the determined Ct values were substantially greater than for other trials listed in the table. These results could have been explained by co-infection of MRSA with MSSA. The internal control signal was uniformly positive for all of the trials represented in Table 11, and so that assay parameter is omitted from the presentation, As above, ΔCt values were calculated by subtracting the value of Ct(mecA) from Ct(S. aureus).

TABLE 11

Qualitative Real-Time Testing of MRSA-Positive Clinical Samples

| Positive Sample No. | Sample ID | S. aureus | mecA | MRSA | Ct(Sau) (min) | Ct(mecA) (min) | ΔCt (min) |
|---|---|---|---|---|---|---|---|
| 1 | 1311 | positive | positive | positive | 11.4 | 12.6 | −1.3 |
| 2 | 1630 | positive | positive | positive | 7.2 | 14.9 | −7.7 |
| 3 | 1441 | positive | positive | positive | 8.1 | 9.5 | −1.3 |
| 4 | 2139 | positive | positive | positive | 11.7 | 12.6 | −0.8 |
| 5 | 2111 | positive | positive | positive | 10.0 | 11.1 | −1.1 |
| 6 | 2115 | positive | positive | positive | 13.0 | 12.2 | 0.8 |
| 7 | 1450 | positive | positive | positive | 12.6 | 12.1 | 0.4 |
| 8 | 1633 | positive | positive | positive | 13.3 | 14.1 | −0.8 |
| 9 | 1233 | positive | positive | positive | 11.5 | 11.8 | −0.3 |
| 10 | 2113 | positive | positive | positive | 14.0 | 10.9 | 3.1 |
| 11 | 2114 | positive | positive | positive | 10.1 | 11.6 | −1.5 |
| 12 | 1237 | positive | positive | positive | 7.9 | 11.7 | −3.8 |
| 13 | 1442 | positive | positive | positive | 9.2 | 11.4 | −2.2 |
| 14 | 2160 | positive | positive | positive | 10.9 | 9.2 | 1.7 |
| 15 | 2162 | positive | positive | positive | 11.7 | 13.2 | −1.5 |
| 16 | 1409 | positive | positive | positive | 11.7 | 12.5 | −0.8 |
| 17 | 2109 | positive | positive | positive | 8.8 | 9.7 | −0.9 |

TABLE 11-continued

Qualitative Real-Time Testing of MRSA-Positive Clinical Samples

| Positive Sample No. | Sample ID | S. aureus | mecA | MRSA | Ct(Sau) (min) | Ct(mecA) (min) | ΔCt (min) |
|---|---|---|---|---|---|---|---|
| 18 | 2136 | positive | positive | positive | 10.3 | 9.7 | 0.5 |
| 19 | 2158 | positive | positive | positive | 12.6 | 14.2 | −1.6 |
| 20 | 1425 | positive | positive | positive | 11.3 | 11.9 | −0.7 |
| 21 | 1257 | positive | positive | positive | 11.2 | 11.9 | −0.6 |
| 22 | 2103 | positive | positive | positive | 8.9 | 10.3 | −1.3 |
| 23 | 2105 | positive | positive | positive | 9.7 | 11.1 | −1.4 |
| 24 | 2112 | positive | positive | positive | 11.6 | 12.6 | −1.1 |
| 25 | 1410 | positive | positive | positive | 10.6 | 10.6 | 0.1 |
| 26 | 2104 | positive | positive | positive | 9.0 | 8.2 | 0.8 |
| 27 | 1453 | positive | positive | positive | 13.3 | 14.3 | −1.0 |
| 28 | 1345 | positive | positive | positive | 8.0 | 9.7 | −1.7 |
| 29 | 1255 | positive | positive | positive | 9.0 | 9.6 | −0.6 |
| 30 | 2108 | positive | positive | positive | 9.0 | 10.5 | −1.5 |
| 31 | 1304 | positive | positive | positive | 9.5 | 10.2 | −0.7 |
| 32 | 3006 | positive | positive | positive | 13.4 | 12.2 | 1.2 |
| 33 | 1348 | positive | positive | positive | 14.6 | 12.4 | 2.2 |
| 34 | 1384 | positive | positive | positive | 9.3 | 9.3 | −0.1 |
| 35 | 3036 | positive | positive | positive | 11.1 | 11.9 | −0.9 |
| 36 | 3076 | negative | positive | negative | ND | 12.7 | ND |
| 37 | 1332 | positive | positive | positive | 11.9 | 12.4 | −0.5 |
| 38 | 3398 | positive | positive | positive | 11.6 | 11.4 | 0.2 |
| 39 | 3342 | positive | positive | positive | 12.7 | 10.8 | 1.9 |
| 40 | 3348 | positive | positive | positive | 11.9 | 11.1 | 0.8 |
| 41 | 3389 | positive | positive | positive | 13.9 | 12.7 | 1.1 |
| 42 | 3387 | positive | positive | positive | 11.8 | 21.5 | −9.6 |
| 43 | 1388 | positive | positive | positive | 8.4 | 8.2 | 0.2 |
| 44 | 1301 | negative | positive | negative | ND | 11.0 | ND |
| 45 | 3028 | negative | negative | negative | ND | ND | ND |
| 46 | 3060 | positive | positive | positive | 9.0 | 10.5 | −1.5 |
| 47 | 3014 | positive | positive | positive | 11.0 | 12.4 | −1.5 |
| 48 | 3301 | positive | positive | positive | 9.9 | 9.5 | 0.4 |
| 49 | 3374 | positive | positive | positive | 12.0 | 12.4 | −0.4 |
| 50 | 3320 | positive | positive | positive | 8.7 | 9.9 | −1.1 |

ND = not determinable

The foregoing illustrated how MRSA bacteria could be detected by real-time amplification of: (1) a first target specific for S. aureus but not CoNS bacteria (e.g., a 23S rDNA sequence specific for S. aureus); and (2) a second target that was specific for a marker of methicillin resistance (e.g., a mecA target sequence) in a multiplex amplification reaction. While this approach accurately detected 100% of clinical samples that were truly MRSA-positive (see Table 11), there also were detected some false-positive samples that were truly negative for MRSA (see Table 10). These false-positives likely resulted from co-infections of MSSA with MR-CoNS bacteria. Also presented above is evidence showing how kinetic analysis of the real-time results could resolve: mixtures of MRSA and MSSA; mixtures of MRSA and MR-CoNS; and mixtures of MSSA and MR-CoNS. Below there is described a general approach for minimizing the incidence of false-positives.

The exact nature of a real-time amplification reaction, including indicia of amplification (e.g., Ct values) determined from a run curve, clearly depends on many variables. For example, reaction conditions such as temperature and reagent concentrations can dramatically affect run curve profiles. Different curve analysis algorithms for determining the point at which a predetermined reaction parameter is achieved also will give different numerical values when applied to analysis the same run curve. Nonetheless, we have discovered that it is possible to relate indicia of amplification for the S. aureus-specific target (e.g., S. aureus 23S rDNA) and for the target specific for a marker of methicillin resistance (e.g., mecA DNA), and establish a threshold value from this relationship. This threshold value advantageously reduced the incidence of false-positive MRSA identifications at the expense of a slight increase in the number of false-negative identifications.

The following Example describes selection of an arbitrary threshold for designating MRSA-positive clinical samples, and for reducing the number of false-positive identifications arising from samples that include mixtures of MSSA and MR-CoNS. When an empirically determined threshold cut-off was applied to the experimental results obtained under Examples 2-3, the number of false-positive assignments was substantially reduced.

Example 4

Selection of an Arbitrary Threshold for Minimizing False-Positive Results

Figure 7A:
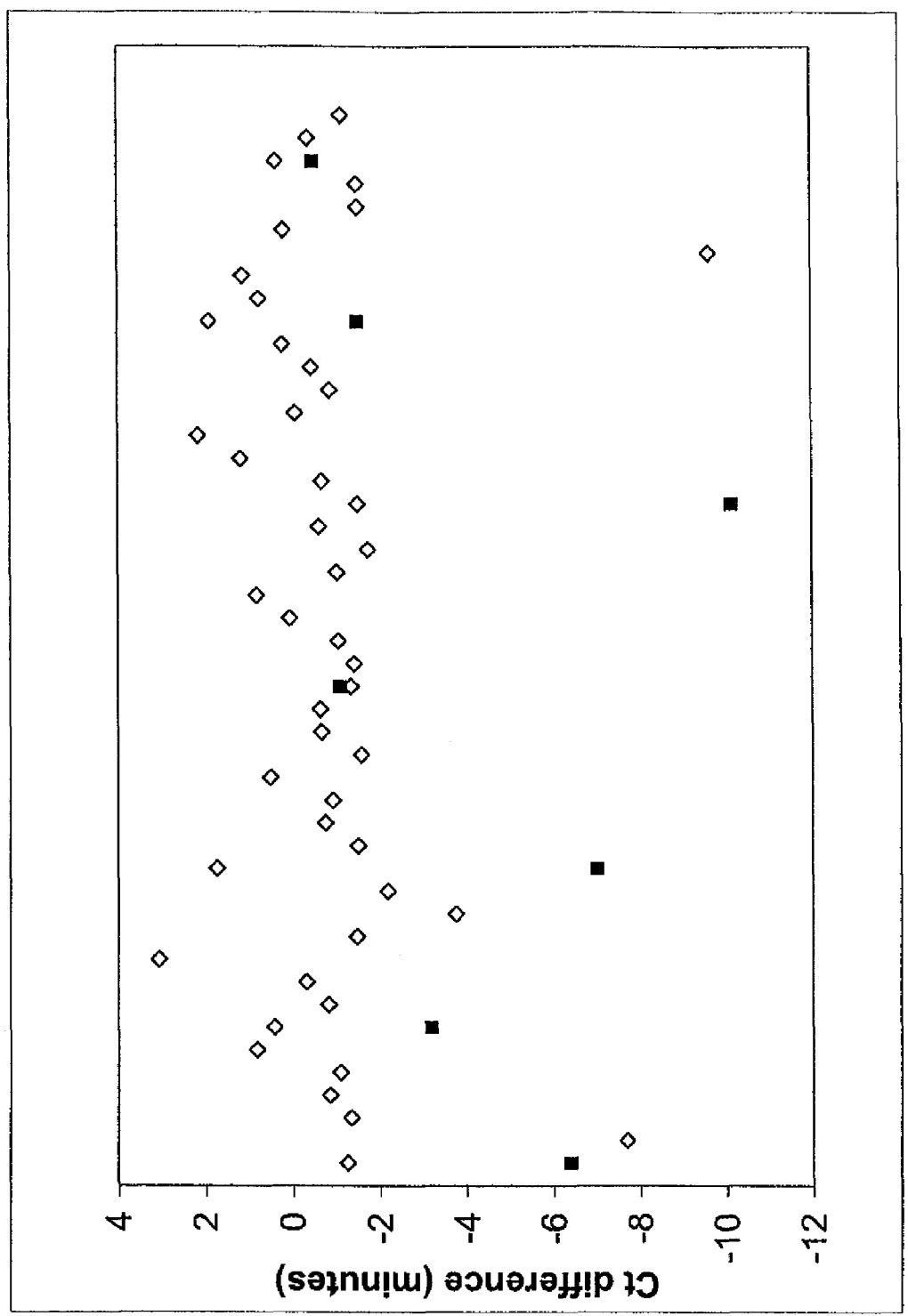
FIGS. 7A-7B are graphic plots illustrating ΔCt values for data points representing clinical samples initially identified by microbiological testing as MRSA-positive (open diamonds) and MRSA-negative (filled squares). Panel A shows the distribution of ΔCt values for all data points that gave positive amplification results for both a *S. aureus*-specific target sequence (i.e., a 23S rDNA sequence) and a methicillin-resistance marker (i.e., a mecA sequence). Panel B shows the same data points presented in panel A, but further includes an arbitrary threshold cutoff drawn at ΔCt=−2 minutes.
Figure 7B:
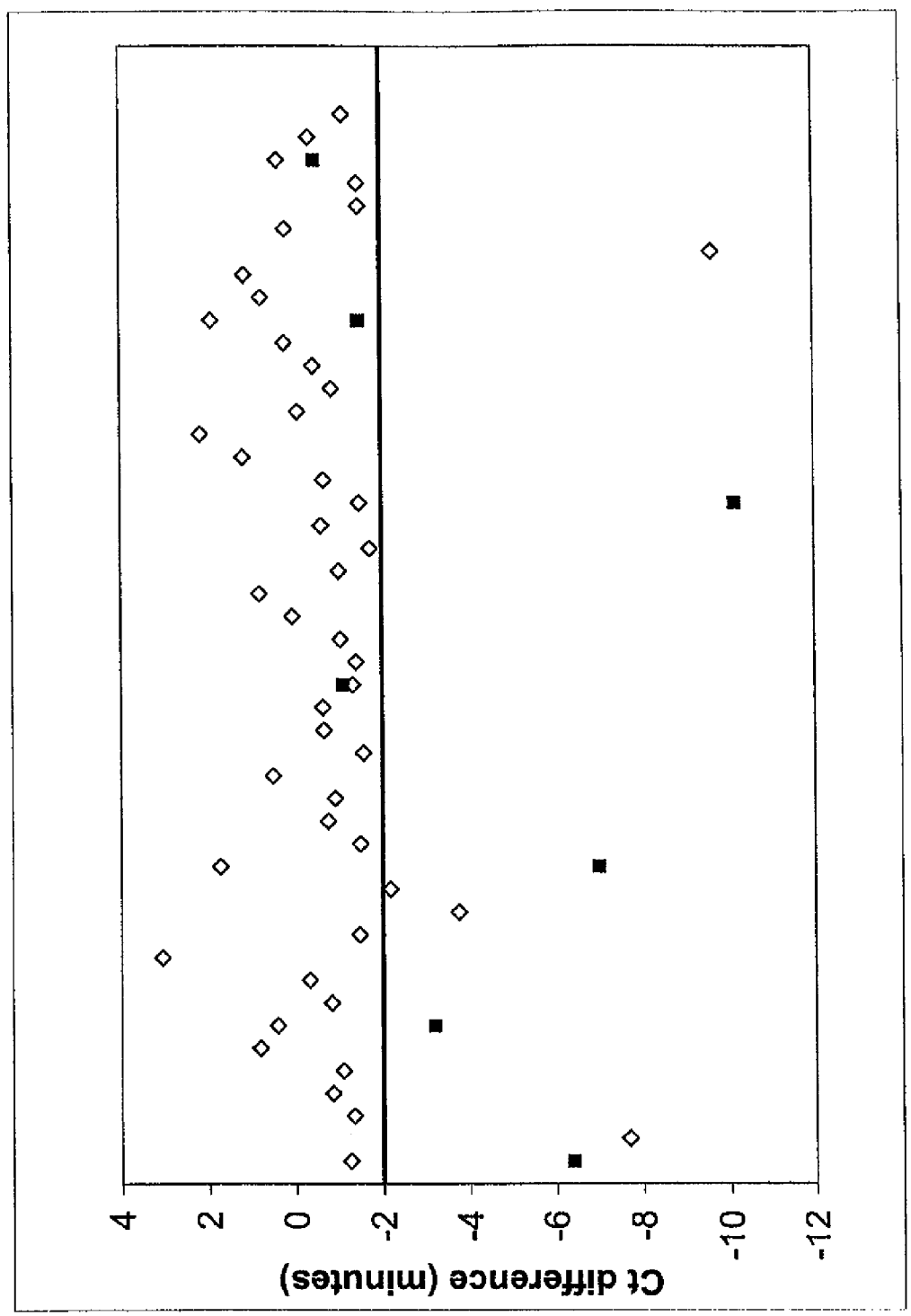

Collected results from Examples 2-3 were plotted in FIG. 7 to visualize ΔCt values for the distribution of results obtained using clinical samples containing the S. aureus and mecA target nucleic acids. Generally speaking, the plotted data included results from a plurality of clinical samples confirmed MRSA-positive by microbiological testing, as well as a plurality of false-positive results. The false-positive results were likely due to clinical samples representing co-infections of MSSA with MR-CoNS. In the instance illustrated by the two panels in FIG. 7, ΔCt values from 47 positive samples analyzed in Example 3 were included in the plot. Notably, of the 50 nasal swab samples tested in that Example, three samples were proven to be truly negative, and so were excluded from FIG. 7. Also included in the plot are the 7 false-positive results from Example 2, as summarized in Table 10. These results were obtained following analysis of 55 MRSA-negative clinical samples. FIG. 7A shows the plotted collection of results that would properly have detected 100% of MRSA-positive samples. Of course, included among this collection of results would have been 7 false-positive results arising from co-infections that included MSSA in combination with methicillin-resistant bacteria other than S. aureus. FIG. 7B shows a plot of the identical results, but further includes a horizontal line representing an arbitrary threshold for designating samples as MRSA-positive. In this instance, data points falling above the threshold can be classified as being MRSA-positive. Of course, the value of the threshold can be chosen to achieve a desired balance between the number of true MRSA-positives and false-positives included by the threshold-based assignment. As indicated in FIG. 7B, establishing the arbitrary threshold at −2 minutes, and specifying that ΔCt values greater than this value are associated with MRSA-positive samples captured 44 of 47 true positives, while excluding 4 of 7 false-positives.

In addition to the above-described method of assessing whether a test sample contains MRSA nucleic acids, the invention further relates to a method of assessing whether the test sample contains MSSA bacteria. More particularly, it is possible to analyze results from a single multiplex real-time nucleic acid amplification reaction to assess whether the test sample contains (1) MRSA; or (2) MSSA, even under certain circumstances wherein both of the S. aureus-specific (e.g., 23S rDNA) and methicillin resistance-specific (e.g., mecA) target nucleic acids are detected. Based on the analysis, an assignment is made. Each of MSSA and MRSA is assigned "positive" or "negative" status, with the results being mutually exclusive (i.e., a sample is either negative for both organisms, or positive for only one of the two organisms). Simply stated, a sample is assigned as MRSA positive when there is a positive result for the S. aureus-specific target sequence, and when the ΔCt value determined from indicia of amplification for the real-time run curves for the S. aureus-specific target sequence and the methicillin-resistance target sequence meet or exceed a threshold value. A sample is assigned as MSSA positive when there is a positive result for the S. aureus-specific target sequence, and when the ΔCt value determined from indicia of amplification for the real-time run curves for the S. aureus-specific target sequence and the methicillin-resistance target sequence does not meet or exceed a threshold value. This latter case may be true either when a ΔCt value cannot be calculated because the methicillin resistance marker did not amplify (i.e., the target is absent), or when the ΔCt value is less than the specified threshold value.

Example 5

Assessing the Presence of MRSA and MSSA Using Results from a Single Multiplex Amplification Reaction Having demonstrated how a threshold-based criterion could be used for reducing the number Of false-positive MRSA assignments, we extended the approach to embrace methods of determining whether a test sample contains MSSA nucleic acids. Table 12 describes various individual bacterial target nucleic acids (rows 1-4), and combinations of two bacterial nucleic acids (rows 5-10) that can be tested using a real-time protocol for amplifying and detecting a S. aureus-specific target nucleic acid sequence (e.g., a 23S rDNA sequence), and a methicillin resistance marker (e.g., a mecA sequence). The second and third columns in the table show the expected qualitative results indicating the presence (i.e., "(+)") or absence (i.e., "(−)") of the S. aureus Target and mecA Target, as determined using arbitrary acceptance criteria. Illustrative acceptance criteria useful for this purpose are given above under Example 1. The fourth column shows the result for an arbitrary threshold-based criterion, where ΔCt values are calculated using the indicia of amplification for the S. aureus and mecA target sequences. In this column "NA" indicates the criterion is not applicable because there are lacking the necessary two indicia of amplification used for calculating the ΔCt relationship. The "<" and "≥" symbols respectively indicate ΔCt values that are "less than" and "greater than or equal to" an arbitrary threshold cutoff. In this illustration the arbitrary threshold cutoff was set at −2 minutes, as indicated in FIG. 7B. The fifth and sixth columns respectively indicate the MSSA and MRSA assignments based on the information appearing in the preceding three columns. In these columns, "Positive" indicates that the organism is assigned as being present, and, "Negative" indicates that the organism is assigned as being absent. Detailed explanations of the entries in Table 12 follow. Notably, Table 12 can also be used as a "look-up table" for decoding or interpreting the real-time results.

TABLE 12

Interpretation of Real-Time Amplification Results

| Organism(s) | S. aureus Target | mecA Target | ΔCt Threshold | MSSA Assignment | MRSA Assignment |
|---|---|---|---|---|---|
| S. aureus | (+) | (−) | NA | Positive | Negative |
| MR-CoNS | (−) | (+) | NA | Negative | Negative |
| CoNS | (−) | (−) | NA | Negative | Negative |
| MRSA | (+) | (+) | < | False-Positive | False-Negative |
| | | | ≥ | Negative | Positive |
| S. aureus + MR-CoNS | (+) | (+) | < | Positive | Negative |
| | | | ≥ | False-Negative | False-Positive |
| S. aureus + CoNS | (+) | (−) | NA | Positive | Negative |
| S. aureus + MRSA | (+) | (+) | < | Positive | False-Negative |
| | | | ≥ | False-Negative | Positive |
| CoNS + MR-CoNS | (−) | (+) | NA | Negative | Negative |
| CoNS + MRSA | (+) | (+) | < | False-Positive | False-Negative |
| | | | ≥ | Negative | Positive |
| MR-CoNS + MRSA | (+) | (+) | < | False-Positive | False-Negative |
| | | | ≥ | Negative | Positive |

Table 12 summarizes the interpretation of results from real-time amplification of a *S. aureus*-specific target sequence and a methicillin resistance target sequence. The tabulated information can be used for interpreting results from amplification reactions carried out independently (e.g., conducted in different reaction vessels), or alternatively from a multiplex assay wherein the *S. aureus*-specific target, the methicillin-resistance target, and preferably an internal control are co-amplified in a single amplification reaction. The tabulated results assume that at least one of the three target nucleic acids (i.e., internal control, *S. aureus*-specific target and methicillin resistance target) amplified in the real-time amplification reaction.

As indicated in the first row of Table 12, a trial carried out using only *S. aureus* (i.e., MSSA) nucleic acid yields a positive amplification result for the *S. aureus*-specific target, and a negative result for the methicillin-resistance target. Because the methicillin-resistance target nucleic acid does not amplify, the $\Delta Ct$ value cannot be calculated. This aggregated pattern of results leads to a positive MSSA assignment and a negative MRSA assignment.

As indicated in the second row of Table 12, a trial carried out using only MR-CoNS nucleic acid yields a negative amplification result for the *S. aureus*-specific target, and a positive result for the methicillin-resistance target. Because the *S. aureus*-specific target nucleic acid does not amplify, the $\Delta Ct$ value cannot be calculated. This aggregated pattern of results leads to negative assignments for both MSSA and MRSA. In the absence of a positive result for the *S. aureus*-specific target, there can be only negative assignments for MSSA and MRSA.

As indicated in the third row of Table 12, a trial carried out using only CoNS nucleic acid yields negative amplification results for both the *S. aureus*-specific target and the methicillin-resistance target. Because neither the *S. aureus*-specific target nor the methicillin-resistance target nucleic acid amplifies, the $\Delta Ct$ value cannot be calculated. This aggregated pattern of results leads to negative assignments for both MSSA and MRSA.

As indicated in the fourth row of Table 12, a trial carried out using only MRSA nucleic acid yields positive amplification results for both the *S. aureus*-specific target and the methicillin-resistance target. This combination of results is assigned positive for MRSA and negative for MSSA when a relationship between the indicia of amplification determined using the *S. aureus*-specific target and methicillin-resistance target real-time run curves meets or exceeds a threshold value (e.g., a predetermined threshold value). For example, a trial that yielded a $\Delta Ct$ value falling on or above the arbitrary threshold line drawn in FIG. 7B would correctly be assigned positive for MRSA and negative for MSSA because it meets or exceeds the threshold that distinguishes MRSA-positive from MRSA-negative determinations. If the trial instead yielded an unexpected $\Delta Ct$ value falling below the arbitrary threshold line, it would not be assigned positive for MRSA (i.e., a false-negative assignment), and so would be assigned positive for MSSA (i.e., a false-positive assignment).

As indicated in the fifth row of Table 12, a trial carried out using a mixture of *S. aureus* (i.e., MSSA) and MR-CoNS nucleic acids yields positive amplification results for both the *S. aureus*-specific target and the methicillin-resistance target. As in the case of the trial carried out using only MRSA nucleic acid, this combination of results is assigned positive for MRSA and negative for MSSA only when a relationship between the indicia of amplification determined using the *S. aureus*-specific target and methicillin-resistance target real-time run curves meets or exceeds a threshold value (e.g., a predetermined threshold value). For example, a trial that yielded a $\Delta Ct$ value falling on or above the arbitrary threshold line drawn in FIG. 7B would be assigned positive for MRSA (i.e., a false-positive assignment) and negative for MSSA (i.e., a false-negative assignment) because it meets or exceeds the threshold that distinguishes MRSA-positive from MRSA-negative determinations. If the trial instead yielded a $\Delta Ct$ value falling below the arbitrary threshold line, it would not be assigned positive for MRSA, and so would correctly be assigned positive for MSSA.

As indicated in the sixth row of Table 12, a trial carried out using a mixture of *S. aureus* ((i.e., MSSA) and CoNS nucleic acids yields positive results for the *S. aureus*-specific target and a negative result for the methicillin-resistance target. This leads to a positive assignment for MSSA, and a negative assignment for MRSA. The presence of nucleic acids contributed by the CoNS bacteria does not affect the real-time amplification results.

As indicated in the seventh row of Table 12, a trial carried out using a mixture of *S. aureus* (i.e., MSSA) and MRSA nucleic acids yields positive results for both the *S. aureus*-specific target and the methicillin-resistance target. As in the case of the trial carried out using only MRSA nucleic acid, this combination of results is assigned positive for MRSA and negative for MSSA only when a relationship between the indicia of amplification determined using the *S. aureus*-specific target and methicillin-resistance target real-time run curves meets or exceeds a threshold value (e.g., a predetermined threshold value). For example, a trial that yielded a $\Delta Ct$ value falling on or above the arbitrary threshold line drawn in FIG. 7B would be assigned positive for MRSA and negative for MSSA (i.e., a false-negative assignment) because it meets or exceeds the threshold that distinguishes MRSA-positive from MRSA-negative determinations. If the trial instead yielded a $\Delta Ct$ value falling below the arbitrary threshold line, it would be assigned negative for MRSA (i.e., a false-negative assignment), and assigned positive for MSSA.

As indicated in the eighth row of Table 12, a trial carried out using a mixture of CoNS and MR-CoNS nucleic acids yields a negative result for the *S. aureus*-specific target and a positive result for the methicillin-resistance target. In the absence of a positive result for the *S. aureus*-specific target, there can be only negative assignments for both MSSA and MRSA.

As indicated in the ninth row of Table 12, a trial carried out using a mixture of CoNS and MRSA nucleic acids yields positive results for both the *S. aureus*-specific target and the methicillin-resistance target. As in the case of the trial carried out using only MRSA nucleic acid, this combination of results is assigned positive for MRSA and negative for MSSA only when a relationship between the indicia of amplification determined using the *S. aureus*-specific target and methicillin-resistance target real-time run curves meets or exceeds a threshold value (e.g., a predetermined threshold value). For example, a trial that yielded a $\Delta Ct$ value falling on or above the arbitrary threshold line drawn in FIG. 7B would correctly be assigned positive for MRSA and negative for MSSA because it meets or exceeds the threshold that distinguishes MRSA-positive from MRSA-negative determinations. If the trial instead yielded an unexpected $\Delta Ct$ value falling below the arbitrary threshold line, it would be assigned negative for MRSA (i.e., a false-negative assignment), and would be assigned positive for MSSA (i.e., a false-positive assignment). The presence of nucleic acids contributed by the CoNS bacteria does not affect the real-time amplification results.

As indicated in the last row of Table 12, a trial carried out using a mixture of MR-CoNS and MRSA nucleic acids yields positive results for both the *S. aureus*-specific target and the methicillin-resistance target. As in the case of the trial carried out using only MRSA nucleic acid, this combination of results is assigned positive for MRSA and negative for MSSA only when a relationship between the indicia of amplification determined using the S. aureus-specific target and methicillin-resistance target real-time run curves meets or exceeds a threshold value (e.g., a predetermined threshold value). For example, a trial that yielded a ΔCt value falling on or above the arbitrary threshold line drawn in FIG. 7B would correctly be assigned positive for MRSA and negative for MSSA because it meets or exceeds the threshold that distinguishes MRSA-positive from MRSA-negative determinations. If the trial instead yielded an unexpected ΔCt value falling below the arbitrary threshold line, it would be assigned negative for MRSA (i.e., a false-negative assignment), and would be assigned positive for MSSA (i.e., a false-positive assignment).

The preceding discussion clarifies the origin of positive, negative, and false-positive and false-negative assignments arising from amplification of nucleic acids from single bacterial species, or mixtures of bacterial species containing nucleic acids that can be amplified in the assay. The mixtures of bacterial species represented populations of organisms potentially present in clinical samples, such as nasal swab samples. Notably, it is possible to make an affirmative assignment of either MSSA or MRSA by analyzing results from as few as a single multiplex amplification reaction. This is true even though the assay does not amplify any nucleic acid target sequence present only in S. aureus (i.e., MSSA) but not in MRSA. The information appearing in Table 12 also is relevant to the creation of a "look-up" table for interpreting results from real-time amplification reactions.

An exemplary look-up table is presented as Table 13. The first column in the table gives the result for detection of a S. aureus-specific target sequence. The second column gives the result for detection of a target sequence specific for methicillin resistance. The third column presents alternatives for relationships between the real-time run curves for the amplified S. aureus-specific target and methicillin resistance target. These alternatives are illustrated by ΔCt values that are less than (i.e., "(<)"), and greater than or equal to (i.e., "(≥)") an arbitrarily determined threshold value. When both of the target sequences in the first two columns are present in the sample undergoing testing, the assignment of MSSA and MRSA status depends on the ΔCt value, and on how it relates to the threshold. As illustrated in the look-up table, a ΔCt value less than the threshold value will be assigned positive for MSSA and negative for MRSA. A ΔCt value greater than the threshold value will be assigned negative for MSSA and positive for MRSA.

It may seem counterintuitive to detect positively both S. aureus-specific target and methicillin-resistance target nucleic acids in a qualitative format assay using appropriate acceptance criteria, and then render an assignment as MRSA negative and MSSA positive (i.e., with MSSA possessing only one of the two target nucleic acid sequences). However, the analytical approach is supported by the results presented above in connection with the analysis of clinical samples. Moreover, by this approach number of MRSA false-positive results due to co-infection by MSSA and MR-CoNS advantageously was minimized.

TABLE 13

Look-Up Table for Making MSSA and MRSA Assignments

| S. aureus Target | mecA Target | ΔCt Threshold | MSSA Assignment | MRSA Assignment |
|---|---|---|---|---|
| (+) | (−) | NA | Positive | Negative |
| (−) | (+) | NA | Negative | Negative |
| (−) | (−) | NA | Negative | Negative |
| (+) | (+) | < | Positive | Negative |
|  |  | ≥ | Negative | Positive |

Notably, the numerical value of the arbitrarily chosen ΔCt threshold cutoff (i.e., as illustrated by the horizontal line drawn at −2 minutes in FIG. 7B) influences the % sensitivity, and the % specificity for both MSSA and MRSA determinations. Thus, the value used for the ΔCt threshold cutoff(s) can be adjusted to provide the desired levels of these parameters. For example, the ΔCt threshold cutoff may be set to any of −2 minutes, −4 minutes, −6 minutes, or any value in between to adjust the % sensitivity, and the % specificity assay parameters. This illustrates the flexibility of the approach employing a threshold cutoff for interpreting experimental results, as appear in Table 13.

Figure 8:
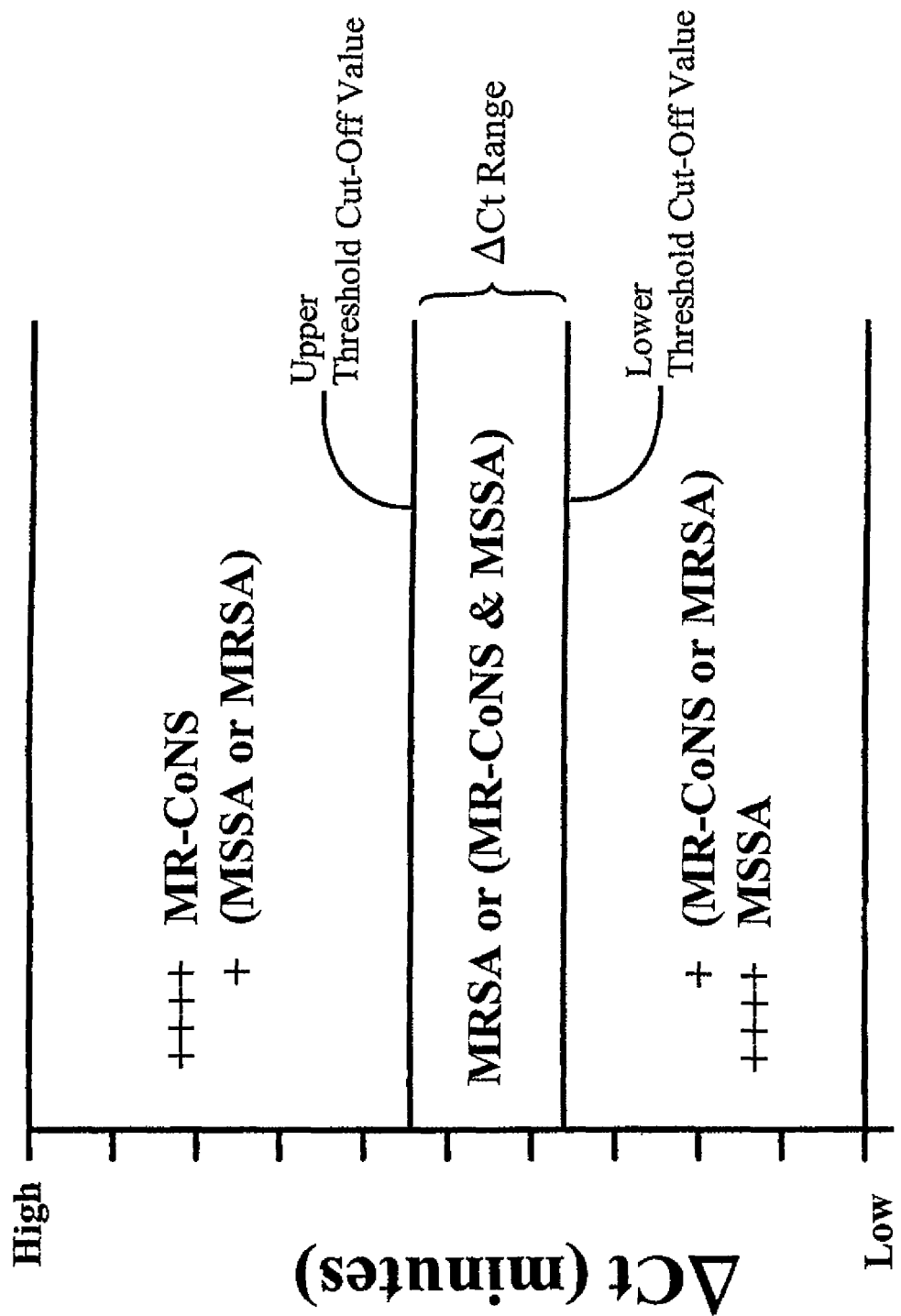
FIG. 8 schematically illustrates how the kinetic analysis can be used for identifying MRSA, or mixed populations of MSSA and MR-CoNS. Upper and lower threshold cut-off values are indicated by horizontal lines, and bound a ΔCt range that is characteristic of MRSA, or possibly mixtures of MR-CoNS and MSSA when present in substantially equal numbers. Regions outside the designated ΔCt range are characteristic of mixtures of MSSA, MR-CoNS and MRSA, at levels represented by "+" symbols (with a greater number of "+" symbols representing greater relative amounts).

The collection of clinical samples used in the foregoing Examples did not include instances of very low levels of MSSA mixed with very high levels of MR-CoNS bacteria. As indicated above (see also FIGS. 7A-7B), the clinical samples used in the preceding Examples were believed skewed somewhat in favor of MSSA and MR-CoNS mixtures having relatively high levels of MSSA and relatively low levels of MR-CoNS. Nonetheless, the preceding evidence and reasoning suggested it should be possible to identify samples that were negative for MRSA, but positive for mixtures of MSSA (at low levels) and MR-CoNS (at high levels), and that those samples would be useful for defining an upper threshold that distinguished clinical samples comprising MRSA from clinical samples comprising mixtures of MSSA and MR-CoNS. FIG. 8 schematically illustrates how upper and lower threshold cut-offs defined ΔCt ranges for determining the identities of MRSA and MSSA bacteria in clinical samples. More particularly, ΔCt values falling between the two thresholds would indicate, or would be consistent with MRSA determinations. In contrast, ΔCt values falling outside the range bounded by the two thresholds would indicate or be associated with infections that either did not include MRSA, or that included MRSA in a very small proportion. Those instances were designated as MRSA-negative. Based on the evidence presented herein, it was substantially more likely that a ΔCt value falling in the indicated ΔCt range was associated with clinical MRSA infection rather than with infection by a mixture of MR-CoNS and MSSA. Thus, in the context of a diagnostic method or assay, ΔCt values falling within the range between the upper and lower threshold cut-off values were designated, or "called" as MRSA-positive results. Any ΔCt value falling outside the ΔCt range was designated or "called" as MRSA-negative. Any ΔCt value falling below the lower threshold cut-off was designated or "called" as MSSA-positive. By this algorithm excellent results were achieved.

Example 6 presents results from testing an extensive collection of clinical samples, and confirms the value of establishing upper and lower threshold cut-off values to define ranges for identifying MRSA and MSSA.

Example 6

Extensive Testing of Clinical Samples Confirms the Utility of ΔCt Ranges

Three hundred eighty-seven clinical nasal swab samples were processed to provide aliquots for nucleic acid testing, and for standard microbiological testing. More specifically, sample swabs were first combined with aliquots of a sample buffer solution consisting of 10 mM Tris (pH 8.0) and 1 mM EDTA, and then vortexed to release adherent material. Following isolation of the liquid phase for subsequent nucleic acid testing, swabs were streaked onto a collection of sterile agar plates that permitted identification of *S. aureus*, MRSA, and coagulase-negative *staphylococcus*. Results from this microbiological testing were used to assign the clinical samples to one of six categories: (1) MR-CoNS only; (2) mixtures of MRSA and MR-CoNS; (3) MRSA only; (4) MSSA; (5) MSSA and MR-CoNS co-infections; and (6) negative samples.

Nucleic acid amplification and monitoring procedures were carried out essentially as described above. Oligonucleotides used for capture, amplification and detection of the *S. aureus*-specific target sequence, the methicillin resistance marker, and the internal control were as described under Example 1, except for substitution of the mecA primer of SEQ ID NO:5 by SEQ ID NO:9. Aliquots of the liquid phases described in the preceding paragraph were used for isolation of genomic DNA, and served as sources of templates for the in vitro nucleic acid amplification reactions. Acceptance criteria for each of the three analytes that coamplified in the multiplex amplification reactions, essentially as described above, were also used for confirming successful amplification results.

Figure 9:
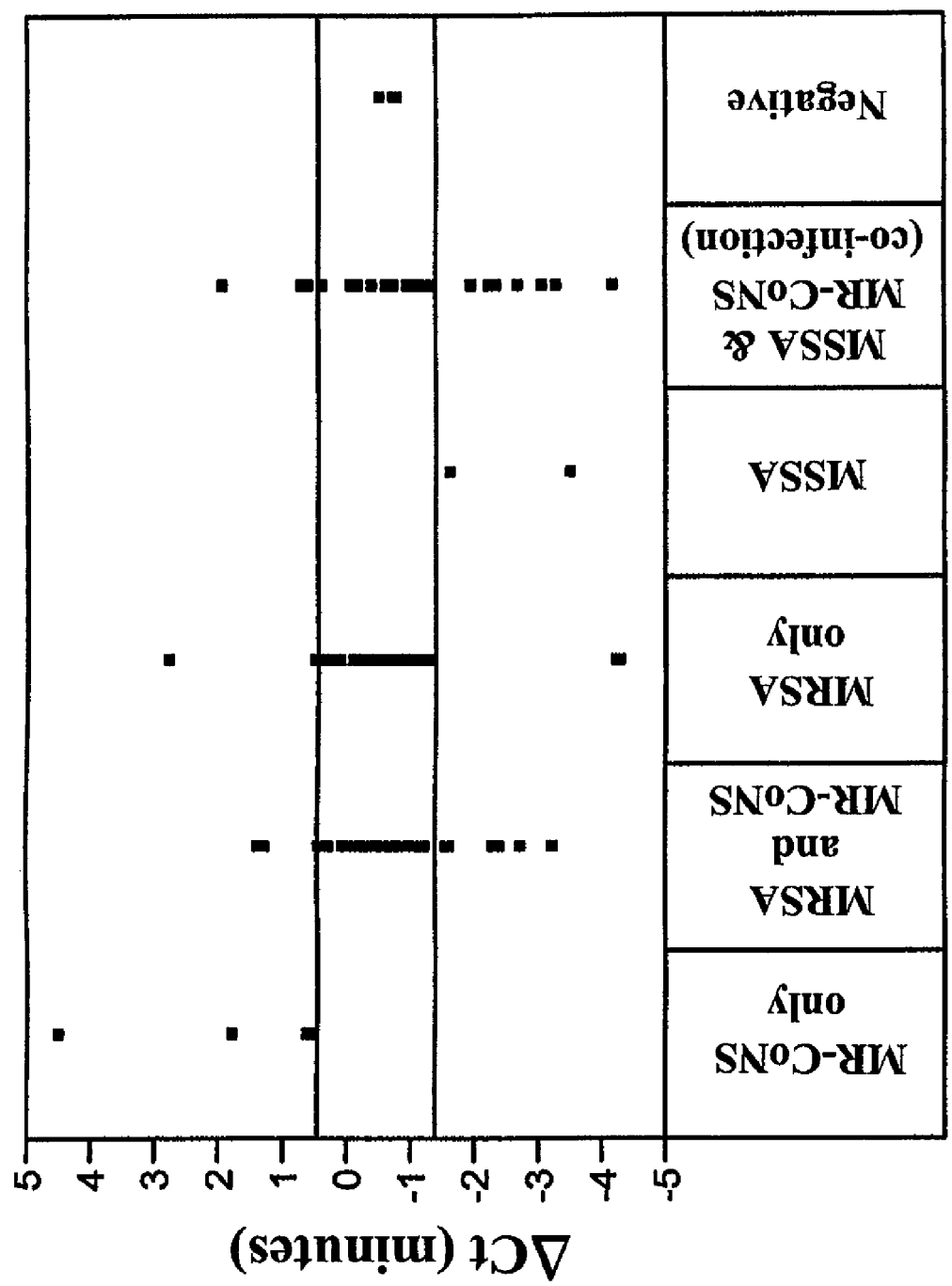
FIG. 9 presents actual data from analysis of clinical samples. Assignments indicated on the lower horizontal axis were made by standard microbiological testing of the clinical samples. To appear as a data point on the plot, a coamplification assay must have contained both the *S. aureus*-specific target sequence and the target sequence specific for methicillin resistance, although the levels of those nucleic acids provided by bacteria of a clinical sample may be very different.

FIG. 9 shows results from the nucleic acid testing of the typed clinical samples. The horizontal axis indicates the different groups of clinical samples identified by microbiological testing. The vertical axis indicates ΔCt values extending from +5 to −5. To appear as a data point in the figure, both of the *S. aureus*-specific target sequence and the methicillin resistance marker must have amplified in the coamplification reaction. A lower threshold cut-off value is shown as a horizontal line drawn at about −1.4 minutes. The position of this line was chosen to maximize agreement between the nucleic acid test results and the results from microbiological assignments. An upper threshold cut-off value is shown as a horizontal line drawn at about +0.4 minutes. The span extending from the lower threshold cut-off value up to the upper threshold cut-off value defined a ΔCt range that was useful for establishing, designating or "calling" that a clinical sample contained MRSA. More particularly, clinical samples yielding genomic DNA that could serve as a template for the coamplification of the *S. aureus*-specific target sequence and the methicillin resistance marker in a manner that gave a ΔCt value falling between the upper and lower threshold cut-off values would be identified, designated or "called" as containing MRSA. Clinical samples yielding genomic DNA that could serve as a template for the coamplification of the *S. aureus*-specific target sequence and the methicillin resistance marker in a manner that gave a ΔCt value falling outside the range between the upper and lower threshold cut-off values would not be identified as containing MRSA. Instead, those trials would be identified as containing MSSA, particularly if the ΔCt value fell below the lower threshold cut-off value, in the area of the plot where the relative level of MSSA was expected to be high (see FIG. 8). Although inspection of FIG. 9 reveals that clinical samples representing mixtures of MSSA and MR-CoNS gave several data points falling in the ΔCt range that identified MRSA, it is to be understood that use of the ΔCt range advantageously reduced the number of false-positive MRSA determinations relative to an alternate procedure that determined the presence of MRSA simply by qualitatively detecting the presence of both the *S. aureus*-specific target sequence and the methicillin resistance marker in the coamplification reaction. If this latter method had been used, all data points shown in FIGS. 7A-7B and 9 would have been determined to be MRSA, and that is clearly incorrect.

Finally, the distribution of data points in FIG. 9 indicates that some of the clinical samples gave rise to unexpected kinetic (i.e., ΔCt) profiles. For example, of 63 clinical samples typed as "MR-CoNS only," a small number of those samples ultimately gave rise to ΔCt values located outside the ΔCt range for MRSA determination, and above the upper threshold cut-off value. As indicated schematically in FIG. 8, this upper portion of the plot is expected for coamplification of very high levels of MR-CoNS (i.e., the source of methicillin resistance marker sequences) combined with very low levels of MSSA (i.e., the source of *S. aureus*-specific target sequence). It is possible that the levels of MSSA in the samples ultimately giving rise to data points in the "MR-CoNS only" category of FIG. 9 were so low that they were not detected by microbiological testing. Similarly, it is possible that samples identified by microbiological testing as "MSSA" actually contained such low levels of MR-CoNS that they were overlooked, but detected in the nucleic acid amplification assay.

What is claimed is:

1. A method of establishing whether a nasal swab sample contains methicillin-sensitive S. aureus bacteria or methicillin-resistant S. aureus bacteria, said method comprising the steps of:
  (a) obtaining nucleic acids from the nasal swab sample;
  (b) coamplifying a S. aureus-specific target sequence and a target sequence specific for methicillin resistance in an in vitro nucleic acid amplification reaction performed using nucleic acids obtained in step (a) as templates,
    wherein each of said target sequences is included among nucleic acids obtained in step (a), and
    wherein amplification products for both of said target sequences are produced and detected in the in vitro nucleic acid amplification reaction;
  (c) determining time-dependent indicia of amplification for the S. aureus-specific target sequence and for the target sequence specific for methicillin resistance that coamplified in step (b);
  (d) calculating a numerical value that is a function of both of said time-dependent indicia of amplification determined in step (c); and
  (e) establishing that
    (1) said biological sample contains methicillin-sensitive S. aureus bacteria if the numerical value calculated in step (d) is less than a threshold criterion value that distinguishes the coamplification kinetics of nucleic acids obtained from
      (i) methicillin-resistant S. aureus bacteria, and
      (ii) a mixture of methicillin-sensitive S. aureus bacteria and methicillin-resistant coagulase-negative bacteria, and
    (2) said biological sample contains methicillin-resistant S. aureus bacteria for all values of the numerical value calculated in step (d) that are greater than said threshold criterion value.

2. The method of claim 1, wherein the threshold criterion value of step (e) is an empirically determined threshold cut-off value.

3. The method of claim 1, wherein the numerical value calculated in step (d) is a numerical $\Delta Ct$ value calculated as a difference between the time-dependent indicia of amplification determined in step (c).

4. The method of claim 3,
  wherein the numerical $\Delta Ct$ value of step (d) is calculated by subtracting the time-dependent indicia of amplification determined for the mecA target sequence from the time-dependent indicia of amplification determined the S. aureus-specific target sequence.

5. The method of claim 1, wherein the obtaining step comprises obtaining genomic DNA.

6. The method of claim 1, wherein the in vitro nucleic acid amplification reaction in step (b) comprises a reverse transcriptase.

7. The method of claim 1, wherein the S. aureus-specific target sequence is a S. aureus ribosomal nucleic acid sequence.

8. The method of claim 1, wherein the determining step comprises determining the time at which a predetermined level of a detectable signal indicative of amplicon production is achieved.

9. The method of claim 1, wherein the target sequence specific for methicillin resistance comprises a mecA target sequence.

10. The method of claim 9, wherein the numerical value calculated in step (d) is a numerical $\Delta Ct$ value calculated as a difference between the time-dependent indicia of amplification determined in step (c).

11. The method of claim 10, wherein the threshold criterion value of step (e) is an empirically determined upper threshold cut-off value.

12. The method of claim 10,
  wherein the numerical $\Delta Ct$ value of step (d) is calculated by subtracting the time-dependent indicia of amplification determined for the mecA target sequence from the time-dependent indicia of amplification determined the S. aureus-specific target sequence.

* * * * *